United States Patent
Callebaut et al.

(10) Patent No.: US 10,414,768 B2
(45) Date of Patent: Sep. 17, 2019

(54) COMPOUNDS FOR TREATING CYSTIC FIBROSIS

(71) Applicants: CENTRE NATIONAL DE LA RECHERCHE SCIENTIFIQUE (CNRS), Paris (FR); UNIVERSITE PIERRE ET MARIE CURIE—PARIS 6 (UPMC), Paris (FR)

(72) Inventors: Isabelle Callebaut, Favieres (FR); Jean-Paul Mornon, Favieres (FR); Jean-Luc Decout, Vaulnaveys le Haut (FR); Frederic Becq, La Chapelle Montreuil (FR); Pierre Lehn, Brest (FR); Brice Hoffman, St Pierre-les-Nemours (FR); Benjamin Boucherle, St Martin d'Heres (FR); Romain Haudecoeur, Grenoble (FR); Antoine Fortune, Aspach-le-Bas (FR); Clement Boinot, Romans (FR); Julien Alliot, Grenoble (FR)

(73) Assignees: Centre National de la Recherche Scientifique (CNRS), Paris (FR); Université Pierre et Marie Curie—Paris 6 (UPMC), Paris (FR)

( * ) Notice: Subject to any disclaimer, the term of this patent is extended or adjusted under 35 U.S.C. 154(b) by 0 days.

(21) Appl. No.: 15/532,309

(22) PCT Filed: Dec. 4, 2015

(86) PCT No.: PCT/EP2015/078729
§ 371 (c)(1),
(2) Date: Jun. 1, 2017

(87) PCT Pub. No.: WO2016/087665
PCT Pub. Date: Jun. 9, 2016

(65) Prior Publication Data
US 2017/0362239 A1    Dec. 21, 2017

(30) Foreign Application Priority Data

Dec. 5, 2014    (EP) .................................. 14196618

(51) Int. Cl.

| | |
|---|---|
| *C07D 487/04* | (2006.01) |
| *A61K 31/4375* | (2006.01) |
| *A61K 31/47* | (2006.01) |
| *A61K 31/505* | (2006.01) |
| *A61K 31/506* | (2006.01) |
| *A61K 31/52* | (2006.01) |
| *C07D 213/74* | (2006.01) |
| *C07D 239/48* | (2006.01) |
| *C07D 471/04* | (2006.01) |
| *C07D 473/40* | (2006.01) |
| *C07D 473/16* | (2006.01) |
| *C07D 473/18* | (2006.01) |
| *C07D 473/34* | (2006.01) |

(52) U.S. Cl.
CPC ........ *C07D 487/04* (2013.01); *A61K 31/4375* (2013.01); *A61K 31/47* (2013.01); *A61K 31/505* (2013.01); *A61K 31/506* (2013.01); *A61K 31/52* (2013.01); *C07D 213/74* (2013.01); *C07D 239/48* (2013.01); *C07D 471/04* (2013.01); *C07D 473/16* (2013.01); *C07D 473/18* (2013.01); *C07D 473/34* (2013.01); *C07D 473/40* (2013.01)

(58) Field of Classification Search
CPC .................................................... C07D 473/40
See application file for complete search history.

(56) References Cited

U.S. PATENT DOCUMENTS

| | | | | |
|---|---|---|---|---|
| 3,930,006 A | * | 12/1975 | Wiggins ............... | A61K 31/515 514/217.06 |
| 6,329,381 B1 | * | 12/2001 | Kurimoto ............ | C07D 473/16 514/263.23 |
| 7,109,330 B2 | * | 9/2006 | Lum ........................ | B60R 1/00 544/277 |

(Continued)

FOREIGN PATENT DOCUMENTS

| | | | |
|---|---|---|---|
| FR | 2 876 583 A1 | | 4/2006 |
| JP | 4160645 B2 | * | 10/2008 |

(Continued)

OTHER PUBLICATIONS

A. Bendich et al., Journal of Biological Chemistry, 1471-1472 (1948).*

(Continued)

*Primary Examiner* — Alexander R Pagano
(74) *Attorney, Agent, or Firm* — W & C IP

(57) ABSTRACT

The present invention relates to compounds of Formula (I) or pharmaceutically acceptable enantiomers, salts, solvates or prodrugs thereof. The invention further relates to the use of the compounds of Formula (I) for the treatment of cystic fibrosis. The invention also relates to a process for manufacturing compounds of Formula (I).

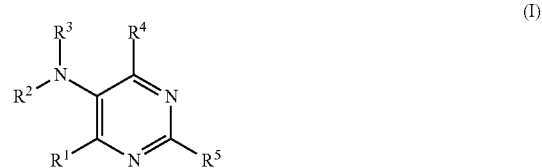

6 Claims, 3 Drawing Sheets

(56) References Cited

U.S. PATENT DOCUMENTS

| | | | | |
|---|---|---|---|---|
| 7,238,700 | B2* | 7/2007 | Palle | C07D 473/16 514/263.37 |
| 8,338,593 | B2* | 12/2012 | Chong | C07F 9/65616 544/157 |
| 8,362,024 | B2 | 1/2013 | Eriksen et al. | |
| 8,372,836 | B2* | 2/2013 | Ketner | A61K 9/1617 514/252.01 |
| 9,556,176 | B2* | 1/2017 | Bonfanti | C07D 473/34 |
| 2008/0008682 | A1* | 1/2008 | Chong | C07F 9/65616 424/85.6 |
| 2009/0036471 | A1* | 2/2009 | Edgard | C07D 487/04 514/261.1 |
| 2009/0202484 | A1* | 8/2009 | Chong | C07F 9/65616 424/85.6 |
| 2010/0093677 | A1 | 4/2010 | Goodhew | |
| 2011/0082146 | A1 | 4/2011 | Atuegbu et al. | |
| 2014/0323441 | A1* | 10/2014 | Bonfanti | C07D 473/34 514/81 |
| 2017/0283419 | A1* | 10/2017 | Bonfanti | C07D 473/34 |

FOREIGN PATENT DOCUMENTS

| | | | | |
|---|---|---|---|---|
| WO | | 2004110352 | | 12/2004 |
| WO | | 2005120497 | | 12/2005 |
| WO | | 2006042949 | | 4/2006 |
| WO | | 2006101740 | | 9/2006 |
| WO | WO-2009034386 | A1 * | 3/2009 | ........... C07D 473/16 |
| WO | | 2012171954 | | 12/2012 |
| WO | | 2014081820 | | 5/2014 |
| WO | | 2014/124230 | A2 | 8/2014 |

OTHER PUBLICATIONS

CAS Indexed Structures for U.S. Pat. No. 7,109,330 (2006).*
K. Tanji et al., 39 Chemical & Pharmaceutical Bulletin, 2793-2796 (1991).*
S Kozai et al., 47 Chemical & Pharmaceutical Bulletin, 574-575 (1999) (Year: 1999).*
Y. Isobe et al., 49 Journal of Medicinal Chemistry, 2088-2095 (2006) (Year: 2006).*
G. Bolin et al., 18 Bioorganic & Medicinal Chemistry Letters, 4368-4372 (2008).*
CAS/CAPLUS Search Report dated Oct. 9, 2018.*
G. Elion et al., 192 Journal of Biological Chemistry, 505-518 (1951).*
H. Koppel et al., 80 Journal of the American Chemical Society, 2751-2755 (1958).*
L. Aguado et al., 11 Journal of Combinatorial Chemistry, 210-212 (2009).*
L. Aguado et al., 53 Journal of Medicinal Chemistry, 316-324 (2010).*
K. El-Bayouki et al., 23 Journal of Heterocyclic Chemistry, 853-856 (1985) (Year: 1985).*
Egan et al., Science, 2004, 304:600-602.
Dalemans et al., Nature, 1991, 354:526-528.
Ashlock and Olson, Annu. Rev. Med. 2011, 62: 107-125.
Cuthbert, Br. J. Pharmacol. 2011, 163:173-183.
Becq et al., J Cyst Fibros 10 (Suppl 2), 2011, S129-S145.
Rowe and Verkman, Cold Spring Harb Perspect Met 2013, 3:a009761.
Riordan, Annu Rev Biochem. 2008, 77:701-726.
Ramsey et al., N Engl J Med. 2011, 365:1663-1672.
Yu et al., J Cyst Fibros. 2012, 11:237-245.
Van Goor et al., Proc Natl Acad Sci U S A. 2011;108(46):18843-8.
Boucherle et al., Eur J Med Chem. 2014, 83:455-465.
Clancy et al., Thorax 2012.
Galietta, 2013 Paediatric Drugs 2013.
De Boeck K et al., Eur Resp J 2013.
Veit G et al., Sci Transl Med 2014.
Cholon DM et al., Sci Transl Med 2014.
Mornon et al., Cell Mol Life Sci. 2008. 65(16):2594-612.
Mornon et al., Cell Mol Life Sci. 2009, 66(21):3469-86.
Mornon et al., Cell Mol Life Sci. 2014.

* cited by examiner

COMPOUNDS FOR TREATING CYSTIC FIBROSIS

FIELD OF INVENTION

The present invention relates to compounds useful as therapeutic compounds, especially in the treatment of cystic fibrosis. The present invention thus further relates to methods for treating cystic fibrosis.

BACKGROUND OF INVENTION

An estimated 70,000 children and adults worldwide have Cystic Fibrosis (CF). CF is a life-threatening genetic disease caused by mutations in the gene encoding for the CFTR protein. CFTR, cystic fibrosis transmembrane conductance regulator, is a chloride channel that is expressed in multiple epithelial cell types. Mutations in the CFTR gene lead to an abnormal water and electrolytes transport through apical cell membranes of numerous exocrine tissues such as the lungs. Mutations of the CFTR gene have been classified in 5 classes of molecular defects of the protein: Class I, premature termination stop codon leading to complete absence of CFTR protein synthesis; Class II, arrested maturation and intracellular localization defect (processing block); Class III, defective activation and regulation of the chloride transport function (gating defect); Class IV, reduced conductance of the chloride channel; and Class V, reduced CFTR protein synthesis. The most common CFTR mutation is the deletion of the phenylalanine residue in position 508 of the polypeptide chain (mutation F508del, mutant protein F508del-CFTR), which belongs to Class II defect. This mutation is present on at least one allele in about 90% of CF patients, with almost 50% of the genotyped patients being F508del homozygous (Egan et al., Science, 2004, 304:600-602). The F508del mutation causes the failure of CFTR to traffic correctly to the plasma membrane because of protein misfolding that retains the protein in the endoplasmic reticulum. In addition, when the F508del-CFTR protein is correctly localized at the plasma membrane, it also has altered intrinsic chloride channel transport function relative to the wild type (WT) CFTR protein (Dalemans et al, Nature, 1991, 354:526-528).

Until recently, current therapies only treated the symptoms of CF disease, including antibiotics, anti-inflammatory agents, mucolytics, nebulized hypertonic saline, pancreatic enzyme replacement, and lung transplantation (Ashlock and Olson, Annu. Rev. Med. 2011, 62: 107-125; Cuthbert, Br. J. Pharmacol. 2011, 163:173-183). There is thus a great interest in innovative therapies that aim to treat the root causes of CF disease and to correct the underlying basic defects responsible for CFTR loss-of-function.

Since the discovery of mutations in CFTR as the cause of CF, a number of studies have been conducted to find, through standard screening methods, a pharmacological small-molecule approach to correct the dysfunction of the mutated proteins (Becq et al, J Cyst Fibros 10 (Suppl 2), 2011, S129-S145; Rowe and Verkman, Cold Spring Harb Perspect Med. 2013, 3:a009761). For missense mutations, small molecules need to facilitate trafficking and delivery of the abnormal protein to the plasma membrane (correctors) and/or to improve its channel gating (potentiators) (Riordan, Annu Rev Biochem. 2008, 77:701-726). A successful example of potentiator is a VX-770/Ivacaftor, which ameliorates significantly the clinical status of CF patients bearing the G551D mutation and shows no major side effects (Ramsey et al, N Engl J Med. 2011, 365:1663-1672; Yu et al, J Cyst Fibros. 2012, 11:237-245). Some small molecule F508del correctors have also been identified by high throughput screening, the most promising one, VX-809 (Van Goor et al. Proc Natl Acad Sci USA. 2011; 108(46):18843-8) has recently been approved by FDA as Orkambi®, a combination of VX-809 with VX-770/Ivacaftor (*FDA approves new treatment for cystic fibrosis*, FDA release Jul. 2, 2015). Indeed, because of the limitations in the efficacy of VX-809 as a monotherapy in vitro and in vivo and the effect of VX-770/Ivacaftor on VX-809 treated cells, it is the use of a combination of the two molecules that has been approved.

Compounds and methods for treating CF due to F508del were described in the art. For example, WO 2006/101740 and WO 2006/042949 describe compounds for correcting cellular processing and cell localization of mutant-CFTR.

WO 2012/171954 discloses TMA and structural analogs to correct intracellular localization of the defective F508del-CFTR, and WO 2014/081820 describes compounds of the class of CFTR correctors to correct the misfolding or defective trafficking of F508del-CFTR. However, the mutant protein also show a reduced conductance of the chloride ion. Thus there is also a need to enhance this reduced function.

WO 2004/110352 and WO 2005/120497 describe compounds having activity in increasing ion transport by mutant-CFTR.

Some derivatives of adenine are explored for their activatory properties of CFTR. These compounds are cyclic methylglyoxal diadducts (Boucherle et al, Eur J Med Chem. 2014, 83:455-465).

U.S. Pat. No. 8,362,024 discloses purinyl derivatives for the treatment of diseases associated with the activity of potassium channels.

However, to the Applicant knowledge, the effects of all these molecules tested alone are limited and do not provide significant clinical benefits (Clancy et al Thorax 2012). Moreover, there are controversies about the interest in combining VX-809 with the VX-770 potentiator, as chronic co-administration in clinical studies produced only little evidence for additivity in CF patient homozygotous for the F508del-CFTR mutation (Galietta 2013 Paediatric Drugs 2013, De Boeck K et al. Eur Resp J 2013) and as it has been shown that VX-770 abrogates pharmacological correction of F508del-CFTR by VX-809 (Veit G et al. Sci Transl Med 2014, Cholon D M et al. Sci Transl Med 2014). Moreover, there is no evidence, at the best of our knowledge, that these correctors do interact directly at the site where is located the F508del mutation. Accordingly, there is still a need for compounds that can restore the localization of F508del-CFTR and/or that can activate F508del-CFTR.

By modeling and analyzing comparatively the 3D structure of CFTR (Mornon et al. Cell Mol Life Sci. 2008. 65(16):2594-612; Mornon et al. Cell Mol Life Sci. 2009, 66(21):3469-86; Mornon et al. Cell Mol Life Sci. 2014, Epub ahead of print) and F508del-CFTR proteins, the Applicant found that the amino acid F508 is localized in a structurally important pocket and is an essential key for the opening of the channel. Therefore, the Applicant designed chemical compounds interacting with residues of the pocket, through a novel, structure-based approach. The Applicant found that some of these compounds allow correcting the maturation of the F508del-CFTR protein, thereby restoring CFTR localization and activity.

SUMMARY

This invention thus relates to a compound of general Formula I:

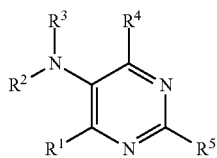
(I)

and pharmaceutically acceptable enantiomers, salts, solvates and prodrugs thereof, wherein:

$R^1$ represents $NR^6R^7$; halo; $OR^6$; or $SO_nR^8$ wherein n is 0, 1, 2 or 3 and wherein $R^8$ represents H, $NH_2$, alkyl, aryl, heteroaryl, arylalkyl, heteroarylalkyl or alkyloxyaryl; preferably $R^1$ represents halo or $NR^6R^7$;

when $R^1$ is halo, $SO_nR^8$ or $OR^6$, then
  $R^2$ and $R^3$ both represent H;

when $R^1$ is $NR^6R^7$, then
  $R^2$ and $R^3$ represent each independently H, alkyl, aryl, heteroaryl, arylalkyl, heteroarylalkyl, alkyloxyaryl, formyl, alkylcarbonyl, arylcarbonyl, heteroarylcarbonyl, arylalkylcarbonyl, heteroarylalkylcarbonyl or alkyloxyarylcarbonyl; preferably $R^2$ and $R^3$ represent each independently H, alkyl, aryl, heteroaryl, arylalkyl, heteroarylalkyl, alkyloxyaryl, formyl, alkylcarbonyl, arylcarbonyl, heteroarylcarbonyl, arylalkylcarbonyl, heteroarylalkylcarbonyl, alkyloxyarylcarbonyl, and $R^7$ represent H; more preferably $R^2$ and $R^3$ represent both H and $R^7$ represents H;
  or
  $R^2$, $R^3$ and $R^7$ are linked together and form the link =X— between the two nitrogen atoms, wherein X represent $CR^9$ or N, wherein $R^9$ represents H; OH; halo; C1-C4-alkyl; $SO_mR^{10}$ wherein m is 0, 1, 2 or 3 and wherein $R^{10}$ represents H, $NH_2$ or C1-C4-alkyl; or $NR^{11}R^{12}$ wherein $R^{11}$ and $R^{12}$ represent each independently H or C1-C4-alkyl; preferably $R^9$ represents H;

$R^4$ represents H; halo; $NH_2$; OH; alkyloxy; aryloxy; heteroaryloxy; —O—CO—NH—$CHPh_2$; $NR^{13}R^{14}$ wherein $R^{13}$ and $R^{14}$ represent each independently an alkyl group, preferably $R^{13}$ and $R^{14}$ represent both ethyl; —NH-Ph-$CONH_2$; —NH—$CH_2$—$R^{15}$ wherein $R^{15}$ represents COOH, —COOalkyl, alkyloxyaryl, arylalkyl or heteroarylalkyl, preferably $R^{15}$ represents COOH, —COOtBu, methoxyphenyl, phenylpropyl; —NH—$CHR^{16}R^{17}$ wherein $R^{16}$ represents hydroxymethyl or methyl and $R^{17}$ represents hydroxymethyl, COOH or COOalkyl, preferably $R^{17}$ represents hydroxymethyl, COOH, COOtBu; or —NHCO—$R^{18}$ wherein $R^{18}$ represents H, alkyl, aryl, heteroaryl, arylalkyl, heteroarylalkyl or alkyloxyaryl; preferably $R^4$ represents Cl, $NH_2$, OH, —O—CO—NH—$CHPh_2$, $NEt_2$, —NH-p-Ph-$CONH_2$; —NH—$CH_2$—$R^{15}$ wherein $R^{15}$ represents COOH, —COOtBu, p-methoxyphenyl, phenylpropyl; —NH—$CHR^{16}R^{17}$ wherein $R^{16}$ represents hydroxymethyl or methyl and $R^{17}$ represents hydroxymethyl, COOH, COOtBu; more preferably $R^4$ represents Cl, $NH_2$, —NH—$CHR^{16}R^{17}$ wherein $R^{16}$ represents methyl and $R^{17}$ represents COOH;

$R^5$ represents H; halo; alkyl; OH; alkyloxy; aryloxy; arylalkyloxy, heteroarylalkyloxy; $SO_pR^{19}$ wherein p is 0, 1, 2 or 3 and wherein $R^{19}$ represents H, $NH_2$, alkyl aryl, heteroaryl, arylalkyl, heteroarylalkyl or alkyloxyaryl; or $NR^{20}R^{21}$ wherein $R^{20}$ and $R^{21}$ represents each independently a group selected from H, alkyl, arylalkyl, heteroarylalkyl, aryl, heteroaryl, alkyloxyaryl, formyl, alkylcarbonyl, arylcarbonyl, heteroarylcarbonyl, arylalkylcarbonyl, heteroarylalkylcarbonyl and alkyloxyarylcarbonyl; preferably $R^5$ represents H, Cl, methyl, phenylpropyloxy, phenylethyloxy, $NH_2$, phenylpropylamino, phenylethylamino, methylcarbonylamino; more preferably $R^5$ represents H, Cl, $NH_2$, phenyl-n-propylamino;

$R^6$ and $R^7$ represent each independently H; arylalkyl wherein the aryl group is optionally substituted by one or more group selected from halo and carboxyl; heteroarylalkyl; heteroarylaminoalkyl wherein the heteroaryl group is optionally substituted by one or more group selected from halo and $NH_2$; aminoalkyl; aryl substituted by one or more group selected from alkyloxy, hydroxymethyl, $CONH_2$, COOH, COOalkyl, $SO_3H$ and $SO_2NH_2$; preferably $R^6$ represents H, phenylalkyl wherein the phenyl group is optionally substituted by one or more group selected from fluoro and carboxyl and wherein the alkyl is preferably selected from methyl, ethyl, n-propyl, n-butyl; heteroarylalkyl wherein the heteroaryl is preferably pyridine and wherein the alkyl group is preferably selected from methyl and ethyl; heteroarylaminoalkyl wherein the heteroaryl group is optionally substituted by one or more group selected from Cl and $NH_2$ and wherein the heteroaryl is preferably pyrimidine and wherein the alkyl group is preferably selected from ethyl and n-propyl; amino-n-propyl; phenyl substituted in para or meta, preferably in para, by one or more group selected from hydroxymethyl, $CONH_2$, COOH, COOMe and $SO_3H$; more preferably $R^6$ represents H, phenyl-n-propyl, phenyl substituted in para by hydroxymethyl or $CONH_2$ and $R^7$ represents H;

provided that:
  $R^4$ and $R^5$ are not both H;
  $R^5$ and $R^6$ are not both H;
  $R^5$ and $R^4$ are not both Cl;

for use in the treatment of a disease or disorder associated with chloride channels.

According to one embodiment, the compound for use according to the invention is of general Formula Ib:

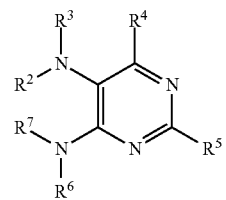
(Ib)

and pharmaceutically acceptable enantiomers, salts, solvates and prodrugs thereof, wherein $R^4$, $R^5$, $R^6$ and $R^7$ are as defined in Formula I;

$R^2$ and $R^3$ represent each independently H, alkyl, aryl, heteroaryl, arylalkyl, heteroarylalkyl, alkyloxyaryl, formyl, alkylcarbonyl, arylcarbonyl, heteroarylcarbonyl, arylalkylcarbonyl, heteroarylalkylcarbonyl or alkyloxyarylcarbonyl; preferably $R^2$ and $R^3$ represent each independently H, alkyl, aryl, heteroaryl, arylalkyl, heteroarylalkyl, alkyloxyaryl, formyl, alkylcarbonyl, arylcarbonyl, heteroarylcarbonyl, arylalkylcarbonyl, heteroarylalkylcarbonyl, alkyloxyarylcarbonyl, and R⁷ represent H; more preferably R² and R³ represent both H and R⁷ represents H;

or

R², R³ and R⁷ are linked together and form the link =X— between the two nitrogen atoms, wherein X represent CR⁹ or N, wherein R⁹ represents H; OH; halo; C1-C4-alkyl; SO$_m$R¹⁰ wherein m is 0, 1, 2 or 3 and wherein R¹⁰ represents H, NH₂ or C1-C4-alkyl; or NR¹¹R¹² wherein R¹¹ and R¹² represent each independently H or C1-C4-alkyl; preferably R⁹ represents H.

According to one embodiment, the compound for use according to the invention is of Formula Ib-1:

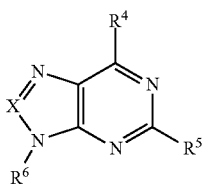

(Ib-1)

and pharmaceutically acceptable enantiomers, salts, solvates and prodrugs thereof, wherein X, R⁴, R⁵ and R⁶ are as defined in Formula I.

According to one embodiment, the compound for use according to the invention is of Formula Ib-2a:

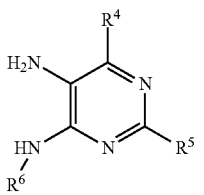

(Ib-2a)

and pharmaceutically acceptable enantiomers, salts, solvates and prodrugs thereof, wherein R⁴, R⁵ and R⁶ are as defined in Formula I.

According to one embodiment, the compound for use according to the invention is of Formula Ia:

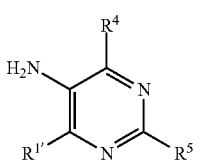

(Ia)

and pharmaceutically acceptable enantiomers, salts, solvates and prodrugs thereof, wherein R⁴ and R⁵ are as defined in Formula I; and R¹' represents halo, SO$_n$R⁸ or OR⁶ wherein R⁶ and R⁸ are as defined in Formula I, preferably R¹' represents halo, more preferably R¹' represents Cl.

According to one embodiment, the compound of Formula I according to the invention is for use for treating a disease or disorder associated with the CFTR protein, preferably the disease is cystic fibrosis.

According to one embodiment, cystic fibrosis is due to a mutation of the gene encoding the CFTR protein, preferably cystic fibrosis is due to the deletion of the phenylalanine residue at the position 508.

The invention further relates to a pharmaceutical composition comprising a compound of general Formula I':

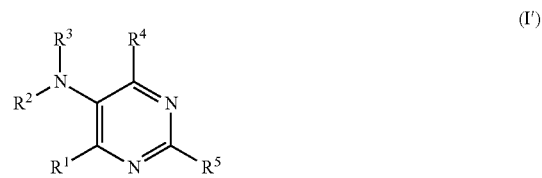

(I')

and pharmaceutically acceptable enantiomers, salts, solvates and prodrugs thereof, wherein:

R¹ represents NR⁶R⁷; halo; OR⁶; or SO$_n$R⁸ wherein n is 0, 1, 2 or 3 and wherein R⁸ represents H, NH₂, alkyl, aryl, heteroaryl, arylalkyl, heteroarylalkyl, alkyloxyaryl;

when R¹ is halo, SO$_n$R⁸ or OR⁶, then
R² and R³ both represent H;

when R¹ is NR⁶R⁷, then
R² and R³ represent each independently H, alkyl, aryl, heteroaryl, arylalkyl, heteroarylalkyl, alkyloxyaryl, formyl, alkylcarbonyl, arylcarbonyl, heteroarylcarbonyl, arylalkylcarbonyl, heteroarylalkylcarbonyl or alkyloxyarylcarbonyl;

or

R², R³ and R⁷ are linked together and form the link =X— between the two nitrogen atoms, wherein X represent CR⁹ or N, wherein R⁹ represents H; OH; halo; C1-C4-alkyl; SO$_m$R¹⁰ wherein m is 0, 1, 2 or 3 and wherein R¹⁰ represents H, NH₂ or C1-C4-alkyl; or NR¹¹R¹² wherein R¹¹ and R¹² represent each independently H or C1-C4-alkyl;

R⁴ represents H; halo; NH₂; OH; alkyloxy; aryloxy; heteroaryloxy; —O—CO—NH—CHPh₂; NR¹³R¹⁴ wherein R¹³ and R¹⁴ represent each independently an alkyl group; —NH-Ph-CONH₂; —NH—CH₂—R¹⁵ wherein R¹⁵ represents COOH, —COOalkyl, alkyloxyaryl, arylalkyl or heteroarylalkyl; —NH—CHR¹⁶R¹⁷ wherein R¹⁶ represents hydroxymethyl or methyl and R¹⁷ represents hydroxymethyl, COOH or COOalkyl; or —NHCO—R¹⁸ wherein R¹⁸ represents H, alkyl, aryl, heteroaryl, arylalkyl, heteroarylalkyl or alkyloxyaryl;

R⁵ represents H; halo; alkyl; OH; alkyloxy; aryloxy; arylalkyloxy; heteroarylalkyloxy; SO$_p$R¹⁹ wherein p is 0, 1, 2 or 3 and wherein R¹⁹ represents H, NH₂, alkyl aryl, heteroaryl, arylalkyl, heteroarylalkyl or alkyloxyaryl; or NR²⁰R²¹ wherein R²⁰ and R²¹ represents each independently a group selected from H, alkyl, arylalkyl, heteroarylalkyl, aryl, heteroaryl, formyl, alkylcarbonyl, arylcarbonyl, heteroarylcarbonyl, arylalkylcarbonyl, heteroarylalkylcarbonyl and alkyloxyarylcarbonyl;

R⁶ and R⁷ represent each independently H; arylalkyl wherein the aryl group is optionally substituted by one or more group selected from halo and carboxyl; heteroarylalkyl; heteroarylaminoalkyl wherein the heteroaryl group is optionally substituted by one or more group selected from halo and NH₂; aminoalkyl; aryl substituted by one or more group selected from alkyloxy, hydroxymethyl, CONH₂, COOH, COOalkyl, SO₃H and SO₂NH₂;

provided that:
R$^4$ and R$^5$ are not both H;
R$^5$ and R$^6$ are not both H;
R$^5$ and R$^4$ are not both Cl;
and provided that compound of Formula I' is not
4-(2-amino-6-hydroxy-9H-purin-9-yl)benzamide;
N$^2$-2-phenethyl-9H-purine-2,6-diamine;
9-benzyl-2-chloro-N-(4-methoxybenzyl)-9H-purin-6-amine;
4,6-dichloropyrimidin-5-amine;
4,6-dichloropyrimidine-2,5-diamine;
and at least one pharmaceutically acceptable carrier.

The invention further relates to a medicament comprising a compound of general Formula I', as defined above.

According to one embodiment, the medicament according to the invention is for use for treating cystic fibrosis.

The present invention also relates to a compound of general Formula I",

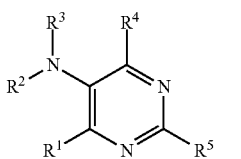

(I")

and pharmaceutically acceptable enantiomers, salts, solvates and prodrugs thereof, wherein:
R$^1$ represents NR$^6$R$^7$; halo; OR$^6$; or SO$_n$R$^8$ wherein n is 0, 1, 2 or 3 and wherein R$^8$ represents H, NH$_2$, alkyl, aryl, heteroaryl, arylalkyl, heteroarylalkyl, alkyloxyaryl;
when R$^1$ is halo, SO$_n$R$^8$ or OR$^6$, then
R$^2$ and R$^3$ both represent H;
when R$^1$ is NR$^6$R$^7$, then
R$^2$ and R$^3$ represent each independently H, alkyl, aryl, heteroaryl, arylalkyl, heteroarylalkyl, alkyloxyaryl, formyl, alkylcarbonyl, arylcarbonyl, heteroarylcarbonyl, arylalkylcarbonyl, heteroarylalkylcarbonyl or alkyloxyarylcarbonyl;
or
R$^2$, R$^3$ and R$^7$ are linked together and form the link =X— between the two nitrogen atoms, wherein X represent CR$^9$ or N, wherein R$^9$ represents H; OH; halo; C1-C4-alkyl; SO$_m$R$^{10}$ wherein m is 0, 1, 2 or 3 and wherein R$^{10}$ represents H, NH$_2$ or C1-C4-alkyl; or NR$^{11}$R$^{12}$ wherein R$^{11}$ and R$^{12}$ represent each independently H or C1-C4-alkyl;
R$^4$ represents H; halo; NH$_2$; OH; alkyloxy; aryloxy; heteroaryloxy; —O—CO—NH—CHPh$_2$; NR$^{13}$R$^{14}$ wherein R$^{13}$ and R$^{14}$ represent each independently an alkyl group; —NH-Ph-CONH$_2$; —NH—CH$_2$—R$^{15}$ wherein R$^{15}$ represents COOH, —COOalkyl, alkyloxyaryl, arylalkyl or heteroarylalkyl; —NH—CHR$^{16}$R$^{17}$ wherein R$^{16}$ represents hydroxymethyl or methyl and R$^{17}$ represents hydroxymethyl, COOH or COOalkyl; or —NHCO—R$^{18}$ wherein R$^{18}$ represents H, alkyl, aryl, heteroaryl, arylalkyl, heteroarylalkyl or alkyloxyaryl;
R$^5$ represents H; halo; alkyl; OH; alkyloxy; aryloxy; arylalkyloxy; heteroarylalkyloxy; SO$_p$R$^{19}$ wherein p is 0, 1, 2 or 3 and wherein R$^{19}$ represents H, NH$_2$, alkyl aryl, heteroaryl, arylalkyl, heteroarylalkyl or alkyloxyaryl; or NR$^{20}$R$^{21}$ wherein R$^{20}$ and R$^{21}$ represents each independently a group selected from H, arylalkyl, heteroarylalkyl, aryl, heteroaryl, formyl, alkylcarbonyl, arylcarbonyl, heteroarylcarbonyl, arylalkylcarbonyl, heteroarylalkylcarbonyl and alkyloxyarylcarbonyl;
R$^6$ and R$^7$ represent each independently H; arylalkyl wherein the aryl group is optionally substituted by one or more group selected from halo and carboxyl; heteroarylalkyl; heteroarylaminoalkyl wherein the heteroaryl group is optionally substituted by one or more group selected from halo and NH$_2$; aminoalkyl; aryl substituted by one or more group selected from alkyloxy, hydroxymethyl, CONH$_2$, COOH, COOalkyl, SO$_3$H and SO$_2$NH$_2$;
provided that:
R$^4$ and R$^5$ are not both H;
R$^5$ and R$^6$ are not both H;
R$^5$ and R$^4$ are not both Cl;
and provided that compound of Formula I" is not
4-(2-amino-6-hydroxy-9H-purin-9-yl)benzamide;
N$^2$-2-phenethyl-9H-purine-2,6-diamine;
9-benzyl-9H-purin-6-amine;
9-(3-phenylpropyl)-9H-purin-6-amine;
4-(2-amino-6-hydroxy-9H-purin-9-yl)benzoic acid;
9-benzyl-2-chloro-N-(4-methoxybenzyl)-9H-purin-6-amine;
4,6-dichloropyrimidin-5-amine;
4,6-dichloropyrimidine-2,5-diamine;
2-chloro-9H-purin-6-amine;
2-amino-9H-purin-6-ol;
3-(2-amino-6-hydroxy-9H-purin-9-yl)benzoic acid.

According to one embodiment, the compound according to the invention is selected from the group consisting of:
9-benzyl-2-chloro-9H-purin-6-amine;
9-benzyl-N$^2$-(3-phenylpropyl)-9H-purine-2,6-diamine;
9-benzyl-N$^6$-(4-methoxybenzyl)-N$^2$-(3-phenylpropyl)-9H-purine-2,6-diamine;
(S)-2-((9-benzyl-2-((3-phenylpropyl)amino)-9H-purin-6-yl)amino)propanoic acid;
N$^2$-(3-phenylpropyl)-9H-purine-2,6-diamine;
2-chloro-N-(3-phenylpropyl)-9H-purin-6-amine;
2-chloro-N-(4-methoxybenzyl)-9H-purin-6-amine;
N$^6$-(4-methoxybenzyl)-N$^2$-(3-phenylpropyl)-9H-purine-2,6-diamine;
N-(4-methoxybenzyl)-2-(3-phenylpropoxy)-9H-purin-6-amine;
N-(4-methoxybenzyl)-2-phenethoxy-9H-purin-6-amine;
(S)-tert-butyl 2-((2-chloro-9H-purin-6-yl)amino)propanoate;
(S)-2-((2-chloro-9-(4-(hydroxymethyl)phenyl)-9H-purin-6-yl)amino)propanoic acid;
(S)-tert-butyl 2-((2-chloro-9-(4-(hydroxymethyl)phenyl)-9H-purin-6-yl)amino)propanoate;
4-(6-chloro-9H-purin-9-yl)benzamide;
4-(2-chloro-6-(diethylamino)-9H-purin-9-yl)benzamide;
4-(6-amino-2-chloro-9H-purin-9-yl)benzamide;
4-(6-amino-9H-purin-9-yl)benzamide;
4-(2,6-diamino-9H-purin-9-yl)benzamide;
4-(2-chloro-6-((1,3-dihydroxypropan-2-yl)amino)-9H-purin-9-yl)benzamide;
(S)-2-((9-(4-carbamoylphenyl)-2-chloro-9H-purin-6-yl)amino)-3-hydroxypropanoic acid;
2-((9-(4-carbamoylphenyl)-2-chloro-9H-purin-6-yl)amino)acetic acid;
tert-butyl 2-((9-(4-carbamoylphenyl)-2-chloro-9H-purin-6-yl)amino)acetate;
4-(2-chloro-6-((4-methoxybenzyl)amino)-9H-purin-9-yl)benzamide;

(S)-2-((9-(4-carbamoylphenyl)-2-chloro-9H-purin-6-yl)amino)propanoic acid;
(S)-tert-butyl 2-((9-(4-carbamoylphenyl)-2-chloro-9H-purin-6-yl)amino)propanoate;
4-(2-amino-6-((4-carbamoylphenyl)amino)-9H-purin-9-yl)benzamide;
methyl 4-(2-acetamido-6-((benzhydrylcarbamoyl)oxy)-9H-purin-9-yl)benzoate;
methyl 4-(2-amino-6-hydroxy-9H-purin-9-yl)benzoate;
methyl 4-(2-acetamido-6-hydroxy-9H-purin-9-yl)benzoate;
4-(7-chloro-3H-[1,2,3]triazolo[4,5-d]pyrimidin-3-yl)benzamide;
tert-butyl 2-((5-amino-3-(4-carbamoylphenyl)-3H-[1,2,3]triazolo[4,5-d]pyrimidin-7-yl)amino)acetate;
6-chloro-$N^4$-(4-phenylbutyl)pyrimidine-4,5-diamine;
3-((5-amino-6-chloropyrimidin-4-yl)amino)propan-1-aminium chloride;
6-chloro-$N^4$-(3-phenylpropyl)pyrimidine-4,5-diamine;
$N^4,N^{4'}$-(propane-1,3-diyl)bis(6-chloropyrimidine-4,5-diamine);
6-chloro-$N^4$-phenethylpyrimidine-4,5-diamine;
6-chloro-$N^4$-(4-fluorophenethyl)pyrimidine-4,5-diamine;
6-chloro-$N^4$-(2-(pyridin-4-yl)ethyl)pyrimidine-4,5-diamine;
$N^4,N^{4'}$-(ethane-1,2-diyl)bis(6-chloropyrimidine-4,5-diamine);
$N^4$-benzyl-6-chloropyrimidine-4,5-diamine;
4-(((5-amino-6-chloropyrimidin-4-yl)amino)methyl)benzoic acid;
6-chloro-$N^4$-(pyridin-3-ylmethyl)pyrimidine-4,5-diamine;
6-chloro-$N^4$-(pyridin-4-ylmethyl)pyrimidine-4,5-diamine;
4-((5-amino-6-chloropyrimidin-4-yl)amino)benzamide;
4,6-bis((4-carbamoylphenyl)amino)-2-methylpyrimidin-5-aminium chloride;
3-((5-amino-6-chloropyrimidin-4-yl)amino)benzamide;
4-((5-amino-6-chloropyrimidin-4-yl)amino)benzenesulfonic acid;
2-(3-phenylpropoxy)-9H-purin-6-amine;
(4-(6-amino-2-chloro-9H-purin-9-yl)phenyl)methanol;
4-((5-amino-6-chloropyrimidin-4-yl)oxy)benzamide;
4-((5-amino-6-chloropyrimidin-4-yl)amino)benzenesulfonamide;
(S)-2-((9-(4-(hydroxymethyl)phenyl)-2-((3-phenylpropyl)amino)-9H-purin-6-yl)amino)propanoic acid;
N6-(4-methoxybenzyl)-N2-(4-phenylbutyl)-9H-purine-2,6-diamine;
4-((5,6-diaminopyrimidin-4-yl)amino)benzamide;
4-(6-((4-methoxybenzyl)amino)-2-((3-phenylpropyl)amino)-9H-purin-9-yl)benzamide;
(4-(2,6-diamino-9H-purin-9-yl)phenyl)methanol;
4-(2-amino-6-methoxy-9H-purin-9-yl)benzamide;
4-(2-amino-9H-purin-9-yl)benzamide;
4-(7-chloro-3H-[1,2,3]triazolo[4,5-d]pyrimidin-3-yl)benzenesulfonamide;
4-((5-amino-6-chloro-2-methylpyrimidin-4-yl)amino)benzamide;
4-chloro-6-(3-phenylpropoxy)pyrimidin-5-amine;
4,6-dichloro-2-methylpyrimidin-5-amine;
6-chloropyrimidine-2,4,5-triamine;
N-(6-chloro-9H-purin-2-yl)-3-phenylpropanamide;
4-((5-amino-6-hydroxypyrimidin-4-yl)amino)benzamide;
N2-(4-phenylbutyl)-9H-purine-2,6-diamine;
ethyl 4-((5-amino-6-ethoxypyrimidin-4-yl)amino)benzoate;
2-chloro-9H-purin-6-amine;
4-((5-amino-6-methoxypyrimidin-4-yl)amino)benzamide;
4-(6-chloro-9H-purin-9-yl)benzenesulfonamide;
4-(6-chloro-8-methyl-9H-purin-9-yl)benzamide;
(4-((5-aminopyrimidin-4-yl)amino)phenyl)methanol.

The present invention further relates to a compound of general Formula II:

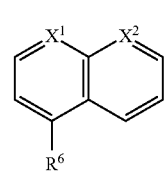

and pharmaceutically acceptable enantiomers, salts, solvates and prodrugs thereof, wherein
$X^1$ and $X^2$ represent respectively CH and N or N and CH;
$R^6$ represents H, arylalkyl wherein the aryl group is optionally substituted by one or more group selected from halo and carboxyl; heteroarylalkyl; heteroarylaminoalkyl wherein the heteroaryl group is optionally substituted by one or more group selected from halo and $NH_2$; aminoalkyl; or aryl substituted by one or more group selected from alkyloxy, hydroxymethyl, $CONH_2$, COOH, COOalkyl, $SO_3H$ and $SO_2NH_2$; preferably $R^6$ represents H, phenylalkyl wherein the phenyl group is optionally substituted by one or more group selected from fluoro and carboxyl and wherein the alkyl is preferably selected from methyl, ethyl, n-propyl, n-butyl; heteroarylalkyl wherein the heteroaryl is preferably pyridine and wherein the alkyl group is preferably selected from methyl and ethyl; heteroarylaminoalkyl wherein the heteroaryl group is optionally substituted by one or more group selected from Cl and $NH_2$ and wherein the heteroaryl is preferably pyrimidine and wherein the alkyl group is preferably selected from ethyl and n-propyl; amino-n-propyl; phenyl substituted in para or meta, preferably in para, by one or more group selected from hydroxymethyl, $CONH_2$, COOH, COOMe and $SO_3H$; more preferably $R^6$ represents phenyl substituted in para by hydroxymethyl or $CONH_2$;
for use in the treatment of a disease or disorder associated with chloride channels.

According to one embodiment, the compound of Formula II according to the invention is for use for treating a disease or disorder associated with the CFTR protein, preferably the disease is cystic fibrosis.

Definitions

In the present invention, the expression "compound of the invention" encompasses compounds of Formula I and of Formula II and related subformulae, in particular those of Tables 1 and 2, or a pharmaceutically acceptable enantiomer, salt, solvate and prodrug thereof.

According to one embodiment, where chemical groups may be substituted, such groups may be substituted with one or more substituents, and preferably with one, two or three substituents. Substituents may be selected from but not limited to, for example, the group comprising halogen, hydroxyl, alkoxy, oxo, nitro, amido (i.e. —C(═O)—NR$_2$ moiety, wherein R represent preferably H, alkyl, aryl; preferably "amido" refers to —C(═O)—NH$_2$), carboxy, amino, cyano, and haloalkyl.

Where chemical substituents are combinations of chemical groups, the point of attachment of the substituent to the molecule is by the last chemical group recited. For example, an arylalkyl substituent is linked to the rest of the molecule through the alkyl moiety and it may by represented as follows: "aryl-alkyl-".

The term "halo" means fluoro, chloro, bromo, or iodo. Preferred halo groups are fluoro and chloro.

The term "alkyl" by itself or as part of another substituent refers to a hydrocarbyl radical of Formula $C_nH_{2n+1}$ wherein n is a number greater than or equal to 1. Generally, alkyl groups of this invention comprise from 1 to 6 carbon atoms, preferably from 1 to 4 carbon atoms, more preferably from 1 to 3 carbon atoms. Alkyl groups may be linear or branched and may be substituted as indicated herein. Suitable alkyl groups include methyl, ethyl, n-propyl, i-propyl, n-butyl, i-butyl, s-butyl and t-butyl, pentyl and its isomers (e.g. n-pentyl, iso-pentyl), and hexyl and its isomers (e.g. n-hexyl, iso-hexyl).

The term "aryl" refers to a polyunsaturated, aromatic hydrocarbyl group having a single ring (i.e. phenyl) or multiple aromatic rings fused together (e.g. naphtyl), typically containing 5 to 12 atoms; preferably 6 to 10, wherein at least one ring is aromatic. The aromatic ring may optionally include one to two additional rings (either cycloalkyl, heterocyclyl or heteroaryl) fused thereto. According to a specific embodiment, the aryl moiety is optionally substituted. Substituents may be selected from but not limited to, for example, the group comprising halogen, hydroxyl, alkoxy, oxo, nitro, amido, carboxy, amino, cyano, and haloalkyl. According to a preferred embodiment, the aryl moiety is optionally substituted by an amido group, preferably of formula —C(═O)—NH$_2$).

Where at least one carbon atom in an aryl group is replaced with a heteroatom, the resultant ring is referred to herein as a heteroaryl ring.

The term "heteroaryl" refers to 5 to 12 carbon-atom aromatic rings or ring systems containing 1 to 2 rings which are fused together or linked covalently, typically containing 5 to 6 atoms; at least one of which is aromatic, in which one or more carbon atoms in one or more of these rings is replaced by oxygen, nitrogen and/or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyridinyl, pyrimidyl, pyrazinyl, pyridazinyl, oxazinyl, dioxinyl, thiazinyl, triazinyl, indolyl, isoindolyl, benzofuranyl, isobenzofuranyl, benzothiophenyl, isobenzothiophenyl, indazolyl, benzimidazolyl, benzoxazolyl, purinyl, benzodioxolyl, quinolinyl, isoquinolinyl, cinnolinyl, quinazolinyl, quinoxalinyl, preferably pyridinyl, pyrimidyl.

The term "COOalkyl" refers to a moiety —C(═O)—O— alkyl, wherein alkyl is as defined above.

The term "alkyloxyaryl" refers to a moiety alkyl-O-aryl-, wherein alkyl and aryl are as defined above.

The term "arylalkyl" refers to a moiety aryl-alkyl-, wherein alkyl and aryl are as defined above.

The term "arylalkyloxy" refers to a moiety aryl-alkyl-O—, wherein alkyl and aryl are as defined above.

The term "alkylcarbonyl" refers to a moiety alkyl-C(═O)—, wherein alkyl is as defined above.

The term "arylcarbonyl" refers to a moiety aryl-C(═O)—, wherein aryl is as defined above.

The term "arylalkylcarbonyl" refers to a moiety arylalkyl-C(═O)—, wherein arylalkyl is as defined above.

The term "alkylocyarylcarbonyl" refers to a moiety alkyloxyaryl-C(═O)—, wherein alkyloxyaryl is as defined above.

The term "formyl" refers to the moiety —C(═O)H.

The term "heteroarylalkyl" refers to a moiety heteroarylalkyl-, wherein alkyl and heteroaryl are as defined above.

The term "aminoalkyl" refers to a moiety H$_2$N-alkyl-, wherein alkyl is as defined above.

The term "solvate" is used herein to describe a compound in this invention that contains stoichiometric or sub-stoichiometric amounts of one or more pharmaceutically acceptable solvent molecule such as ethanol. The term "hydrate" refers to when the said solvent is water.

The term "prodrug" as used herein means the pharmacologically acceptable derivatives of compounds of the invention, such as for example amides, whose in vivo biotransformation product generates the biologically active drug. Prodrugs are generally characterized by increased bio-availability and are readily metabolized into biologically active compounds in vivo.

The term "predrug", as used herein, means any compound that will be modified to form a drug species, wherein the modification may take place either inside or outside of the body, and either before or after the predrug reaches the area of the body where administration of the drug is indicated.

The term "treatment" refers to both therapeutic treatment and prophylactic or preventative measures; wherein the object is to prevent or slow down (lessen) cystic fibrosis. Those in need of treatment include those already with cystic fibrosis as well as those prone to have cystic fibrosis or those in whom cystic fibrosis is to be prevented. A subject or mammal is successfully "treated" for cystic fibrosis if, after receiving a therapeutic amount of a compound according to the present invention, the patient shows observable and/or measurable reduction in or absence of one or more of the following: relief to some extent, one or more of the symptoms associated cystic fibrosis; reduced morbidity and mortality, and improvement in quality of life issues. The above parameters for assessing successful treatment and improvement in the disease are readily measurable by routine procedures familiar to a physician.

The term "subject" refers to a mammal, preferably a human. In one embodiment, the subject is a man. In another embodiment, the subject is a woman. In one embodiment, a subject may be a "patient", i.e. a warm-blooded animal, more preferably a human, who/which is awaiting the receipt of, or is receiving medical care or was/is/will be the object of a medical procedure, or is monitored for the development of cystic fibrosis. In one embodiment, the subject is an adult (for example a subject above the age of 18). In another embodiment, the subject is a child (for example a subject below the age of 18). In one embodiment the compound of the invention is administered to a human patient in need thereof.

The term "therapeutically effective amount" means level or amount of compound necessary and sufficient for slowing down or stopping the progression, aggravation, or deterioration of one or more symptoms of cystic fibrosis; alleviating the symptoms of cystic fibrosis; curing cystic fibrosis.

The term "pharmaceutically acceptable excipient" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. A pharmaceutically acceptable carrier or excipient refers to a non-toxic solid, semi-solid or liquid filler, diluent, encapsulating material or formulation auxiliary of any type. For human administration, preparations should meet sterility, pyrogenicity, general safety and purity standards as required by FDA Office of Biologics standards.

DETAILED DESCRIPTION

Compounds

The present invention relates to compounds of formula A

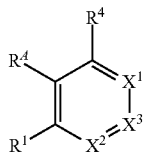

(A)

and pharmaceutically acceptable enantiomers, salts, solvates and prodrugs thereof, wherein:
- $X^1$ represents N or CH;
- $X^2$ represents N or CH;
- $X^3$ represents C—$R^5$ or N—$R^B$, wherein $R^B$ is either absent of represents an oxygen atom;
  provided that at least one of $X^1$, $X^2$ or $X^3$ represents N;
- $R^A$ represents H or $X^4R^2R^3$ wherein $X^4$ represents N or CH;
- $R^1$ represents H; $NR^6R^7$; halo; $OR^6$; or $SO_nR^8$ wherein n is 0, 1, 2 or 3 and wherein
- $R^8$ represents H, $NH_2$, alkyl, optionally substituted aryl, heteroaryl, arylalkyl, heteroarylalkyl or alkyloxyaryl;
- $R^2$ and $R^3$ represent each independently H, O, alkyl, aryl, heteroaryl, arylalkyl, heteroarylalkyl, alkyloxyaryl, formyl, alkylcarbonyl, arylcarbonyl, heteroarylcarbonyl, arylalkylcarbonyl, heteroarylalkylcarbonyl or alkyloxyarylcarbonyl;

or when $R^A$ is $X^4R^2R^3$ and $R^1$ is $NR^6R^7$, then $R^2$, $R^3$ and $R^7$ are linked together and form the link =X— between the two nitrogen atoms, wherein X represent $CR^9$ or N, wherein $R^9$ represents H; OH; halo; C1-C4-alkyl; $SO_mR^{10}$ wherein m is 0, 1, 2 or 3 and wherein $R^{10}$ represents H, $NH_2$ or C1-C4-alkyl; or $NR^{11}R^{12}$ wherein $R^{11}$ and $R^{12}$ represent each independently H or C1-C4-alkyl;

- $R^4$ represents H; halo; alkyl; optionally substituted aryl; $NH_2$; alkylthio ether; OH; alkyloxy; aryloxy; arylalkyloxy; alkyloxyarylalkyl; heteroaryloxy; —O—CO—NH—$CHPh_2$; $NR^{13}R^{14}$ wherein $R^{13}$ and $R^{14}$ represent each independently an alkyl group; —NH-Ph wherein the phenyl group is optionally substituted by hydroxyalkyl, alkyl carbonyl or $CONH_2$; —NH—$CH_2$—$R^{15}$ wherein $R^{15}$ represents COOH, —COOalkyl, alkyloxyaryl, arylalkyl or heteroarylalkyl; —NH—$CHR^{16}R^{17}$ wherein $R^{16}$ represents hydroxymethyl or methyl and $R^{17}$ represents hydroxymethyl, COOH, COOalkyl, COOarylalkyl or COOalkylaryl; or —NHCO—$R^{18}$ wherein $R^{18}$ represents H, alkyl, aryl, heteroaryl, arylalkyl, heteroarylalkyl or alkyloxyaryl;

- $R^5$ represents H; halo; alkyl; optionally substituted aryl; OH; alkyloxy; aryloxy; arylalkyloxy; heteroarylalkyloxy; $SO_pR^{19}$ wherein p is 0, 1, 2 or 3 and wherein $R^{19}$ represents H, $NH_2$, alkyl aryl, heteroaryl, arylalkyl, heteroarylalkyl or alkyloxyaryl; or $NR^{20}R^{21}$ wherein $R^{20}$ and $R^{21}$ represents each independently a group selected from H, alkyl, arylalkyl, heteroarylalkyl, alkoxyarylalkyl, haloarylalkyl, alkoxyarylalkyl, aryl, heteroaryl, alkyloxyaryl, aminocarbonylaryl, formyl, alkylcarbonyl, arylcarbonyl, heteroarylcarbonyl, arylalkylcarbonyl, heteroarylalkylcarbonyl and alkyloxyarylcarbonyl;

- $R^6$ and $R^7$ represent each independently H; alkyl; arylalkyl wherein the aryl group is optionally substituted by one or more group selected from halo, aminocarbonyl and carboxyl; heteroarylalkyl; heteroarylaminoalkyl wherein the heteroaryl group is optionally substituted by one or more group selected from halo and $NH_2$; aminoalkyl; heterocycloalkyl; heteroaryl; aryl optionally substituted by one or more group selected from halo, alkyl, arylalkyloxyalkyl, alkylcarbonylamino, alkyloxy, hydroxymethyl, $CONH_2$, COOH, COOalkyl, $SO_3H$ and $SO_2NH_2$.

According to a specific embodiment, $R^A$ represents $NR^2R^3$. In a specific embodiment, $R^A$ represents $NO_2$.

In a first embodiment, $X^1$ and $X^2$ represent both N and $X^3$ represents C—$R^5$ and the invention relates to a compound of formula A-I

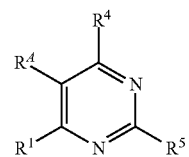

(A-I)

and pharmaceutically acceptable enantiomers, salts, solvates and prodrugs thereof, wherein $R^A$, $R^1$, $R^4$ and $R^5$ are as defined in formula A.

According to one embodiment, compounds of Formula A-I are those of Formula I

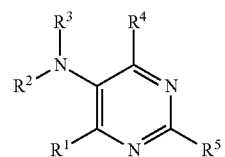

(I)

and pharmaceutically acceptable enantiomers, salts, solvates and prodrugs thereof, wherein:
- $R^1$ represents H; $NR^6R^7$; halo; $OR^6$; or $SO_nR^8$ wherein n is 0, 1, 2 or 3 and wherein $R^8$ represents H, $NH_2$, alkyl, optionally substituted aryl, heteroaryl, arylalkyl, heteroarylalkyl or alkyloxyaryl;
- $R^2$ and $R^3$ represent each independently H, O, alkyl, aryl, heteroaryl, arylalkyl, heteroarylalkyl, alkyloxyaryl, formyl, alkylcarbonyl, arylcarbonyl, heteroarylcarbonyl, arylalkylcarbonyl, heteroarylalkylcarbonyl or alkyloxyarylcarbonyl;

or when $R^1$ is $NR^6R^7$, then $R^2$, $R^3$ and $R^7$ are linked together and form the link =X— between the two nitrogen atoms, wherein X represent $CR^9$ or N, wherein $R^9$ represents H; OH; halo; C1-C4-alkyl; $SO_mR^{10}$ wherein m is 0, 1, 2 or 3 and wherein $R^{10}$ represents H, $NH_2$ or C1-C4-alkyl; or $NR^{11}R^{12}$ wherein $R^{11}$ and $R^{12}$ represent each independently H or C1-C4-alkyl;

- $R^4$ represents H; halo; alkyl; optionally substituted aryl; $NH_2$; alkylthio ether; OH; alkyloxy; aryloxy; arylalkyloxy; alkyloxyarylalkyl; heteroaryloxy; —O—CO—NH—$CHPh_2$; $NR^{13}R^{14}$ wherein $R^{13}$ and $R^{14}$ represent each independently an alkyl group; —NH-Ph wherein the phenyl group is optionally substituted by hydroxyalkyl, alkyl carbonyl or $CONH_2$; —NH—$CH_2$—$R^{15}$ wherein $R^{15}$ represents COOH, —COOalkyl, alkyloxyaryl, arylalkyl or heteroarylalkyl; —NH—$CHR^{16}R^{17}$ wherein $R^{16}$ represents hydroxymethyl or methyl and $R^{17}$ represents hydroxymethyl, COOH, COOalkyl, COOarylalkyl or COOalkylaryl; or —NHCO—$R^{18}$ wherein $R^{18}$ represents H, alkyl, aryl, heteroaryl, arylalkyl, heteroarylalkyl or alkyloxyaryl;

- $R^5$ represents H; halo; alkyl; optionally substituted aryl; OH; alkyloxy; aryloxy; arylalkyloxy; heteroarylalkyloxy; $SO_pR^{19}$ wherein p is 0, 1, 2 or 3 and wherein $R^{19}$ represents H, $NH_2$, alkyl aryl, heteroaryl, arylalkyl, heteroarylalkyl or alkyloxyaryl; or $NR^{20}R^{21}$ wherein $R^{20}$ and $R^{21}$ represents each independently a group selected from H, alkyl, arylalkyl, heteroarylalkyl, alkoxyarylalkyl, haloarylalkyl, alkoxyarylalkyl, aryl, heteroaryl, alkyloxyaryl, aminocarbonylaryl, formyl, alkylcarbonyl, arylcarbonyl, heteroarylcarbonyl, arylalkylcarbonyl, heteroarylalkylcarbonyl and alkyloxyarylcarbonyl;

- $R^6$ and $R^7$ represent each independently H; alkyl; arylalkyl wherein the aryl group is optionally substituted by one or more group selected from halo, aminocarbonyl and carboxyl; heteroarylalkyl; heteroarylaminoalkyl wherein the heteroaryl group is optionally substituted by one or more group selected from halo and $NH_2$; aminoalkyl; heterocycloalkyl; heteroaryl; aryl optionally substituted by one or more group selected from halo, alkyl, arylalkyloxyalkyl, alkylcarbonylamino, alkyloxy, hydroxymethyl, $CONH_2$, COOH, COOalkyl, $SO_3H$ and $SO_2NH_2$.

Especially, the present invention relates to compounds of general Formula I

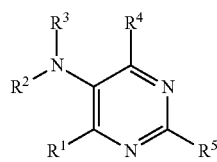

(I)

and pharmaceutically acceptable enantiomers, salts, solvates and prodrugs thereof, wherein:

$R^1$ represents $NR^6R^7$; halo; $OR^6$; or $SO_nR^8$ wherein n is 0, 1, 2 or 3 and wherein $R^8$ represents H, $NH_2$, alkyl, aryl, heteroaryl, arylalkyl, heteroarylalkyl or alkyloxyaryl; preferably $R^1$ represents halo or $NR^6R^7$;

when $R^1$ is halo, $SO_nR^8$ or $OR^6$, then
$R^2$ and $R^3$ both represent H;

when $R^1$ is $NR^6R^7$, then
$R^2$ and $R^3$ represent each independently H, alkyl, aryl, heteroaryl, arylalkyl, heteroarylalkyl, alkyloxyaryl, formyl, alkylcarbonyl, arylcarbonyl, heteroarylcarbonyl, arylalkylcarbonyl, heteroarylalkylcarbonyl, alkyloxyarylcarbonyl; preferably $R^2$ and $R^3$ represent each independently H, alkyl, aryl, heteroaryl, arylalkyl, heteroarylalkyl, alkyloxyaryl, formyl, alkylcarbonyl, arylcarbonyl, heteroarylcarbonyl, arylalkylcarbonyl, heteroarylalkylcarbonyl, alkyloxyarylcarbonyl, and $R^7$ represent H; more preferably $R^2$ and $R^3$ represent both H and $R^7$ represents H;

or $R^2$, $R^3$ and $R^7$ are linked together and form the link =X— between the two nitrogen atoms, wherein X represent $CR^9$ or N, wherein $R^9$ represents H; OH; halo; C1-C4-alkyl; $SO_mR^{10}$ wherein m is 0, 1, 2 or 3 and wherein $R^{10}$ represents H, $NH_2$, C1-C4-alkyl; $NR^{11}R^{12}$ wherein $R^{11}$ and $R^{12}$ represent each independently H, C1-C4-alkyl; preferably $R^9$ represents H;

$R^4$ represents H; halo; $NH_2$; OH; alkyloxy; aryloxy; heteroaryloxy; —O—CO—NH—$CHPh_2$; $NR^{13}R^{14}$ wherein $R^{13}$ and $R^{14}$ represent each independently an alkyl group, preferably $R^{13}$ and $R^{14}$ represent both ethyl; —NH-Ph-$CONH_2$; —NH—$CH_2$—$R^{15}$ wherein $R^{15}$ represents COOH, —COOalkyl, alkyloxyaryl, arylalkyl, heteroarylalkyl, preferably $R^{15}$ represents COOH, —COOtBu, methoxyphenyl, phenylpropyl; —NH—$CHR^{16}R^{17}$ wherein $R^{16}$ represents hydroxymethyl or methyl and $R^{17}$ represents hydroxymethyl, COOH, COOalkyl, preferably $R^{17}$ represents hydroxymethyl, COOH, COOtBu; —NHCO—$R^{18}$ wherein $R^{18}$ represents H, alkyl, aryl, heteroaryl, arylalkyl, heteroarylalkyl, alkyloxyaryl; preferably $R^4$ represents Cl, $NH_2$, OH, —O—CO—NH—$CHPh_2$, $NEt_2$, —NH-p-Ph-$CONH_2$; —NH—$CH_2$—$R^{15}$ wherein $R^{15}$ represents COOH, —COOtBu, p-methoxyphenyl, phenylpropyl; —NH—$CHR^{16}R^{17}$ wherein $R^{16}$ represents hydroxymethyl or methyl and $R^{17}$ represents hydroxymethyl, COOH, COOtBu; more preferably $R^4$ represents Cl, $NH_2$, —NH—$CHR^{16}R^{17}$ wherein $R^{16}$ represents methyl and $R^{17}$ represents COOH;

$R^5$ represents H; halo; alkyl; OH; alkyloxy; aryloxy; arylalkyloxy, heteroarylalkyloxy; $SO_pR^{19}$ wherein p is 0, 1, 2 or 3 and wherein $R^{19}$ represents H, $NH_2$, alkyl aryl, heteroaryl, arylalkyl, heteroarylalkyl, alkyloxyaryl; $NR^{20}R^{21}$ wherein $R^{20}$ and $R^{21}$ represents each independently a group selected from H, alkyl, arylalkyl, heteroarylalkyl, aryl, heteroaryl, alkyloxyaryl, formyl, alkylcarbonyl, arylcarbonyl, heteroarylcarbonyl, arylalkylcarbonyl, heteroarylalkylcarbonyl, alkyloxyarylcarbonyl; preferably $R^5$ represents H, Cl, methyl, phenylpropyloxy, phenylethyloxy, $NH_2$, phenylpropylamino, phenylethylamino, methylcarbonylamino; more preferably $R^5$ represents H, Cl, $NH_2$, phenyl-n-propylamino;

$R^6$ and $R^7$ represent each independently H; arylalkyl wherein the aryl group is optionally substituted by one or more group selected from halo and carboxyl; heteroarylalkyl; heteroarylaminoalkyl wherein the heteroaryl group is optionally substituted by one or more group selected from halo and $NH_2$; aminoalkyl; aryl substituted by one or more group selected from alkyloxy, hydroxymethyl, $CONH_2$, COOH, COOalkyl, $SO_3H$, $SO_2NH_2$; preferably $R^6$ represents H, phenylalkyl wherein the phenyl group is optionally substituted by one or more group selected from fluoro and carboxyl and wherein the alkyl is preferably selected from methyl, ethyl, n-propyl, n-butyl; heteroarylalkyl wherein the heteroaryl is preferably pyridine and wherein the alkyl group is preferably selected from methyl and ethyl; heteroarylaminoalkyl wherein the heteroaryl group is optionally substituted by one or more group selected from Cl and $NH_2$ and wherein the heteroaryl is preferably pyrimidine and wherein the alkyl group is preferably selected from ethyl and n-propyl; amino-n-propyl; phenyl substituted in para or meta, preferably in para, by one or more group selected from hydroxymethyl, $CONH_2$, COOH, COOMe and $SO_3H$; more preferably $R^6$ represents H, phenyl-n-propyl, phenyl substituted in para by hydroxymethyl or $CONH_2$ and $R^7$ represents H;

provided that:
$R^4$ and $R^5$ are not both H;
$R^5$ and $R^6$ are not both H;
$R^4$ and $R^5$ are not both Cl.

In a specific embodiment, compound of Formula A, especially compound of Formula I is not
4-(2-amino-6-hydroxy-9H-purin-9-yl)benzamide;
$N^2$-2-phenethyl-9H-purine-2,6-diamine;
9-benzyl-9H-purin-6-amine;
9-(3-phenylpropyl)-9H-purin-6-amine;
4-(2-amino-6-hydroxy-9H-purin-9-yl)benzoic acid;
9-benzyl-2-chloro-N-(4-methoxybenzyl)-9H-purin-6-amine;
4,6-dichloropyrimidin-5-amine;
4,6-dichloropyrimidine-2,5-diamine;
2-chloro-9H-purin-6-amine;
2-amino-9H-purin-6-ol;
3-(2-amino-6-hydroxy-9H-purin-9-yl)benzoic acid.

In a specific embodiment, compound of Formula A, especially compound of Formula I is not
9-benzyl-2-chloro-N-(4-methoxybenzyl)-9H-purin-6-amine;
4,6-dichloropyrimidin-5-amine;
4,6-dichloropyrimidine-2,5-diamine.

In a specific embodiment, compound of Formula A is not
4-chloro-N-(4,5-dihydro-1H-imidazol-2-yl)-6-methoxy-2-methylpyrimidin-5-amine;
2-((6-(benzylamino)-9-isopropyl-9H-purin-2-yl)amino)butan-1-ol;
2-((6-(benzylamino)-9-methyl-9H-purin-2-yl)amino)ethanol.

In a specific embodiment, compound of Formula A, especially compound of Formula I is not
3-((5-amino-2-((4-methoxyphenyl)(methyl)amino)pyrimidin-4-yl)amino)benzenesulfonamide;
4-((5-amino-2-((4-methoxyphenyl)(methyl)amino)pyrimidin-4-yl)amino)benzenesulfonamide;
3-((5-amino-2-((3-methoxyphenyl)(methyl)amino)pyrimidin-4-yl)amino)benzenesulfonamide;
4-((5-amino-2-((3-methoxyphenyl)(methyl)amino)pyrimidin-4-yl)amino)benzenesulfonamide.

In one embodiment, preferred compounds of Formula I are those of Formula Ia

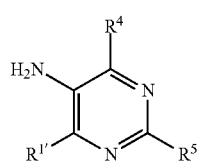

(Ia)

and pharmaceutically acceptable enantiomers, salts, solvates and prodrugs thereof, wherein $R^4$ and $R^5$ are as defined in Formula I and $R^{1'}$ represents halo, $SO_nR^8$ or $OR^6$ wherein $R^6$ and $R^8$ are as defined in Formula I, preferably $R^{1'}$ represents halo, more preferably $R^{1'}$ represents Cl.

In a specific embodiment, preferred compounds of Formula Ia are those wherein:
$R^{1'}$ represents halo, preferably Cl;
$R^4$ represents halo, preferably Cl;
$R^5$ represents H or $NH_2$.

In one embodiment, preferred compounds of Formula I are those of Formula Ib

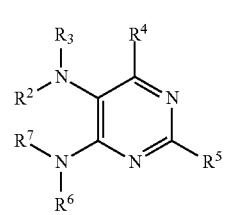

(Ib)

and pharmaceutically acceptable enantiomers, salts, solvates and prodrugs thereof, wherein $R^4$, $R^5$, $R^6$ and $R^7$ are as defined above in Formula I.

$R^2$ and $R^3$ represent each independently H, alkyl, aryl, heteroaryl, arylalkyl, heteroarylalkyl, alkyloxyaryl, formyl, alkylcarbonyl, arylcarbonyl, heteroarylcarbonyl, arylalkylcarbonyl, heteroarylalkylcarbonyl, alkyloxyarylcarbonyl; preferably $R^2$ and $R^3$ represent each independently H, alkyl, aryl, heteroaryl, arylalkyl, heteroarylalkyl, alkyloxyaryl, formyl, alkylcarbonyl, arylcarbonyl, heteroarylcarbonyl, arylalkylcarbonyl, heteroarylalkylcarbonyl, alkyloxyarylcarbonyl, and $R^7$ represent H; more preferably $R^2$ and $R^3$ represent both H and $R^7$ represents H;

or $R^2$, $R^3$ and $R^7$ are linked together and form the link =X— between the two nitrogen atoms, wherein X represent $CR^9$ or N, wherein $R^9$ represents H; OH; halo; C1-C4-alkyl; $SO_mR^{10}$ wherein m is 0, 1, 2 or 3 and wherein $R^{10}$ represents H, $NH_2$, C1-C4-alkyl; $NR^{11}R^{12}$ wherein $R^{11}$ and $R^{12}$ represent each independently H, C1-C4-alkyl; preferably $R^9$ represents H.

In one embodiment, preferred compounds of Formula Ib are those of Formula Ib-1

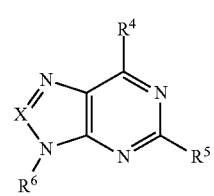

(Ib-1)

and pharmaceutically acceptable enantiomers, salts, solvates and prodrugs thereof, wherein X, $R^4$, $R^5$ and $R^6$ are as defined above in Formula I.

In one embodiment, preferred compounds of Formula Ib-1 are those of Formula Ib-1a

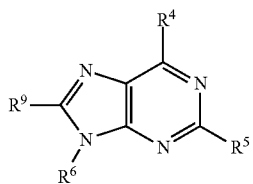

(Ib-1a)

and pharmaceutically acceptable enantiomers, salts, solvates and prodrugs thereof, wherein $R^4$, $R^5$, $R^6$ and $R^9$ are as defined above in Formula I.

In one embodiment, preferred compounds of Formula Ib-1a are those of Formula Ib-1a1

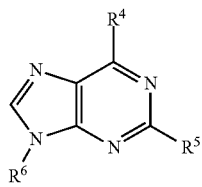

(Ib-1a1)

and pharmaceutically acceptable enantiomers, salts, solvates and prodrugs thereof, wherein $R^4$, $R^5$ and $R^6$ are as defined above in Formula I.

In a specific embodiment, preferred compounds of Formula Ib-1a1 are those wherein:

- $R^4$ represents halo, $NH_2$, OH, —O—CO—NH—$CHPh_2$, $NR^8R^9$ wherein $R^8$ and $R^9$ represent each independently an alkyl group, preferably $R^8$ and $R^9$ represent both ethyl; —NH-Ph-$CONH_2$; —NH—$CH_2$—$R^{10}$ wherein $R^{10}$ represents COOH, —COOalkyl, alkyloxyaryl, arylalkyl, preferably $R^{10}$ represents COOH, —COOtBu, methoxyphenyl, phenylpropyl; —NH—$CHR^{11}R^{12}$ wherein $R^{11}$ represents hydroxymethyl or methyl and $R^{12}$ represents hydroxymethyl, COOH, COOalkyl, preferably $R^{12}$ represents hydroxymethyl, COOH, COOtBu; preferably $R^4$ represents Cl, $NH_2$, OH, —O—CO—NH—$CHPh_2$, $NEt_2$, —NH-p-Ph-$CONH_2$; —NH—$CH_2$—$R^{10}$ wherein $R^{10}$ represents COOH, —COOtBu, p-methoxyphenyl, phenylpropyl; —NH—$CHR^{11}R^{12}$ wherein $R^{11}$ represents hydroxymethyl or methyl and $R^{12}$ represents hydroxymethyl, COOH, COOtBu;
- $R^5$ represents H, halo, arylalkyloxy, $NH_2$, $NHR^{13}$ wherein $R^{13}$ represents a group selected from arylalkyl and alkylcarbonyl; preferably $R^5$ represents H, Cl, phenylpropyloxy, phenylethyloxy, $NH_2$, phenylpropylamino, methylcarbonylamino;
- $R^6$ represents H, arylalkyl, aryl substituted by one or more group selected from hydroxymethyl, $CONH_2$, COOH and COOalkyl; preferably $R^6$ represents H, phenylalkyl wherein the alkyl is preferably selected from methyl and n-propyl; phenyl substituted in para or meta, preferably in para, by one group selected from hydroxymethyl, $CONH_2$, COOH and COOMe and $SO_3H$.

In one embodiment, preferred compounds of Formula Ib-1 are those of Formula Ib-1b

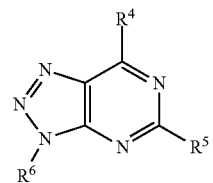

(Ib-1b)

and pharmaceutically acceptable enantiomers, salts, solvates and prodrugs thereof, wherein $R^4$, $R^5$ and $R^6$ are as defined above in Formula I.

In a specific embodiment, preferred compounds of Formula Ib-1b are those wherein:

- $R^4$ represents halo or —NH—$CH_2$—$R^{10}$ wherein $R^{10}$ represents COOH, —COOalkyl, alkyloxyaryl, arylalkyl, preferably $R^{10}$ represents COOH, —COOtBu, methoxyphenyl, phenylpropyl; preferably $R^4$ represents Cl or —NH—$CH_2$—COOtBu;
- $R^5$ represents H or $NH_2$;
- $R^6$ represents an aryl group substituted by one or more group selected from hydroxymethyl, $CONH_2$, COOH, COOalkyl and $SO_3H$; preferably $R^6$ represents a phenyl substituted in para or meta, preferably in para, by one group selected from hydroxymethyl, $CONH_2$, COOH, COOMe and $SO_3H$; more preferably $R^6$ represents phenyl substituted in para by $CONH_2$.

In one embodiment, preferred compounds of Formula I are those of Formula Ib-2

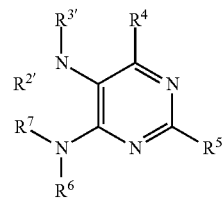

(Ib-2)

and pharmaceutically acceptable enantiomers, salts, solvates and prodrugs thereof, wherein $R^{2'}$ and $R^{3'}$ represent each independently H, alkyl, aryl, heteroaryl, arylalkyl, heteroarylalkyl, alkyloxyaryl, formyl, alkylcarbonyl, arylcarbonyl, heteroarylcarbonyl, arylalkylcarbonyl, heteroarylalkylcarbonyl, alkyloxyarylcarbonyl;

$R^4$, $R^5$, $R^6$ and $R^7$ are as defined above in Formula I.

In a preferred embodiment, in Formula Ib, $R^{2'}$ and $R^{3'}$ represent each independently H, alkyl, aryl, heteroaryl, arylalkyl, heteroarylalkyl, alkyloxyaryl, formyl, alkylcarbonyl, arylcarbonyl, heteroarylcarbonyl, arylalkylcarbonyl, heteroarylalkylcarbonyl, alkyloxyarylcarbonyl, and $R^7$ represent H; more preferably $R^{2'}$ and $R^{3'}$ represent both H and $R^7$ represents H.

In one embodiment, preferred compounds of Formula Ib-2 are those of Formula Ib-2a

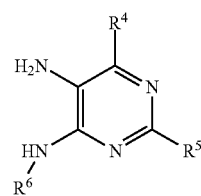

(Ib-2a)

and pharmaceutically acceptable enantiomers, salts, solvates and prodrugs thereof, wherein $R^4$, $R^5$ and $R^6$ are as defined above in Formula I.

In a specific embodiment, preferred compounds of Formula Ib-2a are those wherein:

- $R^4$ represents halo or —NH-Ph-CONH$_2$; preferably $R^4$ represents Cl or —NH-Ph-CONH$_2$; more preferably $R^4$ represents Cl:
- $R^5$ represents H, alkyl, NH$_2$, preferably $R^5$ represents H, methyl or NH$_2$; more preferably $R^5$ represents H;
- $R^6$ represents arylalkyl wherein the aryl group is optionally substituted by one or more group selected from halo and carboxyl heteroarylalkyl; heteroarylaminoalkyl wherein the heteroaryl group is optionally substituted by one or more group selected from halo and NH$_2$; aminoalkyl; aryl substituted by one or more group selected from hydroxymethyl, CONH$_2$, COOH, COOalkyl and SO$_3$H; preferably $R^6$ represents phenylalkyl wherein the phenyl group is optionally substituted by one group selected from fluoro and carboxyl and wherein the alkyl is preferably selected from methyl, ethyl, n-propyl, n-butyl; heteroarylalkyl wherein the heteroaryl is preferably pyridine and wherein the alkyl group is preferably selected from methyl and ethyl; heteroarylaminoalkyl wherein the heteroaryl group is optionally substituted by one or more group selected from Cl and NH$_2$ and wherein the heteroaryl is preferably pyrimidine and wherein the alkyl group is preferably selected from ethyl and n-propyl; amino-n-propyl; phenyl substituted in para or meta, preferably in para, by one group selected from CONH$_2$ and SO$_3$H.

In a second embodiment, $X^1$ represents N, $X^2$ represents CH and $X^3$ represents C—$R^5$, and the invention relates to a compound of formula A-II

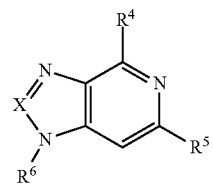
(A-II)

and pharmaceutically acceptable enantiomers, salts, solvates and prodrugs thereof, wherein $R^4$, $R^1$, $R^4$ and $R^5$ are as defined in formula A.

According to one embodiment, compounds of Formula A-II are those of Formula A-IIb

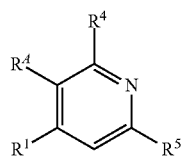
(A-IIb)

and pharmaceutically acceptable enantiomers, salts, solvates and prodrugs thereof, wherein $R^1$, $R^2$, $R^3$, $R^4$ and $R^5$ are as defined in formula A.

According to one embodiment, compounds of Formula A-IIb are those of Formula A-IIb-1

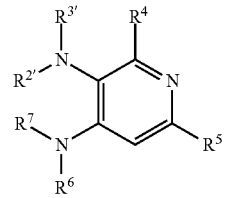
(A-IIb-1)

and pharmaceutically acceptable enantiomers, salts, solvates and prodrugs thereof, wherein $R^4$, $R^5$ and $R^6$ are as defined in formula A.

According to one embodiment, compounds of Formula A-IIb are those of Formula A-IIb-2

(A-IIb-2)

and pharmaceutically acceptable enantiomers, salts, solvates and prodrugs thereof, wherein $R^4$, $R^5$, $R^6$ and $R^7$ are as defined in formula A and $R^{2'}$ and $R^{3'}$ represent each independently H, O, alkyl, aryl, heteroaryl, arylalkyl, heteroarylalkyl, alkyloxyaryl, formyl, alkylcarbonyl, arylcarbonyl, heteroarylcarbonyl, arylalkylcarbonyl, heteroarylalkylcarbonyl, alkyloxyarylcarbonyl.

In a third embodiment, $X^1$ represents CH, $X^2$ represents N and $X^3$ represents C—$R^5$, and the invention relates to a compound of formula A-III

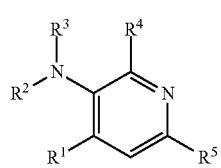
(A-III)

and pharmaceutically acceptable enantiomers, salts, solvates and prodrugs thereof, wherein $R^4$, $R^1$, $R^4$ and $R^5$ are as defined in formula A.

According to one embodiment, compounds of Formula A-III are those of Formula A-IIIb

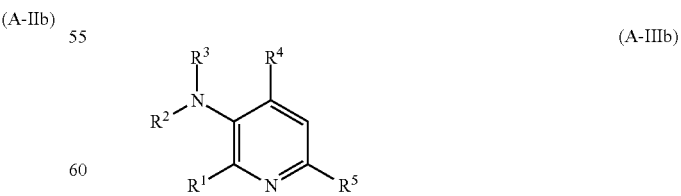
(A-IIIb)

and pharmaceutically acceptable enantiomers, salts, solvates and prodrugs thereof, wherein $R^1$, $R^2$, $R^3$, $R^4$ and $R^5$ are as defined in formula A.

According to one embodiment, compounds of Formula A-IIIb are those of Formula A-IIb-1

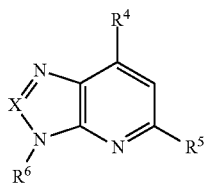

(A-IIIb-1)

and pharmaceutically acceptable enantiomers, salts, solvates and prodrugs thereof, wherein $R^4$, $R^5$ and $R^6$ are as defined in formula A.

According to one embodiment, compounds of Formula A-IIIb are those of Formula A-IIb-2

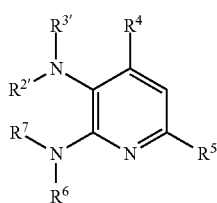

(A-IIIb-2)

and pharmaceutically acceptable enantiomers, salts, solvates and prodrugs thereof, wherein $R^4$, $R^5$, $R^6$ and $R^7$ are as defined in formula A and $R^{2'}$ and $R^{3'}$ represent each independently H, O, alkyl, aryl, heteroaryl, arylalkyl, heteroarylalkyl, alkyloxyaryl, formyl, alkylcarbonyl, arylcarbonyl, heteroarylcarbonyl, arylalkylcarbonyl, heteroarylalkylcarbonyl, alkyloxyarylcarbonyl.

In a fourth embodiment, $X^1$ and $X^2$ represent both CH and $X^3$ represents N—$R^B$, and the invention relates to a compound of formula A-IV

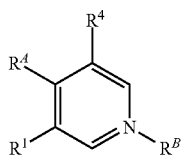

(A-IV)

and pharmaceutically acceptable enantiomers, salts, solvates and prodrugs thereof, wherein $R^A$, $R^B$, $R^1$ and $R^4$ are as defined in formula A.

According to one embodiment, compounds of Formula A-IV are those of Formula A-IVb

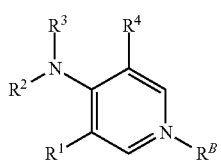

(A-IVb)

and pharmaceutically acceptable enantiomers, salts, solvates and prodrugs thereof, wherein $R^1$, $R^2$, $R^3$, $R^4$ and $R^B$ are as defined in formula A.

According to one embodiment, compounds of Formula A-IVb are those of Formula A-IVb-1

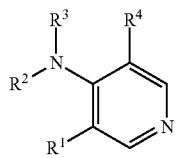

(A-IVb-1)

and pharmaceutically acceptable enantiomers, salts, solvates and prodrugs thereof, wherein $R^1$, $R^2$, $R^3$ and $R^4$ are as defined in formula A.

According to one embodiment, compounds of Formula A-IVb are those of Formula A-IVIb-2

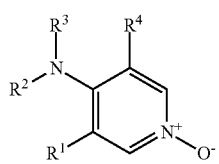

(A-IVb-2)

and pharmaceutically acceptable enantiomers, salts, solvates and prodrugs thereof, wherein $R^1$, $R^2$, $R^3$ and $R^4$ are as defined in formula A.

In another embodiment, in formula A, $R^A$ represents H, corresponding to a compound of formula B

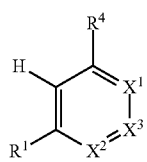

(B)

and pharmaceutically acceptable enantiomers, salts, solvates and prodrugs thereof, wherein $X^1$, $X^2$, $X^3$, $R^1$ and $R^4$ are as defined in formula A.

In another embodiment, in formula A, $R^A$ represents $X^4R^2R^3$, corresponding to a compound of formula C

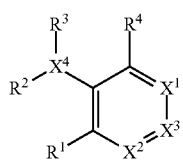

(C)

and pharmaceutically acceptable enantiomers, salts, solvates and prodrugs thereof, wherein $X^1$, $X^2$, $X^3$, $X^4$, $R^1$, $R^2$, $R^3$ and $R^4$ are as defined in formula A.

According to one embodiment, compounds of Formula C are those of Formula C1

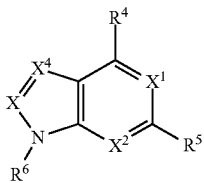

(C1)

and pharmaceutically acceptable enantiomers, salts, solvates and prodrugs thereof, wherein $X^1$, $X^2$, $X^4$, $X$, $R^4$, $R^5$ and $R^6$ are as defined in formula A.

According to one embodiment, compounds of Formula C1 are those of Formula C1a

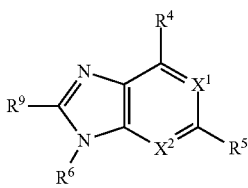

(C1a)

and pharmaceutically acceptable enantiomers, salts, solvates and prodrugs thereof, wherein $X^1$, $X^2$, $R^4$, $R^5$, $R^6$ and $R^9$ are as defined in formula A.

According to one embodiment, compounds of Formula C1 are those of Formula C1b

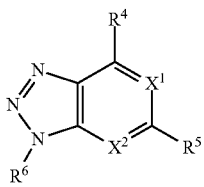

(C1b)

and pharmaceutically acceptable enantiomers, salts, solvates and prodrugs thereof, wherein $X^1$, $X^2$, $R^4$, $R^5$ and $R^6$ are as defined in formula A.

According to one embodiment, compounds of Formula C1 are those of Formula C1c

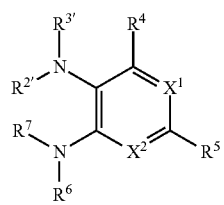

(C1c)

and pharmaceutically acceptable enantiomers, salts, solvates and prodrugs thereof, wherein $X^1$, $X^2$, $R^4$, $R^5$, $R^6$ and $R^9$ are as defined in formula A.

According to one embodiment, compounds of Formula C are those of Formula C2

(C2)

and pharmaceutically acceptable enantiomers, salts, solvates and prodrugs thereof, wherein $X^1$, $X^2$, $R^4$, $R^5$, $R^6$ and $R^7$ are as defined in formula A and $R^{2'}$ and $R^{3'}$ represent each independently H, O, alkyl, aryl, heteroaryl, arylalkyl, heteroarylalkyl, alkyloxyaryl, formyl, alkylcarbonyl, arylcarbonyl, heteroarylcarbonyl, arylalkylcarbonyl, heteroarylalkylcarbonyl, alkyloxyarylcarbonyl.

Particularly preferred compounds of Formula A of the invention are those listed in Table 1 hereafter.

TABLE 1

| Cpd no | Structure | Chemical name |
|--------|-----------|---------------|
| 1 | 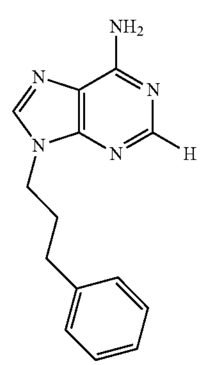 [SMILES: Nc1ncnc2c1ncn2CCCc1ccccc1] | 9-(3-phenylpropyl)-9H-purin-6-amine |

TABLE 1-continued

| Cpd no | Structure | Chemical name |
|---|---|---|
| 2 | 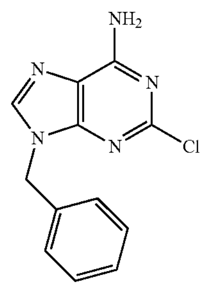 [SMILES: Nc1nc(Cl)nc2c1ncn2Cc1ccccc1] | 9-benzyl-2-chloro-9H-purin-6-amine |
| 3 | 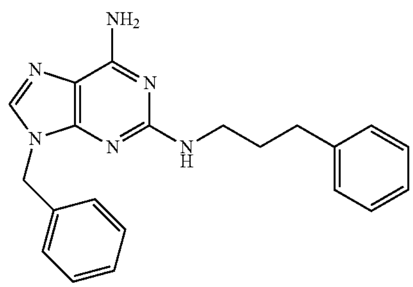 [SMILES: Nc1nc(NCCCc2ccccc2)nc2c1ncn2Cc1ccccc1] | 9-benzyl-$N^2$-(3-phenylpropyl)-9H-purine-2,6-diamine |
| 4 | 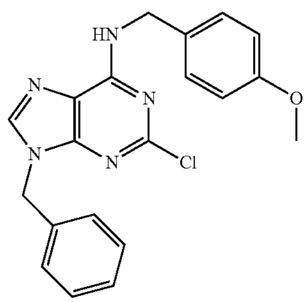 [SMILES: COc1ccc(CNc2nc(Cl)nc3c2ncn3Cc2ccccc2)cc1] | 9-benzyl-2-chloro-N-(4-methoxybenzyl)-9H-purin-6-amine |
| 5 | 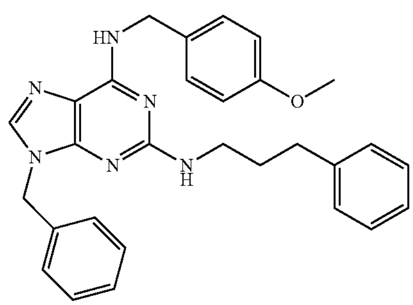 [SMILES: COc1ccc(CNc2nc(NCCCc3ccccc3)nc3c2ncn3Cc2ccccc2)cc1] | 9-benzyl-$N^6$-(4-methoxybenzyl)-$N^2$-(3-phenylpropyl)-9H-purine-2,6-diamine |
| 6 | 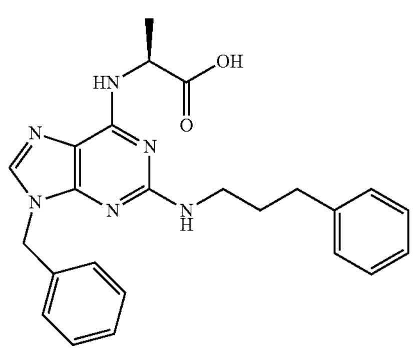 [SMILES: C[C@H](Nc1nc(NCCCc2ccccc2)nc2c1ncn2Cc1ccccc1)C(=O)O] | (S)-2-((9-benzyl-2-((3-phenylpropyl)amino)-9H-purin-6-yl)amino)propanoic acid |

TABLE 1-continued
| Cpd no | Structure | Chemical name |
|---|---|---|
| 7 | 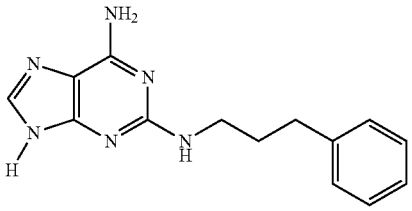 [SMILES: Nc1nc(NCCCc2ccccc2)nc2[nH]cnc12] | $N^2$-(3-phenylpropyl)-9H-purine-2,6-diamine |
| 8 | 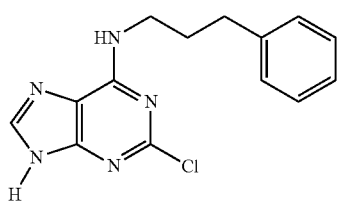 [SMILES: Clc1nc(NCCCc2ccccc2)c2nc[nH]c2n1] | 2-chloro-N-(3-phenylpropyl)-9H-purin-6-amine |
| 9 | 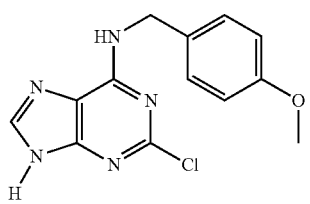 [SMILES: COc1ccc(CNc2nc(Cl)nc3[nH]cnc23)cc1] | 2-chloro-N-(4-methoxybenzyl)-9H-purin-6-amine |
| 10 | 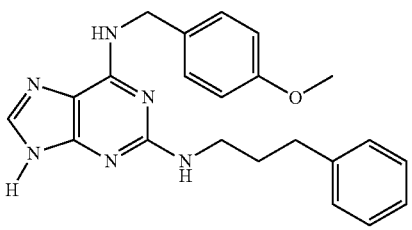 [SMILES: COc1ccc(CNc2nc(NCCCc3ccccc3)nc3[nH]cnc23)cc1] | $N^6$-(4-methoxybenzyl)-$N^2$-(3-phenylpropyl)-9H-purine-2,6-diamine |
| 11 | 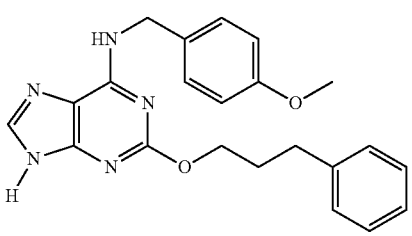 [SMILES: COc1ccc(CNc2nc(OCCCc3ccccc3)nc3[nH]cnc23)cc1] | N-(4-methoxybenzyl)-2-(3-phenylpropoxy)-9H-purin-6-amine |
| 12 | 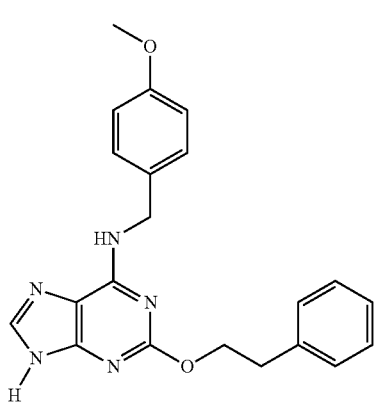 [SMILES: COc1ccc(CNc2nc(OCCc3ccccc3)nc3[nH]cnc23)cc1] | N-(4-methoxybenzyl)-2-phenethoxy-9H-purin-6-amine |

TABLE 1-continued

| Cpd no | Structure | Chemical name |
|---|---|---|
| 13 | 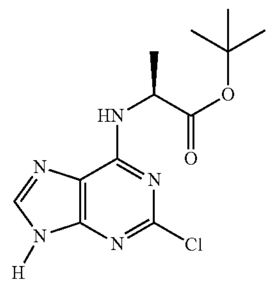 [SMILES: C[C@H](Nc1nc(Cl)nc2[nH]cnc12)C(=O)OC(C)(C)C] | (S)-tert-butyl 2-((2-chloro-9H-purin-6-yl)amino)propanoate |
| 14 | 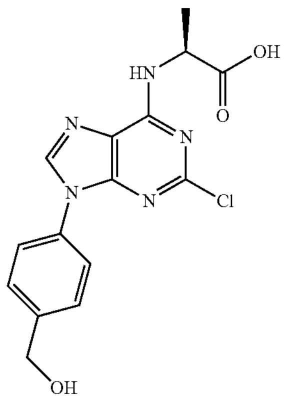 [SMILES: C[C@H](Nc1nc(Cl)nc2c1ncn2-c1ccc(CO)cc1)C(=O)O] | (S)-2-((2-chloro-9-(4-(hydroxymethyl)phenyl)-9H-purin-6-yl)amino)propanoic acid |
| 15 | 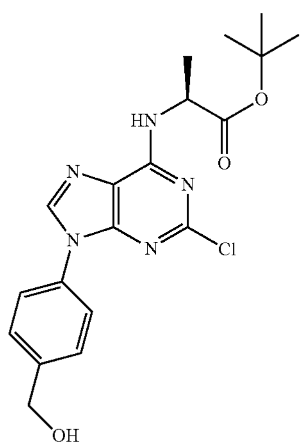 [SMILES: C[C@H](Nc1nc(Cl)nc2c1ncn2-c1ccc(CO)cc1)C(=O)OC(C)(C)C] | (S)-tert-butyl 2-((2-chloro-9-(4-(hydroxymethyl)phenyl)-9H-purin-6-yl)amino)propanoate |
| 16 | 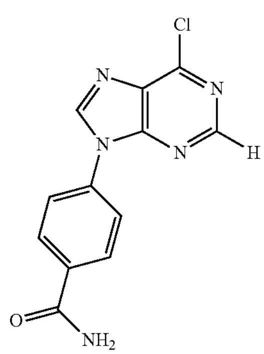 [SMILES: NC(=O)c1ccc(-n2cnc3c(Cl)ncnc32)cc1] | 4-(6-chloro-9H-purin-9-yl)benzamide |

TABLE 1-continued
| Cpd no | Structure | Chemical name |
|---|---|---|
| 17 | 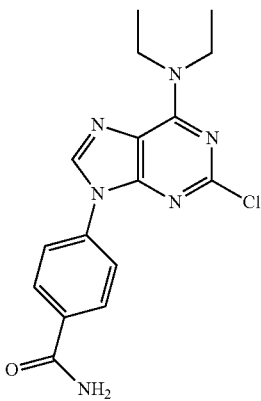 [SMILES: CCN(CC)c1nc(Cl)nc2c1ncn2-c1ccc(C(N)=O)cc1] | 4-(2-chloro-6-(diethylamino)-9H-purin-9-yl)benzamide |
| 18 | 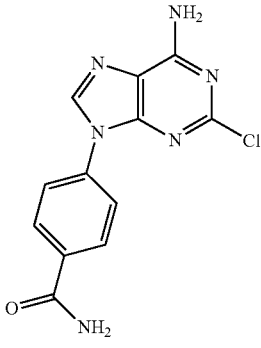 [SMILES: NC(=O)c1ccc(-n2cnc3c(N)nc(Cl)nc32)cc1] | 4-(6-amino-2-chloro-9H-purin-9-yl)benzamide |
| 19 | 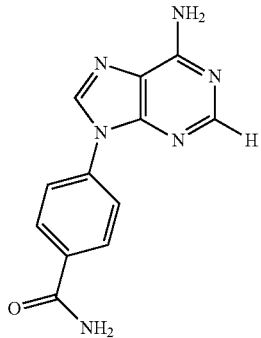 [SMILES: NC(=O)c1ccc(-n2cnc3c(N)ncnc32)cc1] | 4-(6-amino-9H-purin-9-yl)benzamide |
| 20 | 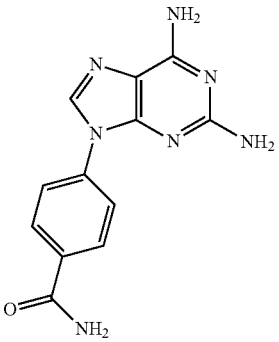 [SMILES: NC(=O)c1ccc(-n2cnc3c(N)nc(N)nc32)cc1] | 4-(2,6-diamino-9H-purin-9-yl)benzamide |

TABLE 1-continued
| Cpd no | Structure | Chemical name |
|---|---|---|
| 21 | 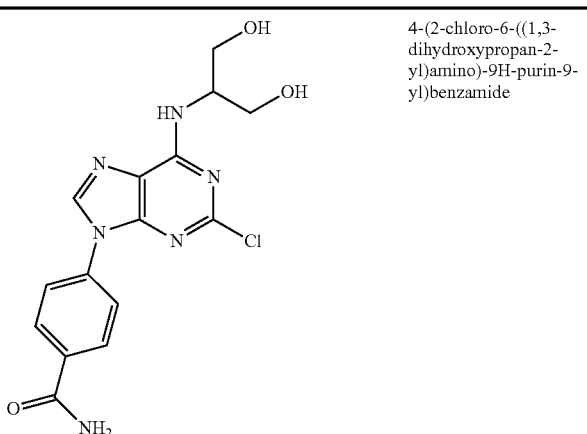 | 4-(2-chloro-6-((1,3-dihydroxypropan-2-yl)amino)-9H-purin-9-yl)benzamide |
| 22 | 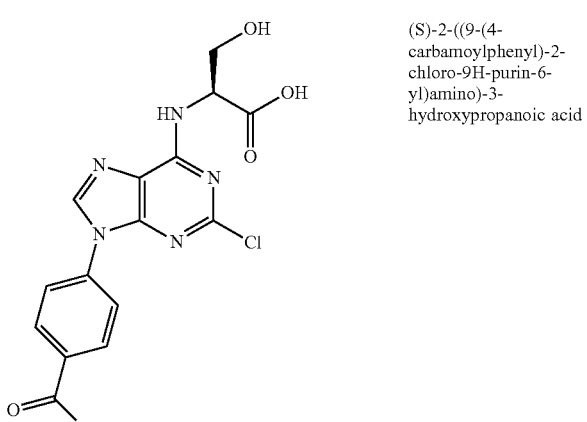 | (S)-2-((9-(4-carbamoylphenyl)-2-chloro-9H-purin-6-yl)amino)-3-hydroxypropanoic acid |
| 23 | 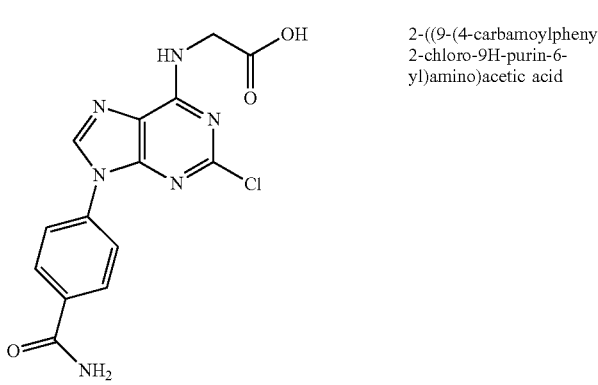 | 2-((9-(4-carbamoylphenyl)-2-chloro-9H-purin-6-yl)amino)acetic acid |
| 24 | 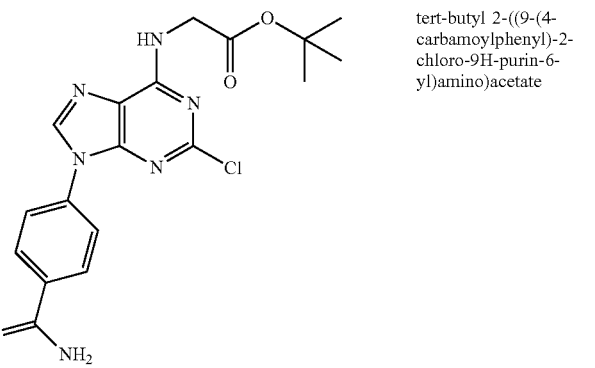 | tert-butyl 2-((9-(4-carbamoylphenyl)-2-chloro-9H-purin-6-yl)amino)acetate |

TABLE 1-continued

| Cpd no | Structure | Chemical name |
| --- | --- | --- |
| 25 | 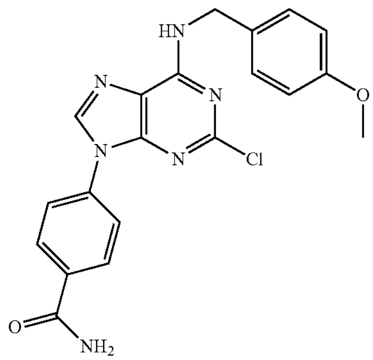 [SMILES: COc1ccc(CNc2nc(Cl)nc3c2ncn3-c2ccc(C(N)=O)cc2)cc1] | 4-(2-chloro-6-((4-methoxybenzyl)amino)-9H-purin-9-yl)benzamide |
| 26 | 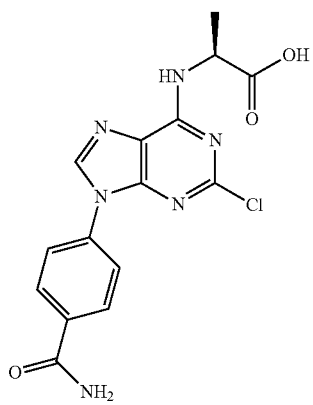 [SMILES: C[C@H](Nc1nc(Cl)nc2c1ncn2-c1ccc(C(N)=O)cc1)C(=O)O] | (S)-2-((9-(4-carbamoylphenyl)-2-chloro-9H-purin-6-yl)amino)propanoic acid |
| 27 | 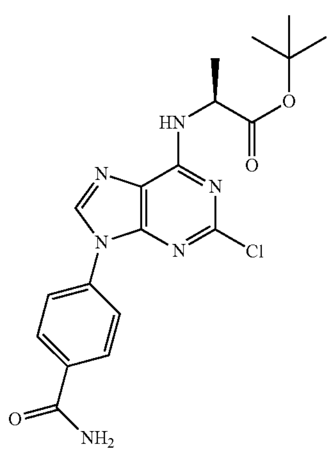 [SMILES: C[C@H](Nc1nc(Cl)nc2c1ncn2-c1ccc(C(N)=O)cc1)C(=O)OC(C)(C)C] | (S)-tert-butyl 2-((9-(4-carbamoylphenyl)-2-chloro-9H-purin-6-yl)amino)propanoate |

TABLE 1-continued

| Cpd no | Structure | Chemical name |
|---|---|---|
| 28 | 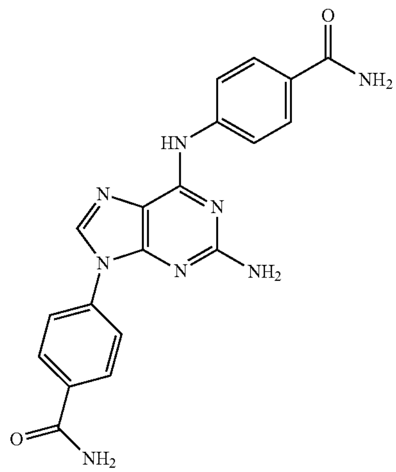 [SMILES: NC(=O)c1ccc(Nc2nc(N)nc3c2ncn3-c2ccc(C(N)=O)cc2)cc1] | 4-(2-amino-6-((4-carbamoylphenyl)amino)-9H-purin-9-yl)benzamide |
| 29 | 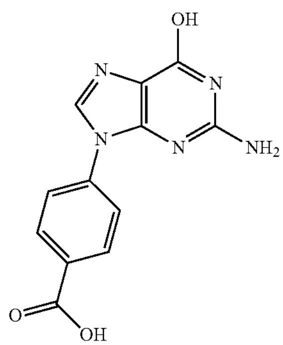 [SMILES: Nc1nc(O)c2ncn(-c3ccc(C(=O)O)cc3)c2n1] | 4-(2-amino-6-hydroxy-9H-purin-9-yl)benzoic acid |
| 30 | 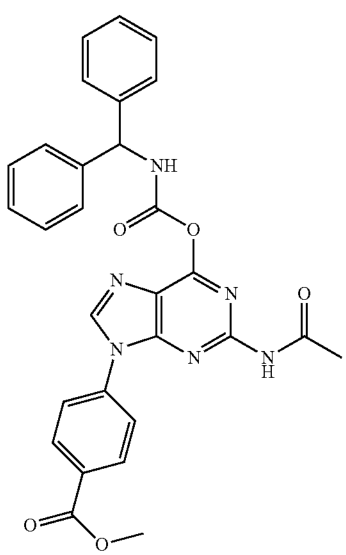 [SMILES: COC(=O)c1ccc(-n2cnc3c(OC(=O)NC(c4ccccc4)c4ccccc4)nc(NC(C)=O)nc32)cc1] | methyl 4-(2-acetamido-6-((benzhydrylcarbamoyl)oxy)-9H-purin-9-yl)benzoate |

TABLE 1-continued
| Cpd no | Structure | Chemical name |
|---|---|---|
| 31 | 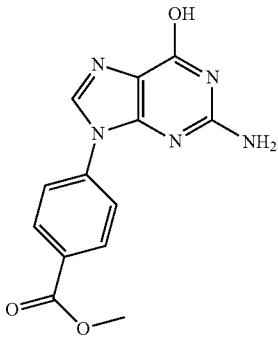 [SMILES: COC(=O)c1ccc(-n2cnc3c(O)nc(N)nc32)cc1] | methyl 4-(2-amino-6-hydroxy-9H-purin-9-yl)benzoate |
| 32 | 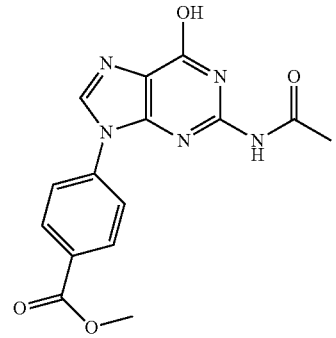 [SMILES: COC(=O)c1ccc(-n2cnc3c(O)nc(NC(C)=O)nc32)cc1] | methyl 4-(2-acetamido-6-hydroxy-9H-purin-9-yl)benzoate |
| 33 | 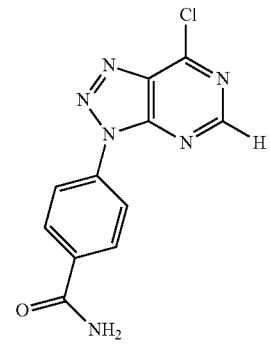 [SMILES: NC(=O)c1ccc(-n2nnc3c(Cl)ncnc32)cc1] | 4-(7-chloro-3H-[1,2,3]triazolo[4,5-d]pyrimidin-3-yl)benzamide |
| 34 | 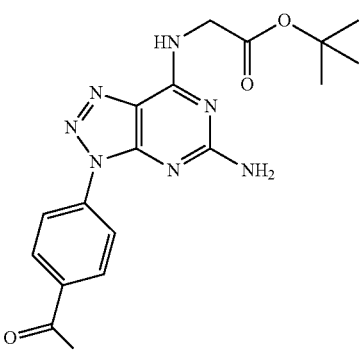 | tert-butyl 2-((5-amino-3-(4-carbamoylphenyl)-3H-[1,2,3]triazolo[4,5-d]pyrimidin-7-yl)amino)acetate |
| 35 | 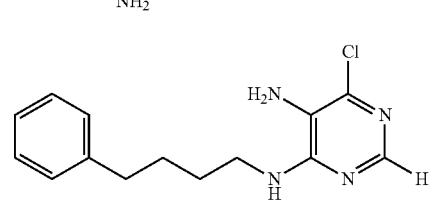 | 6-chloro-$N^4$-(4-phenylbutyl)pyrimidine-4,5-diamine |

TABLE 1-continued

| Cpd no | Structure | Chemical name |
| --- | --- | --- |
| 36 | 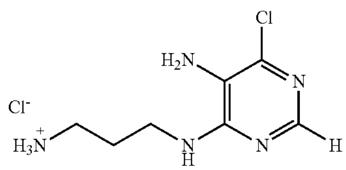 [SMILES: [Cl-] ; NCCCNc1ncnc(Cl)c1N] | 3-((5-amino-6-chloropyrimidin-4-yl)amino)propan-1-aminium chloride |
| 37 | 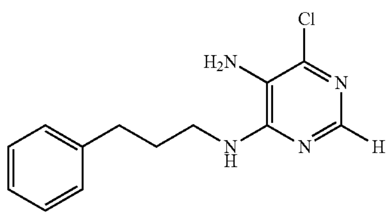 [SMILES: Nc1c(Cl)ncnc1NCCCc1ccccc1] | 6-chloro-$N^4$-(3-phenylpropyl)pyrimidine-4,5-diamine |
| 38 | 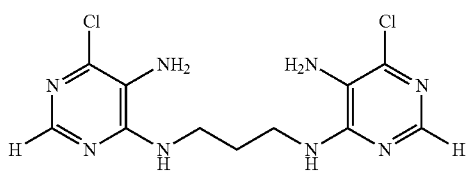 [SMILES: Nc1c(Cl)ncnc1NCCCNc1ncnc(Cl)c1N] | $N^4,N^{4'}$-(propane-1,3-diyl)bis(6-chloropyrimidine-4,5-diamine) |
| 39 | 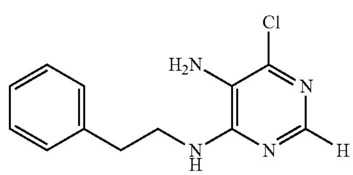 [SMILES: Nc1c(Cl)ncnc1NCCc1ccccc1] | 6-chloro-$N^4$-phenethylpyrimidine-4,5-diamine |
| 40 | 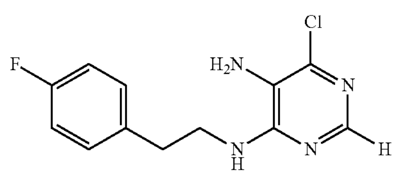 [SMILES: Nc1c(Cl)ncnc1NCCc1ccc(F)cc1] | 6-chloro-$N^4$-(4-fluorophenethyl)pyrimidine-4,5-diamine |
| 41 | 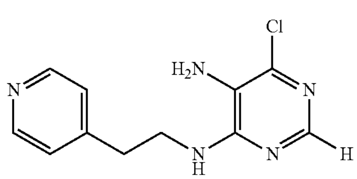 [SMILES: Nc1c(Cl)ncnc1NCCc1ccncc1] | 6-chloro-$N^4$-(2-(pyridin-4-yl)ethyl)pyrimidine-4,5-diamine |
| 42 | 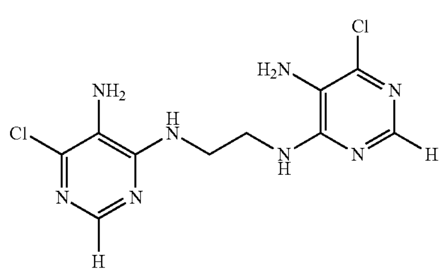 [SMILES: Nc1c(Cl)ncnc1NCCNc1ncnc(Cl)c1N] | $N^4,N^{4'}$-(ethane-1,2-diyl)bis(6-chloropyrimidine-4,5-diamine) |

TABLE 1-continued

| Cpd no | Structure | Chemical name |
|---|---|---|
| 43 | 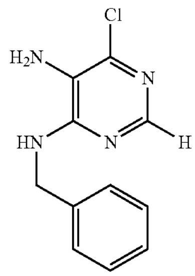 [SMILES: Nc1c(Cl)ncnc1NCc1ccccc1] | $N^4$-benzyl-6-chloropyrimidine-4,5-diamine |
| 44 | 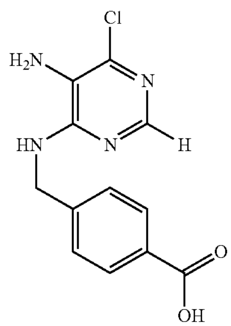 [SMILES: Nc1c(Cl)ncnc1NCc1ccc(C(=O)O)cc1] | 4-(((5-amino-6-chloropyrimidin-4-yl)amino)methyl)benzoic acid |
| 45 | 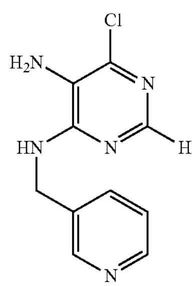 [SMILES: Nc1c(Cl)ncnc1NCc1cccnc1] | 6-chloro-$N^4$-(pyridin-3-ylmethyl)pyrimidine-4,5-diamine |
| 46 | 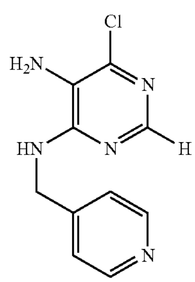 [SMILES: Nc1c(Cl)ncnc1NCc1ccncc1] | 6-chloro-$N^4$-(pyridin-4-ylmethyl)pyrimidine-4,5-diamine |
| 47 | 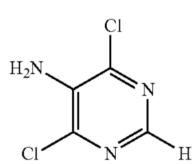 | 4,6-dichloropyrimidin-5-amine |
| 48 | 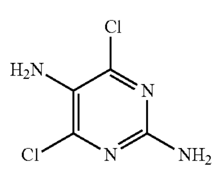 | 4,6-dichloropyrimidine-2,5-diamine |

TABLE 1-continued
| Cpd no | Structure | Chemical name |
| --- | --- | --- |
| 49 | 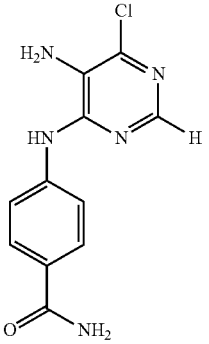 [SMILES: NC(=O)c1ccc(Nc2ncnc(Cl)c2N)cc1] | 4-((5-amino-6-chloropyrimidin-4-yl)amino)benzamide |
| 50 | 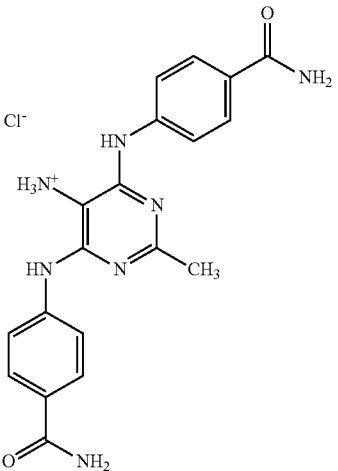 [SMILES: Cc1nc(Nc2ccc(C(N)=O)cc2)c([NH3+])c(Nc2ccc(C(N)=O)cc2)n1 ; [Cl-]] | 4,6-bis((4-carbamoylphenyl)amino)-2-methylpyrimidin-5-aminium chloride |
| 51 | 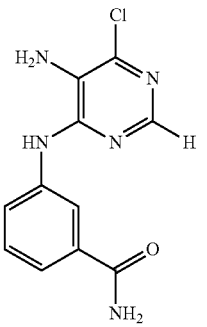 [SMILES: NC(=O)c1cccc(Nc2ncnc(Cl)c2N)c1] | 3-((5-amino-6-chloropyrimidin-4-yl)amino)benzamide |
| 52 | 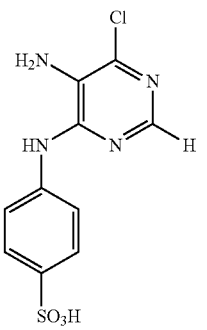 [SMILES: Nc1c(Cl)ncnc1Nc1ccc(S(=O)(=O)O)cc1] | 4-((5-amino-6-chloropyrimidin-4-yl)amino)benzenesulfonic acid |

TABLE 1-continued

| Cpd no | Structure | Chemical name |
|---|---|---|
| 53 | 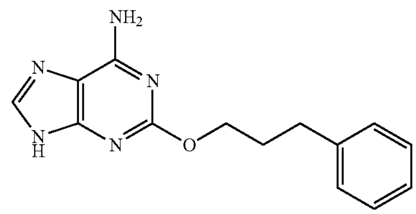 [SMILES: Nc1nc(OCCCc2ccccc2)nc2[nH]cnc12] | 2-(3-phenylpropoxy)-9H-purin-6-amine |
| 54 | 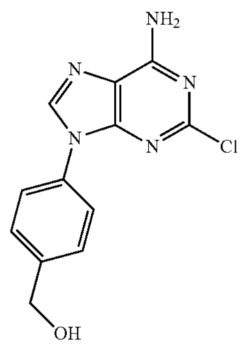 [SMILES: Nc1nc(Cl)nc2c1ncn2-c1ccc(CO)cc1] | (4-(6-amino-2-chloro-9H-purin-9-yl)phenyl)methanol |
| 55 | 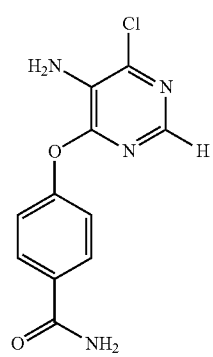 [SMILES: NC(=O)c1ccc(Oc2ncnc(Cl)c2N)cc1] | 4-((5-amino-6-chloropyrimidin-4-yl)oxy)benzamide |
| 56 | 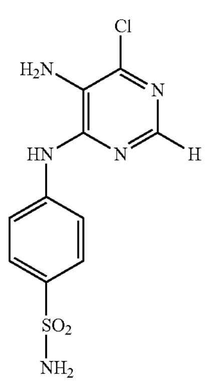 [SMILES: Nc1c(Cl)ncnc1Nc1ccc(S(N)(=O)=O)cc1] | 4-((5-amino-6-chloropyrimidin-4-yl)amino)benzenesulfonamide |

TABLE 1-continued
| Cpd no | Structure | Chemical name |
|---|---|---|
| 57 | 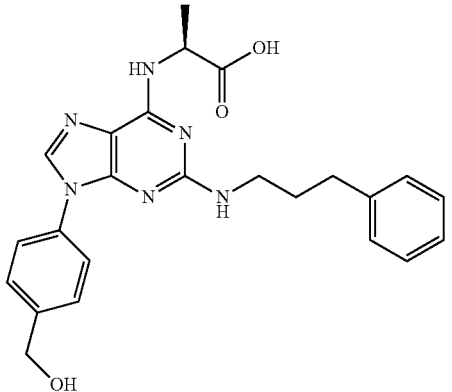 [SMILES: C[C@H](Nc1nc(NCCCc2ccccc2)nc2c1ncn2-c1ccc(CO)cc1)C(=O)O] | (S)-2-((9-(4-(hydroxymethyl)phenyl)-2-((3-phenylpropyl)amino)-9H-purin-6-yl)amino)propanoic acid |
| 58 | 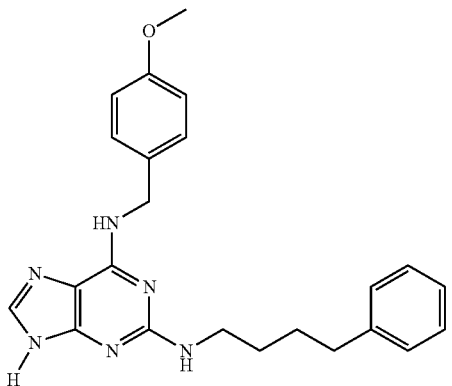 [SMILES: COc1ccc(CNc2nc(NCCCCc3ccccc3)nc3[nH]cnc23)cc1] | N6-(4-methoxybenzyl)-N2-(4-phenylbutyl)-9H-purine-2,6-diamine |
| 59 | 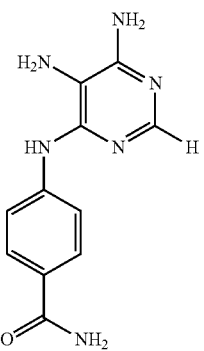 [SMILES: NC(=O)c1ccc(Nc2ncnc(N)c2N)cc1] | 4-((5,6-diaminopyrimidin-4-yl)amino)benzamide |

TABLE 1-continued

| Cpd no | Structure | Chemical name |
|---|---|---|
| 60 | 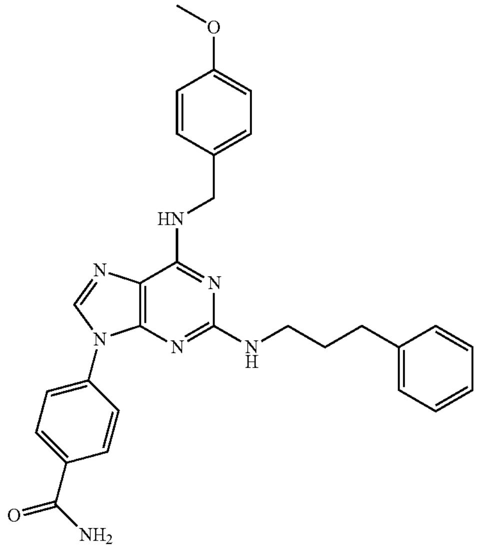 [SMILES: COc1ccc(CNc2nc(NCCCc3ccccc3)nc3c2ncn3-c2ccc(C(N)=O)cc2)cc1] | 4-(6-((4-methoxybenzyl)amino)-2-((3-phenylpropyl)amino)-9H-purin-9-yl)benzamide |
| 61 | 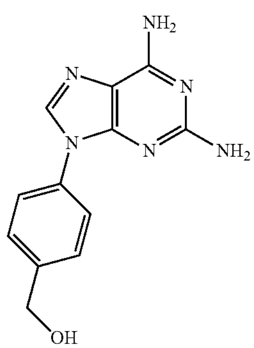 [SMILES: Nc1nc(N)c2ncn(-c3ccc(CO)cc3)c2n1] | (4-(2,6-diamino-9H-purin-9-yl)phenyl)methanol |
| 62 | 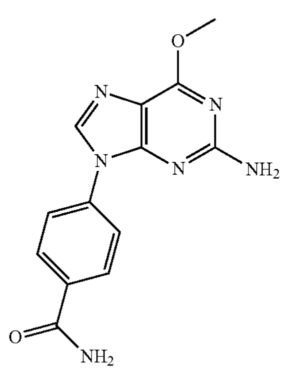 [SMILES: COc1nc(N)nc2c1ncn2-c1ccc(C(N)=O)cc1] | 4-(2-amino-6-methoxy-9H-purin-9-yl)benzamide |
| 63 | 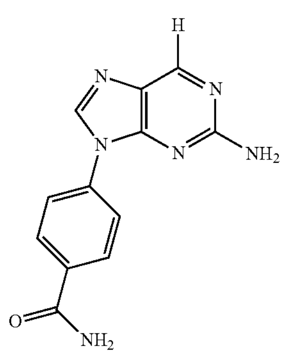 [SMILES: NC(=O)c1ccc(-n2cnc3cnc(N)nc32)cc1] | 4-(2-amino-9H-purin-9-yl)benzamide |

TABLE 1-continued

| Cpd no | Structure | Chemical name |
|---|---|---|
| 64 | 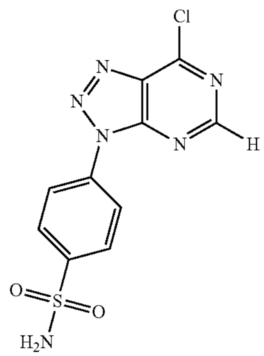 [SMILES: NS(=O)(=O)c1ccc(-n2nnc3c(Cl)ncnc32)cc1] | 4-(7-chloro-3H-[1,2,3]triazolo[4,5-d]pyrimidin-3-yl)benzenesulfonamide |
| 65 | 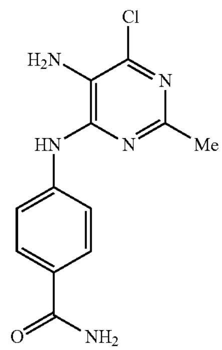 [SMILES: Cc1nc(Cl)c(N)c(Nc2ccc(C(N)=O)cc2)n1] | 4-((5-amino-6-chloro-2-methylpyrimidin-4-yl)amino)benzamide |
| 66 | 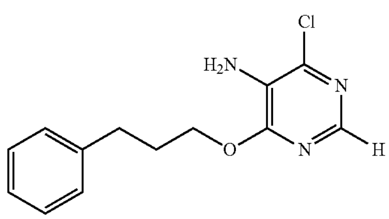 [SMILES: Nc1c(Cl)ncnc1OCCCc1ccccc1] | 4-chloro-6-(3-phenylpropoxy)pyrimidin-5-amine |
| 67 | 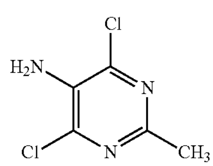 | 4,6-dichloro-2-methylpyrimidin-5-amine |
| 68 | 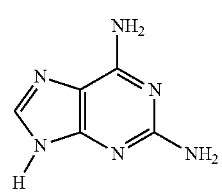 [SMILES: Nc1nc(N)c2nc[nH]c2n1] | 9H-purine-2,6-diamine |
| 69 | 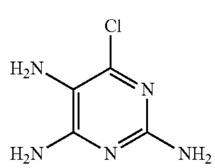 | 6-chloropyrimidine-2,4,5-triamine |

TABLE 1-continued

| Cpd no | Structure | Chemical name |
|---|---|---|
| 70 | 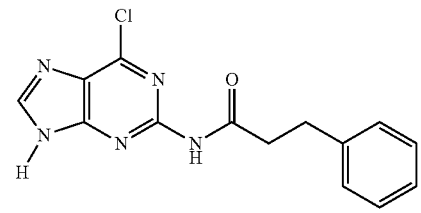 [SMILES: O=C(CCc1ccccc1)Nc1nc(Cl)c2nc[nH]c2n1] | N-(6-chloro-9H-purin-2-yl)-3-phenylpropanamide |
| 71 | 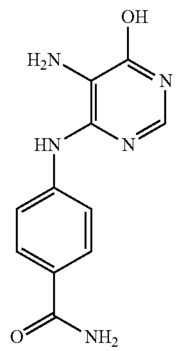 [SMILES: NC(=O)c1ccc(Nc2ncnc(O)c2N)cc1] | 4-((5-amino-6-hydroxypyrimidin-4-yl)amino)benzamide |
| 72 | 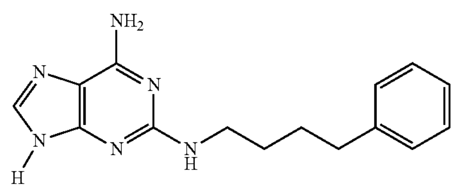 [SMILES: Nc1nc(NCCCCc2ccccc2)nc2[nH]cnc12] | N2-(4-phenylbutyl)-9H-purine-2,6-diamine |
| 74 | 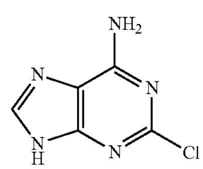 [SMILES: Nc1nc(Cl)nc2[nH]cnc12] | 2-chloro-9H-purin-6-amine |
| 75 | 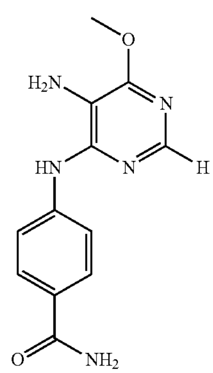 | 4-((5-amino-6-methoxypyrimidin-4-yl)amino)benzamide |

TABLE 1-continued
| Cpd no | Structure | Chemical name |
|---|---|---|
| 76 | 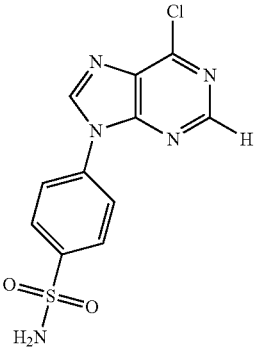 [SMILES: NS(=O)(=O)c1ccc(-n2cnc3c(Cl)ncnc32)cc1] | 4-(6-chloro-9H-purin-9-yl)benzenesulfonamide |
| 77 | 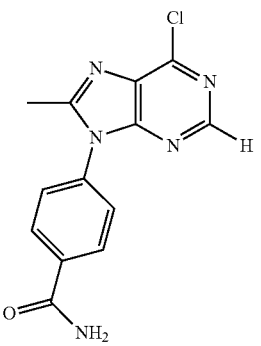 [SMILES: Cc1nc2c(Cl)ncnc2n1-c1ccc(C(N)=O)cc1] | 4-(6-chloro-8-methyl-9H-purin-9-yl)benzamide |
| 78 | 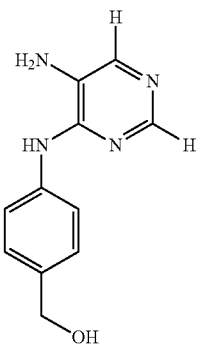 [SMILES: Nc1cncnc1Nc1ccc(CO)cc1] | (4-((5-aminopyrimidin-4-yl)amino)phenyl)methanol |
| 79 | 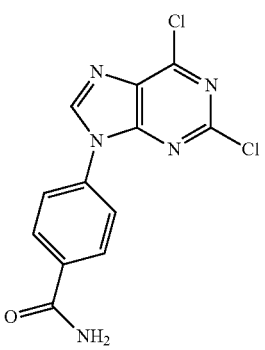 [SMILES: NC(=O)c1ccc(-n2cnc3c(Cl)nc(Cl)nc32)cc1] | 4-(2,6-dichloro-9H-purin-9-yl)benzamide |

TABLE 1-continued

| Cpd no | Structure | Chemical name |
|---|---|---|
| 80 | 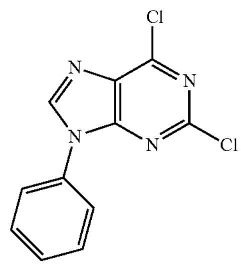 [SMILES: Clc1nc(Cl)c2ncn(-c3ccccc3)c2n1] | 2,6-dichloro-9-phenyl-9H-purine |
| 81 | 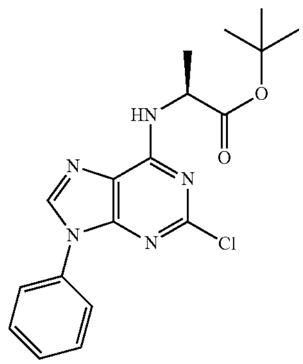 [SMILES: C[C@H](Nc1nc(Cl)nc2c1ncn2-c1ccccc1)C(=O)OC(C)(C)C] | (S)-tert-butyl 2-((2-chloro-9-phenyl-9H-purin-6-yl)amino)propanoate |
| 82 | 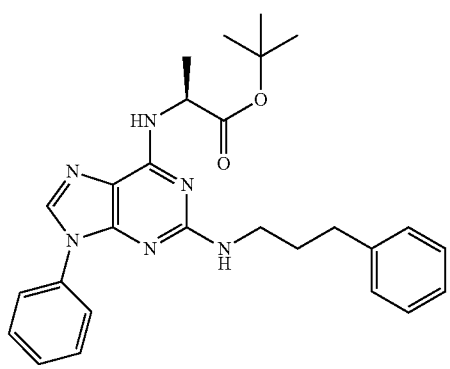 [SMILES: C[C@H](Nc1nc(NCCCc2ccccc2)nc2c1ncn2-c1ccccc1)C(=O)OC(C)(C)C] | (S)-tert-butyl 2-((9-phenyl-2-((3-phenylpropyl)amino)-9H-purin-6-yl)amino)propanoate |
| 83 | 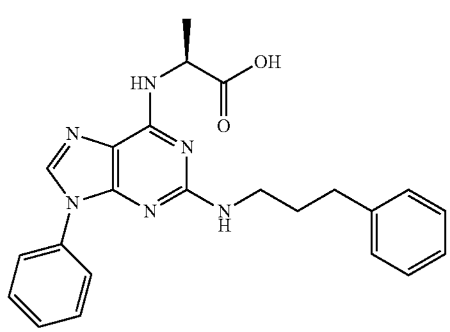 [SMILES: C[C@H](Nc1nc(NCCCc2ccccc2)nc2c1ncn2-c1ccccc1)C(=O)O] | (S)-2-((9-phenyl-2-((3-phenylpropyl)amino)-9H-purin-6-yl)amino)propanoic acid |

TABLE 1-continued
| Cpd no | Structure | Chemical name |
|---|---|---|
| 85 | 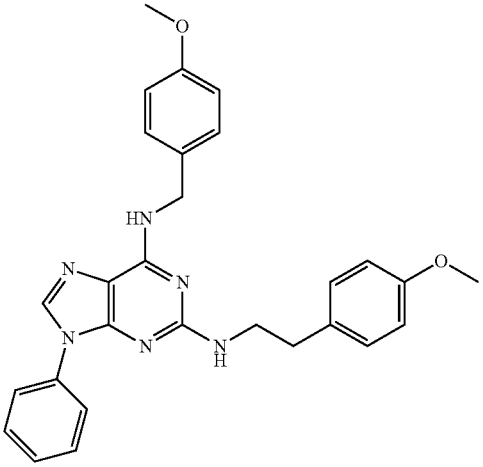 [SMILES: COc1ccc(CCNc2nc(NCc3ccc(OC)cc3)c3ncn(-c4ccccc4)c3n2)cc1] | N6-(4-methoxybenzyl)-N2-(4-methoxyphenethyl)-9-phenyl-9H-purine-2,6-diamine |
| 86 | 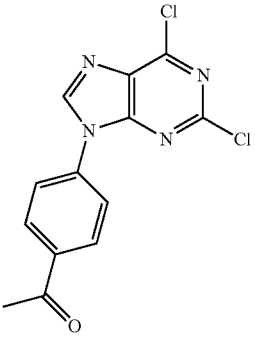 [SMILES: CC(=O)c1ccc(-n2cnc3c(Cl)nc(Cl)nc32)cc1] | 1-(4-(2,6-dichloro-9H-purin-9-yl)phenyl)ethanone |
| 88 | 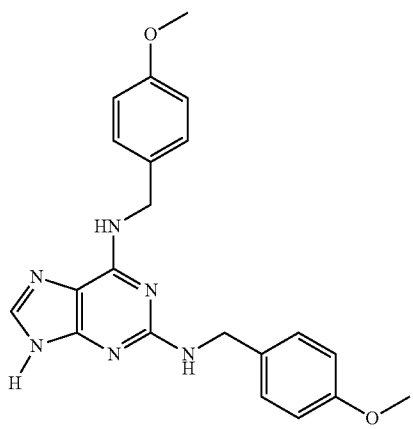 [SMILES: COc1ccc(CNc2nc(NCc3ccc(OC)cc3)c3nc[nH]c3n2)cc1] | N2,N6-bis(4-methoxybenzyl)-9H-purine-2,6-diamine |

TABLE 1-continued
| Cpd no | Structure | Chemical name |
|---|---|---|
| 89 | 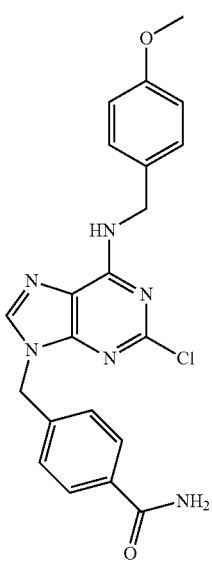 [SMILES: COc1ccc(CNc2nc(Cl)nc3c2ncn3Cc2ccc(C(N)=O)cc2)cc1] | 4-((2-chloro-6-((4-methoxybenzyl)amino)-9H-purin-9-yl)methyl)benzamide |
| 90 | 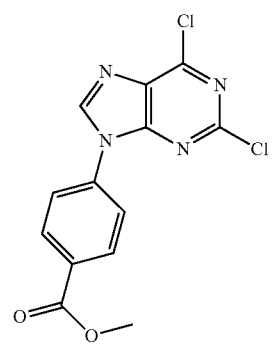 [SMILES: COC(=O)c1ccc(-n2cnc3c(Cl)nc(Cl)nc32)cc1] | methyl 4-(2,6-dichloro-9H-purin-9-yl)benzoate |
| 91 | 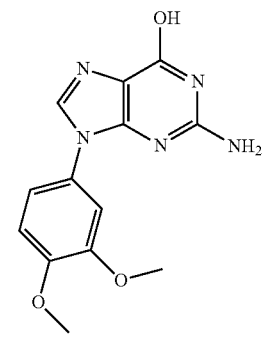 [SMILES: COc1ccc(-n2cnc3c(O)nc(N)nc32)cc1OC] | 2-amino-9-(3,4-dimethoxyphenyl)-9H-purin-6-ol |
| 92 | 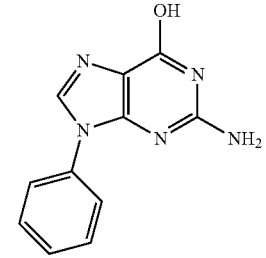 [SMILES: Nc1nc(O)c2ncn(-c3ccccc3)c2n1] | 2-amino-9-phenyl-9H-purin-6-ol |

TABLE 1-continued

| Cpd no | Structure | Chemical name |
|---|---|---|
| 93 | 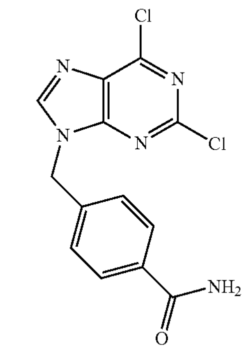 [SMILES: NC(=O)c1ccc(Cn2cnc3c(Cl)nc(Cl)nc32)cc1] | 4-((2,6-dichloro-9H-purin-9-yl)methyl)benzamide |
| 94 | 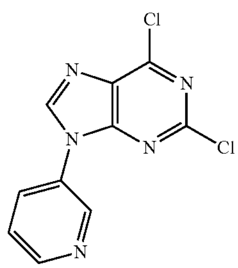 [SMILES: Clc1nc(Cl)c2ncn(-c3cccnc3)c2n1] | 2,6-dichloro-9-(pyridin-3-yl)-9H-purine |
| 95 | 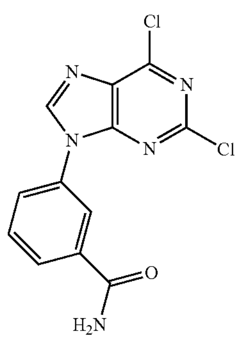 [SMILES: NC(=O)c1cccc(-n2cnc3c(Cl)nc(Cl)nc32)c1] | 3-(2,6-dichloro-9H-purin-9-yl)benzamide |
| 96 | 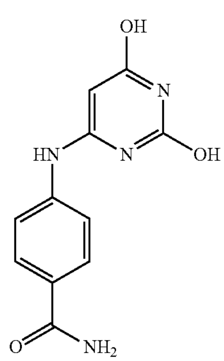 [SMILES: NC(=O)c1ccc(Nc2cc(O)nc(O)n2)cc1] | 4-((2,6-dihydroxypyrimidin-4-yl)amino)benzamide |

TABLE 1-continued
| Cpd no | Structure | Chemical name |
|---|---|---|
| 97 | 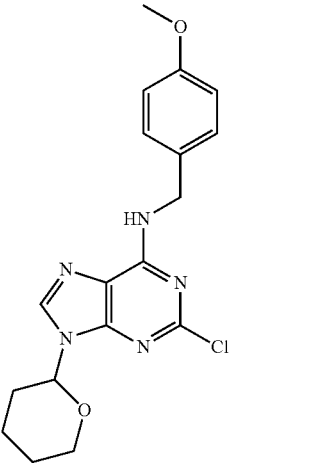 [SMILES: COc1ccc(CNc2nc(Cl)nc3c2ncn3C2CCCCO2)cc1] | 2-chloro-N-(4-methoxybenzyl)-9-(tetrahydro-2H-pyran-2-yl)-9H-purin-6-amine |
| 98 | 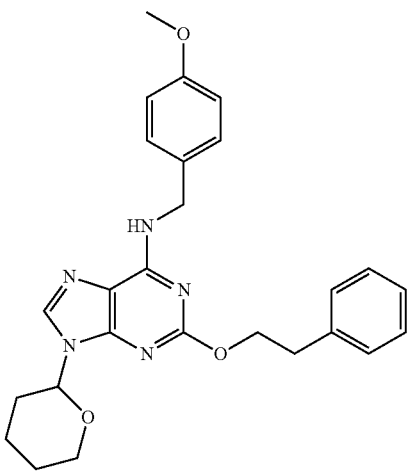 [SMILES: COc1ccc(CNc2nc(OCCc3ccccc3)nc3c2ncn3C2CCCCO2)cc1] | N-(4-methoxybenzyl)-2-phenethoxy-9-(tetrahydro-2H-pyran-2-yl)-9H-purin-6-amine |
| 99 | 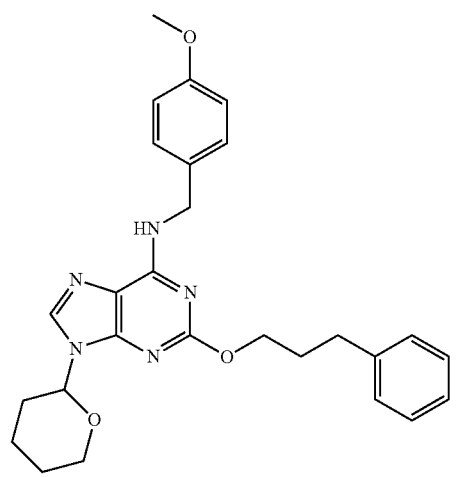 [SMILES: COc1ccc(CNc2nc(OCCCc3ccccc3)nc3c2ncn3C2CCCCO2)cc1] | N-(4-methoxybenzyl)-2-(3-phenylpropoxy)-9-(tetrahydro-2H-pyran-2-yl)-9H-purin-6-amine |

TABLE 1-continued
| Cpd no | Structure | Chemical name |
|---|---|---|
| 100 | 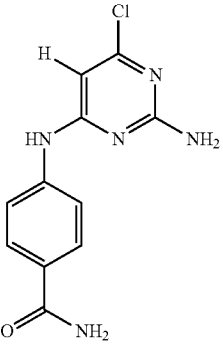 [SMILES: NC(=O)c1ccc(Nc2cc(Cl)nc(N)n2)cc1] | 4-((2-amino-6-chloropyrimidin-4-yl)amino)benzamide |
| 101 | 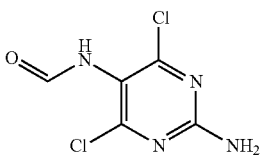 [SMILES: Nc1nc(Cl)c(NC=O)c(Cl)n1] | N-(2-amino-4,6-dichloropyrimidin-5-yl)formamide |
| 102 | 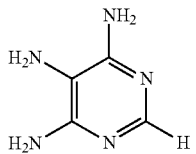 | pyrimidine-4,5,6-triamine |
| 103 | 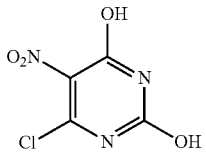 [SMILES: O=[N+]([O-])c1c(O)nc(O)nc1Cl] | 6-chloro-5-nitropyrimidine-2,4-diol |
| 104 | 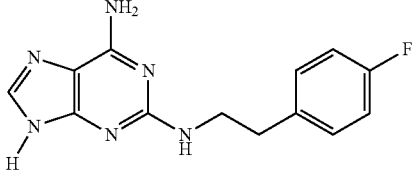 [SMILES: Nc1nc(NCCc2ccc(F)cc2)nc2[nH]cnc12] | N2-(4-fluorophenethyl)-9H-purine-2,6-diamine |
| 105 | 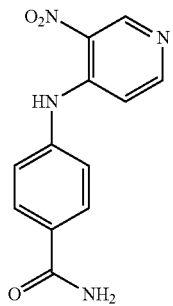 | 4-((3-nitropyridin-4-yl)amino)benzamide |

TABLE 1-continued
| Cpd no | Structure | Chemical name |
|---|---|---|
| 106 | 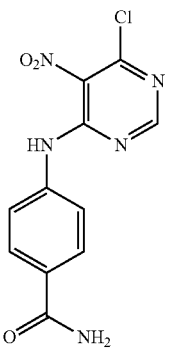 | 4-((6-chloro-5-nitropyrimidin-4-yl)amino)benzamide |
| 107 | 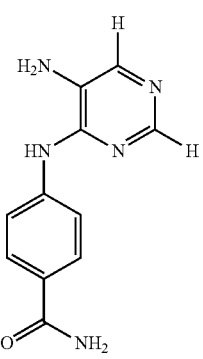 | 4-((5-aminopyrimidin-4-yl)amino)benzamide |
| 108 | 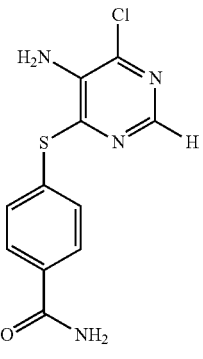 [SMILES: NC(=O)c1ccc(Sc2ncnc(Cl)c2N)cc1] | 4-((5-amino-6-chloropyrimidin-4-yl)thio)benzamide |
| 109 | 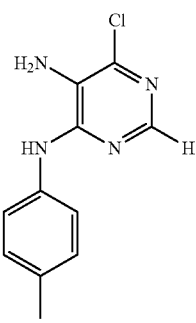 [SMILES: Cc1ccc(Nc2ncnc(Cl)c2N)cc1] | 6-chloro-N4-(p-tolyl)pyrimidine-4,5-diamine |

TABLE 1-continued

| Cpd no | Structure | Chemical name |
| --- | --- | --- |
| 110 | 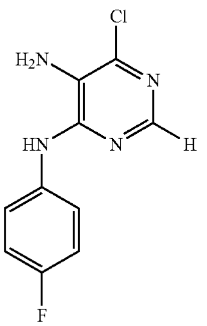 [SMILES: Nc1c(Cl)ncnc1Nc1ccc(F)cc1] | 6-chloro-N4-(4-fluorophenyl)pyrimidine-4,5-diamine |
| 111 | 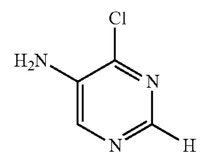 | 4-chloropyrimidin-5-amine |
| 112 | 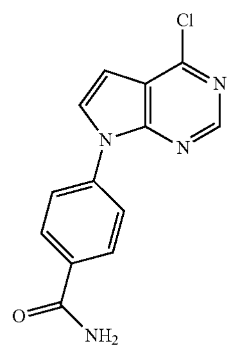 [SMILES: NC(=O)c1ccc(-n2ccc3c(Cl)ncnc32)cc1] | 4-(4-chloro-7H-pyrrolo[2,3-d]pyrimidin-7-yl)benzamide |
| 113 | 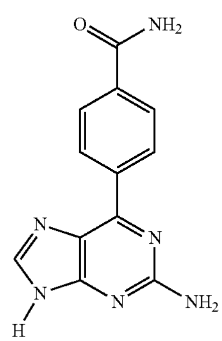 [SMILES: NC(=O)c1ccc(-c2nc(N)nc3[nH]cnc23)cc1] | 4-(2-amino-9H-purin-6-yl)benzamide |
| 114 | 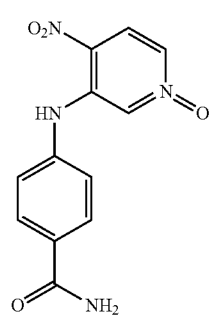 [SMILES: NC(=O)c1ccc(Nc2c[n+]([O-])ccc2[N+](=O)[O-])cc1] | 3-((4-carbamoylphenyl)amino)-4-nitropyridine 1-oxide |

TABLE 1-continued
| Cpd no | Structure | Chemical name |
|---|---|---|
| 115 | 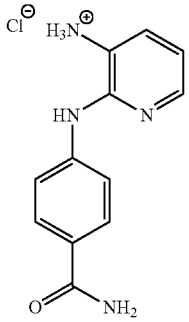 [SMILES: [Cl-] ; NC(=O)c1ccc(Nc2ncccc2[NH3+])cc1] | 2-((4-carbamoylphenyl)amino)-pyridin-3-aminium chloride |
| 116 | 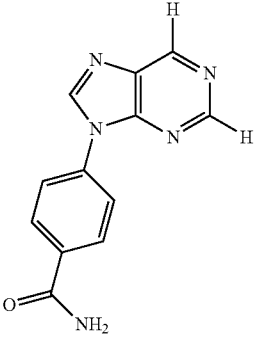 [SMILES: NC(=O)c1ccc(-n2cnc3cncnc32)cc1] | 4-(9H-purin-9-yl)benzamide |
| 117 | 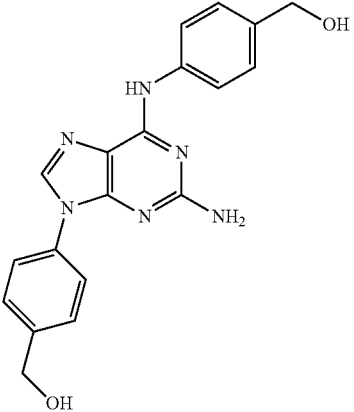 [SMILES: Nc1nc(Nc2ccc(CO)cc2)c2ncn(-c3ccc(CO)cc3)c2n1] | (4-(2-amino-6-((4-(hydroxymethyl)phenyl)-amino)-9H-purin-9-yl)phenyl)methanol |
| 118 | 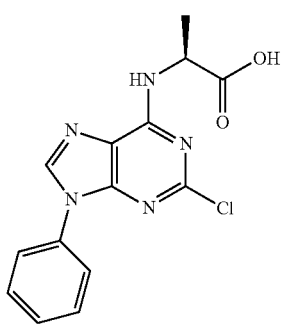 [SMILES: C[C@H](Nc1nc(Cl)nc2c1ncn2-c1ccccc1)C(=O)O] | (S)-2-((2-chloro-9-phenyl-9H-purin-6-yl)amino)propanoic acid |

TABLE 1-continued
| Cpd no | Structure | Chemical name |
|---|---|---|
| 119 | 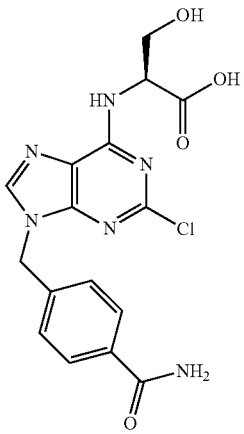 [SMILES: NC(=O)c1ccc(Cn2cnc3c(N[C@@H](CO)C(=O)O)nc(Cl)nc32)cc1] | (S)-2-((9-(4-carbamoylbenzyl)-2-chloro-9H-purin-6-yl)amino)-3-hydroxypropanoic acid |
| 120 | 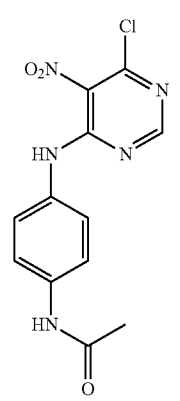 [SMILES: CC(=O)Nc1ccc(Nc2ncnc(Cl)c2[N+](=O)[O-])cc1] | N-(4-((6-chloro-5-nitropyrimidin-4-yl)amino)phenyl)acetamide |
| 121 | 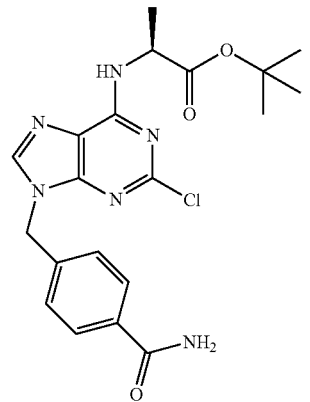 [SMILES: C[C@H](Nc1nc(Cl)nc2c1ncn2Cc1ccc(C(N)=O)cc1)C(=O)OC(C)(C)C] | (S)-tert-butyl 2-((9-(4-carbamoylbenzyl)-2-chloro-9H-purin-6-yl)amino)propanoate |
| 122 | 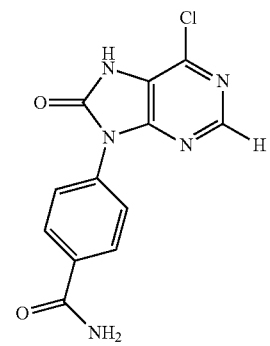 [SMILES: NC(=O)c1ccc(-n2c(=O)[nH]c3c(Cl)ncnc32)cc1] | 4-(6-chloro-8-oxo-7H-purin-9(8H)-yl)benzamide |

TABLE 1-continued

| Cpd no | Structure | Chemical name |
|---|---|---|
| 123 | 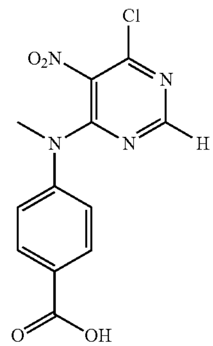 [SMILES: CN(c1ccc(C(=O)O)cc1)c1ncnc(Cl)c1[N+](=O)[O-]] | 4-((6-chloro-5-nitropyrimidin-4-yl)(methyl)amino)benzoic acid |
| 124 | 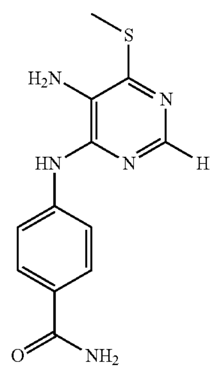 [SMILES: CSc1ncnc(Nc2ccc(C(N)=O)cc2)c1N] | 4-((5-amino-6-(methylthio)pyrimidin-4-yl)amino)benzamide |
| 125 | 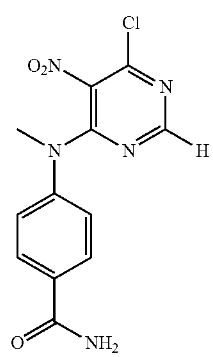 [SMILES: CN(c1ccc(C(N)=O)cc1)c1ncnc(Cl)c1[N+](=O)[O-]] | 4-((6-chloro-5-nitropyrimidin-4-yl)(methyl)amino)benzamide |
| 126 | 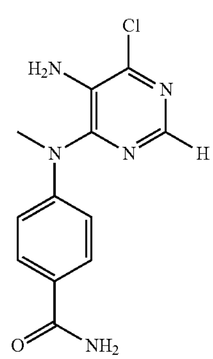 | 4-((5-amino-6-chloropyrimidin-4-yl)(methyl)amino)benzamide |

TABLE 1-continued
| Cpd no | Structure | Chemical name |
|---|---|---|
| 127 | 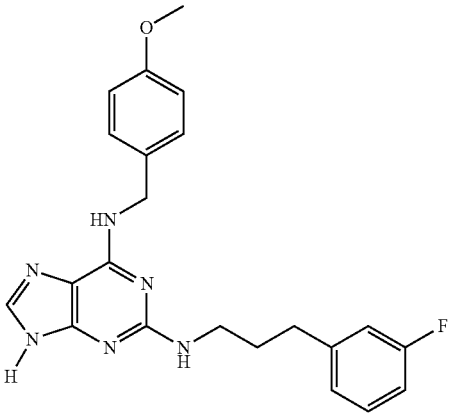 [SMILES: COc1ccc(CNc2nc(NCCCc3cccc(F)c3)nc3[nH]cnc23)cc1] | N2-(3-(3-fluorophenyl)propyl)-N6-(4-methoxybenzyl)-9H-purine-2,6-diamine |
| 128 | 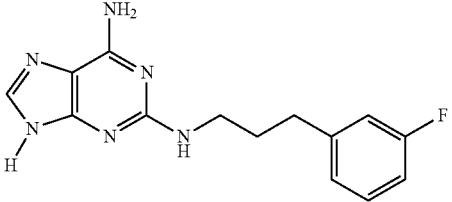 [SMILES: Nc1nc(NCCCc2cccc(F)c2)nc2[nH]cnc12] | N2-(3-(3-fluorophenyl)propyl)-9H-purine-2,6-diamine |
| 129 | 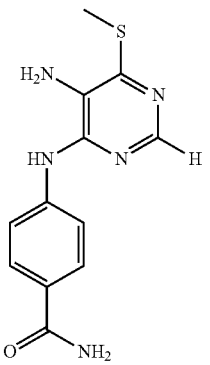 [SMILES: CSc1ncnc(Nc2ccc(C(N)=O)cc2)c1N] | 4-((5-amino-6-(methylthio)pyrimidin-4-yl)amino)benzamide |
| 130 | 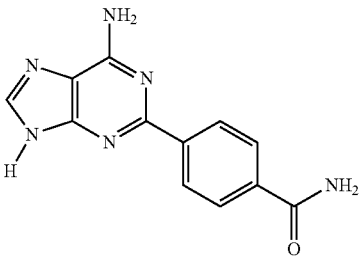 [SMILES: NC(=O)c1ccc(-c2nc(N)c3nc[nH]c3n2)cc1] | 4-(6-amino-9H-purin-2-yl)benzamide |

TABLE 1-continued

| Cpd no | Structure | Chemical name |
| --- | --- | --- |
| 131 | 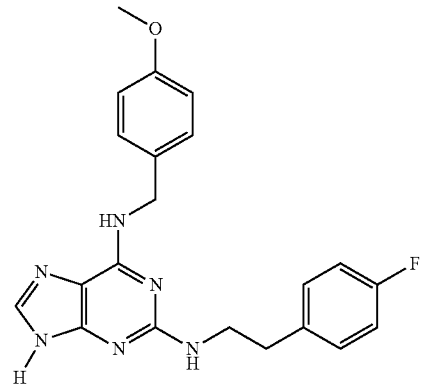 [SMILES: COc1ccc(CNc2nc(NCCc3ccc(F)cc3)nc3[nH]cnc23)cc1] | N2-(4-fluorophenethyl)-N6-(4-methoxybenzyl)-9H-purine-2,6-diamine |
| 132 | 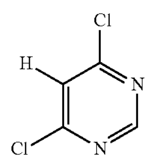 | 4,6-dichloropyrimidine |
| 133 | 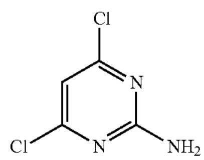 | 4,6-dichloropyrimidin-2-amine |
| 134 | 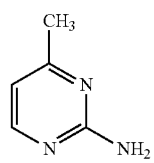 | 4-methylpyrimidin-2-amine |
| 135 | 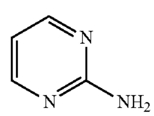 | pyrimidin-2-amine |
| 136 | 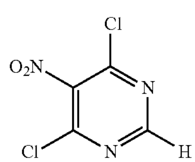 [SMILES: O=[N+]([O-])c1c(Cl)ncnc1Cl] | 4,6-dichloro-5-nitropyrimidine |
| 137 | 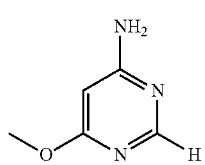 | 6-methoxypyrimidin-4-amine |
| 138 | 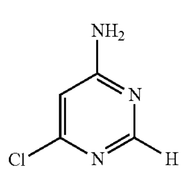 | 6-chloropyrimidin-4-amine |

TABLE 1-continued

| Cpd no | Structure | Chemical name |
| --- | --- | --- |
| 139 | 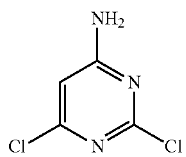 | 2,6-dichloropyrimidin-4-amine |
| 140 | 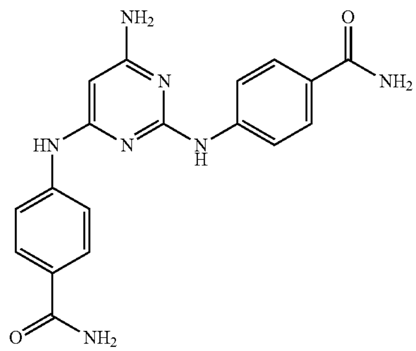 [SMILES: NC(=O)c1ccc(Nc2cc(N)nc(Nc3ccc(C(N)=O)cc3)n2)cc1] | 4,4'-((6-aminopyrimidine-2,4-diyl)bis(azanediyl))dibenzamide |
| 141 | 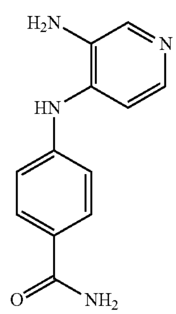 [SMILES: NC(=O)c1ccc(Nc2ccncc2N)cc1] | 4-((3-aminopyridin-4-yl)amino)benzamide |
| 142 | 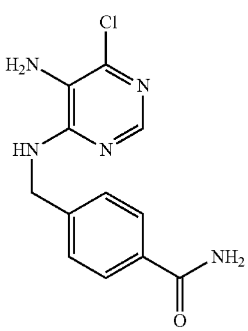 [SMILES: NC(=O)c1ccc(CNc2ncnc(Cl)c2N)cc1] | 4-(((5-amino-6-chloropyrimidin-4-yl)amino)methyl)benzamide |
| 143 | 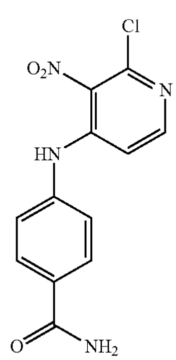 [SMILES: NC(=O)c1ccc(Nc2ccnc(Cl)c2[N+](=O)[O-])cc1] | 4-((2-chloro-3-nitropyridin-4-yl)amino)benzamide |

TABLE 1-continued

| Cpd no | Structure | Chemical name |
| --- | --- | --- |
| 144 | 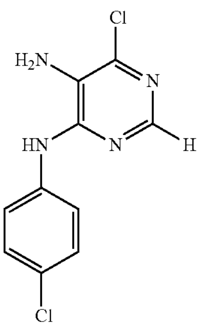 [SMILES: Nc1c(Cl)ncnc1Nc1ccc(Cl)cc1] | 6-chloro-N4-(4-chlorophenyl)pyrimidine-4,5-diamine |
| 145 | 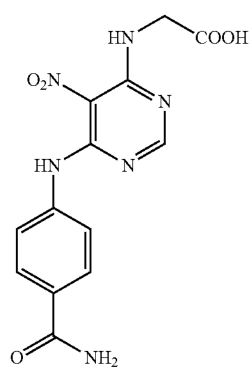 [SMILES: NC(=O)c1ccc(Nc2ncnc(NCC(=O)O)c2[N+](=O)[O-])cc1] | 2-((6-((4-carbamoylphenyl)amino)-5-nitropyrimidin-4-yl)amino)acetic acid |
| 146 | 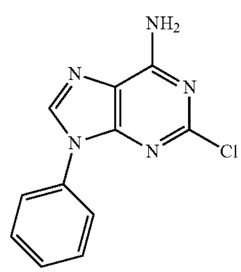 [SMILES: Nc1nc(Cl)nc2c1ncn2-c1ccccc1] | 2-chloro-9-phenyl-9H-purin-6-amine |
| 147 | 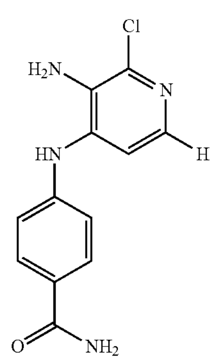 [SMILES: NC(=O)c1ccc(Nc2ccnc(Cl)c2N)cc1] | 4-((3-amino-2-chloropyridin-4-yl)amino)benzamide |

TABLE 1-continued
| Cpd no | Structure | Chemical name |
|---|---|---|
| 148 | 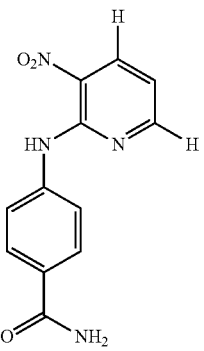 [SMILES: NC(=O)c1ccc(Nc2ncccc2[N+](=O)[O-])cc1] | 4-((3-nitropyridin-2-yl)amino)benzamide |
| 149 | 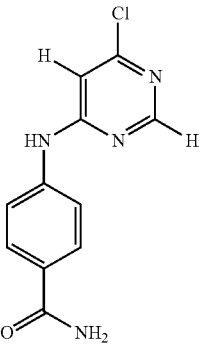 [SMILES: NC(=O)c1ccc(Nc2cc(Cl)ncn2)cc1] | 4-((6-chloropyrimidin-4-yl)amino)benzamide |
| 150 | 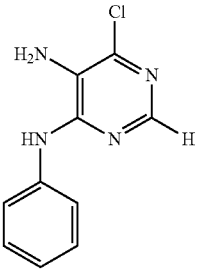 [SMILES: Nc1c(Cl)ncnc1Nc1ccccc1] | 6-chloro-N4-phenylpyrimidine-4,5-diamine |
| 151 | 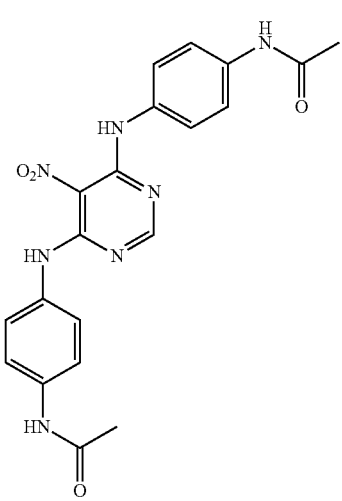 [SMILES: CC(=O)Nc1ccc(Nc2ncnc(Nc3ccc(NC(C)=O)cc3)c2[N+](=O)[O-])cc1] | N,N'-(((5-nitropyrimidine-4,6-diyl)bis(azanediyl))bis(4,1-phenylene))diacetamide |

TABLE 1-continued
| Cpd no | Structure | Chemical name |
|---|---|---|
| 152 | 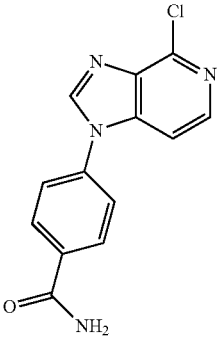 | 4-(4-chloro-1H-imidazo[4,5-c]pyridin-1-yl)benzamide |
| 153 | 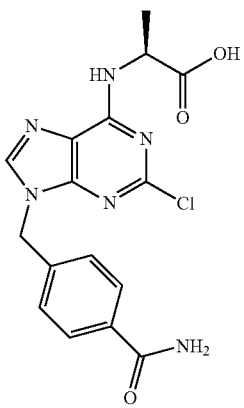 [SMILES: C[C@H](Nc1nc(Cl)nc2c1ncn2Cc1ccc(C(N)=O)cc1)C(=O)O] | (S)-2-((9-(4-carbamoylbenzyl)-2-chloro-9H-purin-6-yl)amino)propanoic acid |
| 154 | 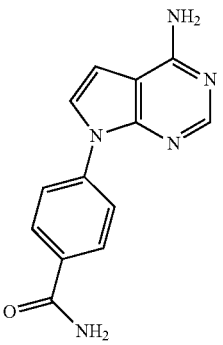 | 4-(4-amino-7H-pyrrolo[2,3-d]pyrimidin-7-yl)benzamide |
| 155 | 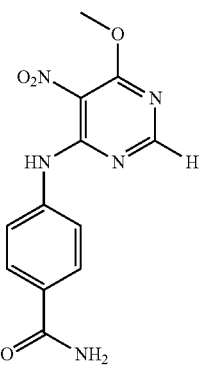 [SMILES: COc1ncnc(Nc2ccc(C(N)=O)cc2)c1[N+](=O)[O-]] | 4-((6-methoxy-5-nitropyrimidin-4-yl)amino)benzamide |

TABLE 1-continued

| Cpd no | Structure | Chemical name |
| --- | --- | --- |
| 156 | 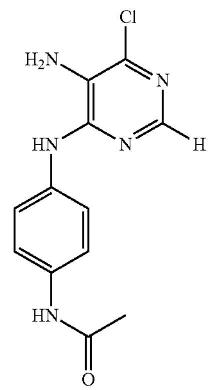 [SMILES: CC(=O)Nc1ccc(Nc2ncnc(Cl)c2N)cc1] | N-(4-((5-amino-6-chloropyrimidin-4-yl)amino)phenyl)acetamide |
| 157 | 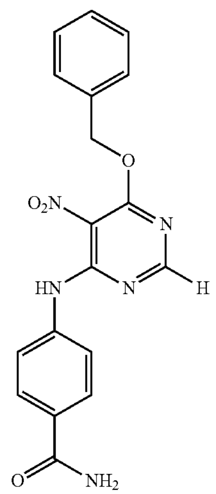 [SMILES: NC(=O)c1ccc(Nc2ncnc(OCc3ccccc3)c2[N+](=O)[O-])cc1] | 4-((6-(benzyloxy)-5-nitropyrimidin-4-yl)amino)benzamide |
| 158 | | N4-(4-((benzyloxy)methyl)phenyl)-6-chloropyrimidine-4,5-diamine | or pharmaceutically acceptable enantiomers, salts, solvates and prodrugs thereof.

In Table 1, the term "Cpd" means compound. The compounds of Table 1 were named using ChemBioDraw® Ultra version 12.0 (PerkinElmer).

The present invention also relates to compounds of general Formula II

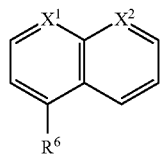

(II)

and pharmaceutically acceptable enantiomers, salts, solvates and prodrugs thereof, wherein $X^1$ and $X^2$ represent respectively CH and N or N and CH;

$R^6$ represents H, arylalkyl wherein the aryl group is optionally substituted by one or more group selected from halo and carboxyl; heteroarylalkyl; heteroarylaminoalkyl wherein the heteroaryl group is optionally substituted by one or more group selected from halo and $NH_2$; aminoalkyl; aryl substituted by one or more group selected from alkyloxy, hydroxymethyl, $CONH_2$, COOH, COOalkyl $SO_3H$, $SO_2NH_2$; preferably $R^6$ represents H, phenylalkyl wherein the phenyl group is optionally substituted by one or more group selected from fluoro and carboxyl and wherein the alkyl is preferably selected from methyl, ethyl, n-propyl, n-butyl; heteroarylalkyl wherein the heteroaryl is preferably pyridine and wherein the alkyl group is preferably selected from methyl and ethyl; heteroarylaminoalkyl wherein the heteroaryl group is optionally substituted by one or more group selected from Cl and $NH_2$ and wherein the heteroaryl is preferably pyrimidine and wherein the alkyl group is preferably selected from ethyl and n-propyl; amino-n-propyl; phenyl substituted in para or meta, preferably in para, by one or more group selected from hydroxymethyl, $CONH_2$, COOH, COOMe and $SO_3H$; more preferably $R^6$ represents phenyl substituted in para by hydroxymethyl or $CONH_2$.

Particularly preferred compounds of Formula II of the invention are those listed in Table 2 hereafter.

TABLE 2

| Cpd no | Structure | Chemical name |
|---|---|---|
| II-1 | 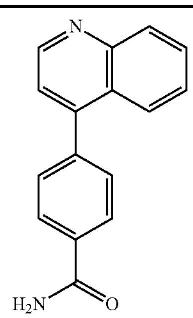 | 4-(quinolin-4-yl)benzamide |
| II-2 | | 4-(quinolin-5-yl)benzamide | or pharmaceutically acceptable enantiomers, salts, solvates and prodrugs thereof.

In Table 2, the term "Cpd" means compound. The compounds of Table 2 were named using ChemBioDraw® Ultra version 12.0 (PerkinElmer).

The compounds of the invention may contain one or more asymmetric center and may thus exist as different stereoisomeric forms. Accordingly, the present invention includes all possible stereoisomers and includes not only racemic compounds but the individual enantiomers and their non-racemic mixtures as well. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be performed by any suitable method known in the art.

The compounds of the invention may be in the form of pharmaceutically acceptable salts. Pharmaceutically acceptable salts of the compounds of the invention include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen, phosphate/dihydrogen, phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate.

When the compounds of the invention contain an acidic group as well as a basic group the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule.

Pharmaceutically acceptable salts of compounds of the invention may be prepared by one or more of these methods:
(i) by reacting the compound of the invention with the desired acid;
(ii) by reacting the compound of the invention with the desired base;
(iii) by removing an acid- or base-labile protecting group from a suitable precursor of the compound of the invention or by ring-opening a suitable cyclic precursor, for example, a lactone or lactam, using the desired acid; or
(iv) by converting one salt of the compound of the invention to another by reaction with an appropriate acid or by means of a suitable ion exchange column.

All these reactions are typically carried out in solution. The salt, may precipitate from solution and be collected by filtration or may be recovered by evaporation of the solvent. The degree of ionization in the salt may vary from completely ionized to almost non-ionized.

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide.

These salts may be prepared by standard procedures, e.g. by reacting a free acid with a suitable organic or inorganic base. Where a basic group is present, such as amino, an acidic salt, i.e. hydrochloride, hydrobromide, acetate, palmoate, and the like, can be used as the dosage form.

In addition, although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of the invention.

Also, in the case of an alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

All references to compounds of the invention include references to enantiomers, salts, solvates, polymorphs, multi-component complexes and liquid crystals thereof.

The compounds of the invention include compounds of the invention as hereinbefore defined, including all polymorphs and crystal habits thereof, prodrugs and isomers thereof (including optical, geometric and tautomeric isomers) and isotopically-labeled compounds of the invention.

The invention also generally covers all pharmaceutically acceptable predrugs and prodrugs of the compounds of the invention.

Process for Manufacturing

The compounds of Formula I and Formula II can be prepared by different ways with reactions known to a person skilled in the art.

The invention further relates to a process for manufacturing of compounds of Formula Ib-2a,

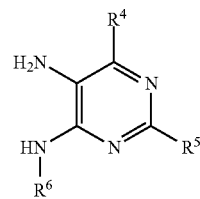

(Ib-2a)

and pharmaceutically acceptable enantiomers, salts, solvates and prodrugs thereof, wherein $R^4$, $R^5$ and $R^6$ are as defined above;

comprising coupling compound of Formula (i)

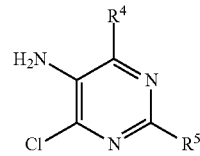

(i)

wherein $R^4$ and $R^5$ are as defined above
with amine of Formula (ii)

wherein $R^6$ is as defined above;
to afford compound of Formula Ib-2a.

According to a preferred embodiment, the coupling of the process for manufacturing compounds of Formula Ib-2a is performed in presence of a base, preferably $Na_2CO_3$. Preferably, the coupling is performed in a solvent selected from water, dioxane, or a mixture thereof, preferably a mixture of water and dioxane. Preferably, the coupling is performed at solvent reflux.

The invention further relates to a process for manufacturing of compounds of Formula II,

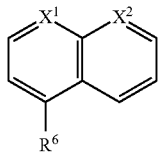

(II)

and pharmaceutically acceptable enantiomers, salts, solvates and prodrugs thereof, wherein $X^1$, $X^2$ and $R^6$ are as defined above;

comprising performing a Suzuki coupling between compound of Formula (i)

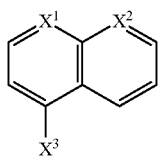

(i)

wherein $X^1$ and $X^2$ are as defined above; and $X^3$ represents an halogen, preferably Cl;

and boronic acid of Formula (ii)

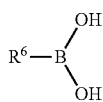

(ii)

wherein $R^6$ is as defined above;
or corresponding boronic ester;
to afford compound of Formula II.

In general, the synthesis pathways for any individual compound of Formula I or Formula II will depend on the specific substituents of each molecule and upon the ready availability of intermediates necessary; again such factors being appreciated by those of ordinary skill in the art.

According to a further general process, compounds of Formula I or II can be converted to alternative compounds of Formula I or II respectively, employing suitable interconversion techniques well known by a person skilled in the art.

Compounds of Formula I or II and related formulae can furthermore be obtained by liberating compounds of Formula I or II from one of their functional derivatives by treatment with a solvolysing or hydrogenolysing agent.

Preferred starting materials for the solvolysis or hydrogenolysis are those which conform to Formula I or II and related formulae, but contain corresponding protected amino and/or hydroxyl groups instead of one or more free amino and/or hydroxyl groups and/or carboxyl groups.

It is also possible for a plurality of—identical or different—protected amino and/or hydroxyl groups to be present in the molecule of the starting material. If the protecting groups present are different from one another, they can in many cases be cleaved off selectively.

Reaction schemes as described in the example section are illustrative only and should not be construed as limiting the invention in any way.

Compounds for Use

The present invention also relates to compounds according to the invention for treating, or for use in treating, diseases or disorders associated with chloride channels, preferably selected from the list comprising, but not limited to, members of the CLC family of Cl-channels such as ClC-1, ClC-2, ClC-3, ClC-5, ClC-7 or ClC-K (a and b), CFTR, TMEM16A (ANO-1) and bestrophin.

Examples of diseases or disorders associated with chloride channels include, without limitation, diseases in muscle, kidney, bone and brain including myotonia congenita, dystrophia myotonica, cystic fibrosis, osteopetrosis, Best's disease, Bartter syndrome, Dent's disease, chronic pancreatitis, bronchiectasis, and epilepsy.

In one embodiment, said chloride channel is CFTR. Examples of diseases or disorders associated with CFTR are, without limitation, cystic fibrosis, chronic pancreatitis, bronchiectasis and congenital bilateral aplasia of vas deferens (CBAVD).

In a first embodiment, said disease or disorder is due to a defect in the chloride channel. In one embodiment, said chloride channel is altered in its maturation and/or structure. In one embodiment, said chloride channel is altered in its function. In one embodiment, said chloride channel is altered both in its maturation and/or structure and in its function.

Examples of causes of maturation and function alterations are, without limitation, mutations of the gene encoding the channel (such as missense or nonsense mutations, insertion or deletion of one or more nucleotides), incorrect transcription of the gene, incorrect translation to the protein or incorrect post-translational modifications, incorrect folding, incorrect membrane traffic and the like.

In one embodiment, said disease or disorder is due to a mutation of one or more nucleotides of the gene encoding the chloride channel.

In another embodiment, said disease or disorder is due to a defect in a protein involved in the chloride channel function. Indeed, posttranslational modifications and interactions with several proteins are main regulatory events affecting activity and stabilizing membrane expression of the CFTR channel (Guggino and Stanton, Nature reviews. Molecular cell biology, 2006, 7(6):426-36). Examples of such defects include, without limitation, misfunction of proteins involved in the maturation of the channel, misfunction of one of the proteins involved in the upstream signaling pathway (such as proteins of the PKA pathway or of the PKC-epsilon pathway, tubulin), or misfunction of one of the proteins involved in the downstream signaling pathway (such as ClCA2, glutathione transporter, sodium channel).

In one embodiment, the present invention provides compounds for treating, or for use in treating, cystic fibrosis.

In one embodiment, said cystic fibrosis is caused by a mutation in the gene encoding the CFTR (cystic fibrosis transmembrane conductance regulator) protein. In one embodiment, the mutation is selected from the group comprising, but not limited to, an insertion, a deletion, a substitution of a residue, a frameshift mutation and a splice-site mutation. The mutation may lead to a shorter protein, a misfolded protein, a misregulation of the channel and/or a reduction of the chloride conductance.

Examples of mutations involved in cystic fibrosis include, without limitation, the insertion W1282, the deletion F508 (F508del), the substitutions G551D, R117H, S549R or A357T, the frameshift mutation L578delTA or the splice-site mutation 3120+1G>A.

In a preferred embodiment, the mutation is a deletion. In a more preferred embodiment, the mutation is F508del.

Therefore, in one embodiment, the compound of the invention is for treating, or for use in treating, cystic fibrosis in a subject with a F508del in the CFTR gene.

Small molecules which facilitate trafficking and delivery of the abnormal protein to the plasma membrane are named correctors, while molecules which improve its channel gating are named potentiators.

In one embodiment, compounds of the invention act as specific correctors of the mutation F508del of CFTR. The person skilled in the art would know how to validate that a compound is a corrector, for example by performing a western blot to determine the maturation state of the mutant protein. In one embodiment, the mutation is homozygous. In another embodiment, the mutation is heterozygous.

Composition, Pharmaceutical Composition and Medicament

The present invention also relates to a composition comprising a compound of the present invention.

In one embodiment the composition is used for treating (or for use in treating) cystic fibrosis.

The present invention also relates to a pharmaceutical composition comprising a compound of the invention and at least one pharmaceutically acceptable excipient.

In one embodiment the pharmaceutical composition as described hereinabove is used for treating (or for use in treating) cystic fibrosis.

The present invention also relates to a medicament comprising a compound of the invention, a composition or a pharmaceutical composition of the present invention.

In one embodiment, the medicament of the invention is used for treating (or for use in treating) cystic fibrosis.

Preferably, the composition, the pharmaceutical composition or the medicament of the invention comprises a therapeutically effective amount of the compound of the invention.

Combination

In one embodiment, the compound of the invention is used in combination with another therapeutic agent for treating CF. In one embodiment, the compound of the invention is in combination with at least one other compound of the invention. In one embodiment, the compound of the invention is in combination with at least one other corrector of F508del. In one embodiment, the compound of the invention is in combination with at least one potentiator of del508 such as VX-770 (Ivacaftor).

Examples of correctors of F508del are, without limitation, VX-809 (Lumacaftor, [3-(6-(1-(2,2-difluorobenzo[d][1,3]dioxol-5-yl)cyclopropanecarboxamido)-3-methylpyridin-2-yl)benzoic acid]), IsoLAB (1,4-dideoxy-2-hydroxymethyl-1,4-imino-1-threitol), miglustat, Corr4a (N-[2-(5-chloro-2-methoxy-phenylamino)-4'-methyl-[4,5']bithiazolyl-2'-yl]-benzamide), suberoylamilide hydroxamic acid (SAHA) and mixtures thereof.

In one embodiment, the compound of the invention is in combination with VX-809. In another embodiment, the compound of the invention is in combination with Isolab. In another embodiment, the compound of the invention is in combination with VX-809 and Isolab.

Dosage

In one embodiment, the therapeutically effective amount ranges from about 10 to about 10000 mg/ml of the composition, pharmaceutical composition or medicament of the invention, preferably 100 to about 5000 mg/ml, more preferably from about 200 to about 2000 mg/ml of the composition, pharmaceutical composition or medicament of the invention.

In one embodiment, the therapeutically effective amount ranges from about 10 to about 10000 mg/g of the composition, pharmaceutical composition or medicament of the invention, preferably 100 to about 5000 mg/g, more preferably from about 200 to about 2000 mg/g of the composition, pharmaceutical composition or medicament of the invention.

It will be understood that the total daily usage of the compound of the invention, composition, pharmaceutical composition and medicament of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from about 10 to about 10000 mg per adult per day, preferably 100 to about 5000, more preferably from about 200 to about 2000 mg per adult per day. Preferably, the compositions contain 10, 50, 100, 250, 500, 1000 and 2,000 mg of the active ingredient for the symptomatic adjustment of the dosage to the patient to be treated. A medicament typically contains from about 10 to about 10000 mg of the active ingredient, preferably 100 to about 5000, more preferably from about 200 to about 2000 mg of the active ingredient. An effective amount of the drug is ordinarily supplied at a dosage level from 0.1 mg/kg to about 100 mg/kg of body weight per day, preferably from about 1 mg/kg to 40 mg/kg of body weight per day, more preferably from about 2 mg/kg to 20 mg/kg of body weight per day.

Administration Route

In the pharmaceutical compositions of the present invention, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

In one embodiment, the composition, pharmaceutical composition or medicament contains vehicles which are pharmaceutically acceptable for a formulation adapted for oral administration.

Examples of forms adapted for oral administration include, but are not limited to, tablets, orodispersing/orodispersing tablets, effervescent tablets, powders, granules, pills (including sugarcoated pills), dragees, capsules (including soft gelatin capsules), syrups, liquids, gels or other drinkable solutions, suspensions, slurries, liposomal forms and the like.

In one embodiment, the composition, pharmaceutical composition or medicament contains vehicles which are pharmaceutically acceptable for a formulation capable of being injected.

Examples of forms adapted for injection include, but are not limited to, solutions, such as, for example, sterile aqueous solutions, dispersions, emulsions, suspensions, solid forms suitable for using to prepare solutions or suspensions upon the addition of a liquid prior to use, such as, for example, powder, liposomal forms and the like.

Method for Treating

The present invention also relates to a method for treating cystic fibrosis in a subject in need thereof comprising administering to the subject a therapeutically effective amount of a compound of the invention as described above.

In one embodiment, a composition, pharmaceutical composition or medicament of the invention is administered to the subject.

The invention will be further illustrated by the following figures and examples. However, these examples and figures should not be interpreted in any way as limiting the scope of the present invention.

Figure 1:
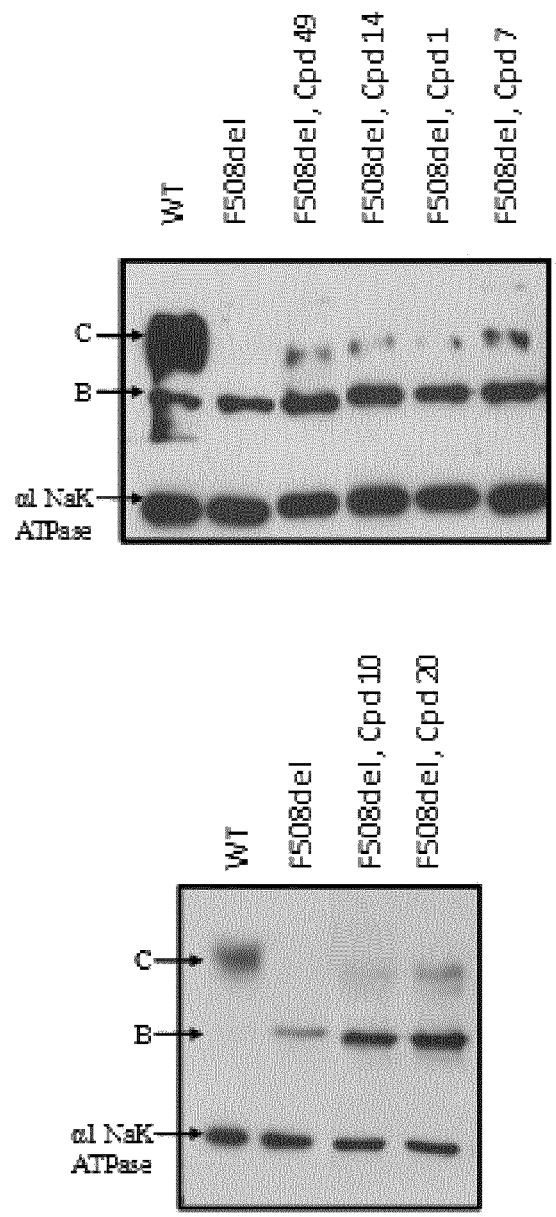
FIG. 1 is a photograph of an immunoblot of F508del-CFTR in presence of compounds of the invention. B represents the B-band and C represents the C-band.

In all figures, the term "Cpd" means compound.

EXAMPLES

The present invention will be better understood with reference to the following examples. These examples are intended to representative of specific embodiments of the invention, and are not intended as limiting the scope of the invention.

I. Chemistry

I.1. Material

All starting materials were commercially available research grade chemicals and used without further purification. They were purchased from Sigma-Aldrich, Fisher, Tokyo Chemical Industry, or Alfa Aesar. Reactions were monitored by analytical TLC on silica gel (Alugram Sil G/UV254) from Macherey-Nagel with fluorescent indicator UV254. LRMS were achieved with a NERMAG spectrometer for the FAB, DCI and EI techniques and with a ZQ Waters for the ESI. HRMS were obtained from the Mass Spectrometry Service of ICOA, at the University of Orléans, France. $^1$H NMR spectra were recorded on a Bruker Avance 400 at 400 MHz using the residual solvent signal as internal standard. Chemical shifts are reported in ppm (parts per million) relative to the residual signal of the solvent, and the signals are described as singlet (s), broad singlet (bs), doublet (d), triplet (t), doublet of doublet (dd), quartet (q), sextuplet (sext), septuplet (sept), multiplet (m); coupling constants are reported in Hertz (Hz). Columns chromatography were performed on silica gel (MN Kieselgel 60, 0.063e0.2 mm/70e230 mesh, Machereye-Nagel) or on C18 reversed phase (Macherey-Nagel Polygoprep 60e50 C18). Flash chromatography were performed on Grace Reveleris apparatus using Grace Flash Cartridges.

I.2. General Methods of Synthesis

General synthesis protocol I. To a solution of copper(II) acetate (1 to 2 equivalents) in DMF (5 to 10 mL/mmol) were successively added the purine derivative (1 equivalent), boronic acid derivative (1 to 2 equivalents), triethylamine (2 equivalents) and eventually molecular sieves 3 Å. The solution was stirred for 24 to 96 h, then concentrated under reduced pressure.

A saturated aqueous solution of ethylenediaminetetraacetic acid (EDTA) was added and the resulting mixture was extracted with dichloromethane or ethyl acetate. The organic layer was washed with water and brine, then dried over magnesium sulfate. After filtration and concentration under reduced pressure the crude product was purified by chromatography on silica gel to afford the pure compound.

General synthesis protocol II. To a solution of the purine derivative (1 equivalent) dissolved in the amine derivative (20 equivalents) was added p-toluenesulfonic acid (0.1 equivalent). The solution was stirred for 5 min under microwave irradiation at 180° C. The crude product in solution in the amine derivative was purified by chromatography on silica gel.

General synthesis protocol III. A solution of the purine derivative in TFA (10 mL/mmol) was refluxed for 24 h and then concentrated under reduced pressure. The crude product was purified by precipitation or by chromatography on silica gel.

General synthesis protocol IV. To a suspension of purine derivative in THF (2 mL/mmol) were added TBAF (1 M in THF, 2 equivalents) and the aryl bromide derivative (2 equivalents). The resulting solution was stirred for 10 to 60 min, and then concentrated under reduced pressure. The crude product was purified by precipitation or by chromatography on silica gel.

General synthesis protocol V. To a solution of the purine derivative in DMF (2 mL/mmol) were added aryl bromide derivative (1.1 equivalent) and $K_2CO_3$ (1.1 equivalent). The resulting suspension was stirred for 16 h, then the solid was filtrated and washed with methanol. The filtrate was concentrated under reduced pressure. The crude product was purified by chromatography on silica gel.

General synthesis protocol VI. To a solution of the purine derivative in dichloromethane (40 mL/mmol) was added TFA (10 mL/mmol). The solution was stirred for 16 h, and then concentrated under reduced pressure. The crude product was purified by precipitation and by washing with water or by chromatography on silica gel.

General synthesis protocol VII. To a solution of the purine derivative (1 equivalent) in DMF (20 mL/mmol) were added amino acid ester (1.5 equivalent) and triethylamine (3 equivalents). The solution was stirred for 8 h at 80° C., and then was concentrated under reduced pressure. The crude residue was dissolved in dichloromethane and purified by extraction with water, by precipitation or by chromatography on silica gel to afford pure compound.

General synthesis protocol VIII. To a solution of purine derivative (1 equivalent) in water (10 mL/mmol) were added the amino acid (6 equivalents) and $K_2CO_3$ (6 equivalents). The solution was stirred for 8 h at 70° C. After cooling to room temperature, the solution was neutralized by addition of aqueous hydrochloric acid (5%). The resulting solution was purified by extraction with dichloromethane and then the aqueous layer was concentrated under reduced pressure. The crude residue was purified by reverse phase chromatography eluting with water/methanol.

General synthesis protocol IX. To a solution of the purine derivative in acetonitrile (0.3 mL/mmol) or in a mixture methanol/dichloromethane (1/1 v/v, 0.3 mL/mmol) were added $NaBH_3CN$ (6 equivalents) and the corresponding aldehyde (8 equivalents). The solution was stirred for 3 days at room temperature and then concentrated under reduced pressure. The crude product was purified by chromatography on silica gel.

General synthesis protocol X. To a solution of the chloropyrimidine derivative in a mixture water/dioxane (1/1 v/v, 4 mL/mmol) were added the amine (1 equivalent) and $Na_2CO_3$ (2 equivalents). The solution was refluxed overnight. After concentration under reduced pressure, the crude product was purified by precipitation.

General synthesis protocol XI. To a suspension of the pyrimidine derivative in a mixture of dichloromethane/aqueous acetic acid (37%) (1/1 v/v, 10 mL/mmol) was added $NaNO_2$ (1.1 equivalent). The suspension was stirred for 30 min at room temperature and then methanol (10 mL/mmol) was added. The suspension was stirred for 24 h at room temperature and the resulting precipitate was filtrated and washed with methanol to afford the pure product.

General synthesis protocol XII. To a suspension of the pyrimidine derivative in trimethyl orthoformate (5 mL/mmol) was added ethanesulfonic acid (25 μL/mmol). The suspension was stirred for 1 h under microwave irradiation at 120° C. The resulting precipitate was filtrated and washed with methanol to afford the pure product.

General synthesis protocol XIII. To a suspension of the purine derivative in the alcohol derivative (2.5 mL/mmol) was added NaOH (250 mg/mmol). The suspension was stirred for 3 h at 85° C. The crude product in solution in the alcohol derivative was purified by chromatography on silica gel to afford the pure product.

General synthesis protocol XIV. To a suspension of the purine derivative in absolute ethanol (30 mL/mmol) was added aqueous hydrochloric acid (10%, v/v, 3 mL/mmol). The suspension was stirred for 24 h at room temperature and then the solvents were removed under reduced pressure to afford the pure product.

General synthesis protocol XV. To a solution of the chloropyrimidine derivative in a mixture water/dioxane (1/1 v/v, 4 mL/mmol) was added the amine (3 equivalent). The solution was refluxed overnight. After cooling at room temperature, the crude product was purified by precipitation.

General synthesis protocol XVI. To a solution of the nitrochloropyrimidine derivative in tetrahydrofuran (4 mL/mmol) were added the amine (1 equivalent) and $NaHCO_3$ (1.1 equivalents). The solution was stirred at room temperature overnight. After concentration under reduced pressure, the crude product was purified by chromatography on silica gel to afford the pure product.

General synthesis protocol XVII. To a solution of the chloropyrimidine derivative in a mixture water/dioxane (1/1 v/v, 2 mL/mmol) was added the amine (1 or 2 equivalents) and paratoluenesulfonic acid (0.5). The solution was refluxed overnight. After cooling at room temperature, the crude product was purified by precipitation.

I.3. Synthesis of Intermediates

Intermediate Int-1. This compound was synthesized through general synthesis protocol I from compound 9 and phenylboronic acid, and was purified by chromatography on silica gel (eluent dichloromethane/methanol) to afford pure compound Int-1 (42%). $^1$H NMR (400 MHz, $CDCl_3$) δ 7.99 (s, 1H, $CH_{Ar}$), 7.68-7.62 (m, 2H, 2 $CH_{Ar}$), 7.60-7.54 (m, 2H, 2 $CH_{Ar}$), 7.49-7.43 (m, 1H, $CH_{Ar}$), 7.38-7.32 (m, 2H, 2 $CH_{Ar}$), 6.93-6.88 (m, 2H, 2 $CH_{Ar}$), 6.35 (bs, 1H, NH), 4.79 (bs, 2H, $CH_2$), 3.82 (s, 3H, $CH_3$); HRMS (ESI) calc. for $C_{19}H_{17}ClN_5O$: $[M+H]^+$ 366.11194, found 366.1116.

Intermediate Int-2. This compound was synthesized through general synthesis protocol I from 2,6-dichloropurine and 4-(hydroxymethyl)phenylboronic acid, and was purified by chromatography on silica gel (eluent dichloromethane/methanol) to afford pure compound Int-2 (7%). $^1$H NMR (400 MHz, $CDCl_3$) δ 8.37 (s, 1H, $CH_{Ar}$), 7.74-7.64 (m, 2H, 2 $CH_{Ar}$), 7.64-7.58 (m, 2H, 2 $CH_{Ar}$), 4.83 (s, 2H, $CH_2$), 1.85 (bs, 1H, OH); HRMS (ESI) calc. for $C_{12}H_9Cl_2N_4O$: $[M+H]^+$ 295.01479, found 295.0150.

Intermediate Int-3. This compound was synthesized through general synthesis protocol V from 2,6-dichloropurine and benzyle bromide, to afford pure compound Int-3 (19%). $^1$H NMR (400 MHz, $CDCl_3$) δ 8.04 (s, 1H, $CH_{Ar}$), 7.45-7.36 (m, 3H, 3 $CH_{Ar}$), 7.34-7.29 (m, 2H, 2 $CH_{Ar}$), 5.41 (s, 2H, $CH_2$); HRMS (ESI) calc. for $C_{12}H_9Cl_2N_4$: $[M+H]^+$, 279.01988, found 279.0201.

Intermediate Int-4. This compound was synthesized through general synthesis protocol VII from compound Int-3 and L-alanine tert-butyl ester, was purified by extraction dichloromethane/water and then by chromatography on silica gel (eluent dichloromethane/methanol) to afford pure compound Int-4 (47%). $^1$H NMR (400 MHz, $CDCl_3$) δ 7.65 (s, 1H, $CH_{Ar}$), 7.42-7.32 (m, 3H, 3 $CH_{Ar}$), 7.29-7.24 (m, 2H, 2 $CH_{Ar}$), 6.41 (bs, 1H, NH), 5.31 (s, 2H, $CH_2$), 4.81 (bs, 1H, CH), 1.53 (d, J=7.1 Hz, 3H, $CH_3$), 1.48 (s, 9H, $CH_3$); HRMS (ESI) calc. for $C_{19}H_{23}ClN_5O_2$: $[M+H]^+$ 388.15348, found 388.1538.

Intermediate Int-5. This compound was synthesized through general synthesis protocol II from compound Int-4 and 3-phenylpropyl-1-amine, and was purified by chromatography on silica gel (eluent dichloromethane/ethyl acetate) to afford pure compound Int-5 (75%). $^1$H NMR (400 MHz, $CDCl_3$) δ 7.46 (s, 1H, $CH_{Ar}$), 7.40-7.30 (m, 8H, 8 $CH_{Ar}$), 7.27-7.21 (m, 2H, 2 $CH_{Ar}$), 6.05 (bs, 1H, NH), 5.23 (s, 2H, $CH_2$), 4.98-4.90 (m, 1H), 4.81 (bs, 1H, CH), 3.63-3.43 (m, 2H, $CH_2$), 2.80-2.74 (m, 2H, $CH_2$), 2.06-1.95 (m, 2H, $CH_2$), 1.55 (d, J=7.1 Hz, 3H, $CH_3$), 1.52 (s, 9H, 3 $CH_3$); HRMS (ESI) calc. for $C_{28}H_{35}N_6O_4$: $[M+H]^+$ 487.28160, found 487.2811.

Intermediate Int-6. This compound was synthesized through general synthesis protocol I from 6-diBoc-adenine and 4-carbamoylphenylboronic acid, and was purified by chromatography on silica gel (elution with dichloromethane/methanol) to afford pure compound Int-6 (39%). $^1$H NMR (400 MHz, $CDCl_3$) δ 8.95 (s, 1H, $CH_{Ar}$), 8.42 (s, 1H, $CH_{Ar}$), 8.06 (d, J=8.7 Hz, 2H, 2 $CH_{Ar}$), 7.92 (d, J=8.7 Hz, 2H, 2 $CH_{Ar}$), 6.12 (bs, 1H, NH), 5.76 (bs, 1H, NH), 1.50 (s, 18H, 6 $CH_3$); HRMS (ESI) calc. for $C_{22}H_{27}N_6O_5$: $[M+H]^+$ 455.20374, found 455.2033.

Intermediate Int-7. To a solution of 2,6-dichloropurine in ethyl acetate (3 mL/mmol) was added para-toluenesulfonic acid (2 mg/mmol). The solution was stirred at 50° C., and a solution of 3,4-dihydropyrane (1.3 equivalent) in ethyl acetate (0.5 mL/mmol) was added for 30 min. The solution was stirred at 50° C. for 15 min, cooled to room temperature, washed with water and brine. The organic layer was evaporated under reduced pressure to afford pure compound Int-7 (99%). $^1$H NMR (400 MHz, $d_6$-DMSO) δ 8.95 (s, 1H, $CH_{Ar}$), 5.74 (dd, J=10.8 Hz, J=2.2 Hz, 1H, CH), 4.02 (m, 1H, CH), 3.74 (m, 1H, CH), 2.26 (m, 1H, CH), 1.98 (m, 2H, CH$_2$), 1.43-1.75 (m, 3H, CH+CH$_2$); HRMS (ESI) calc. for C$_{10}$H$_{11}$Cl$_2$N$_4$O: [M+H]$^+$ 273.03044, found 273.0303.

Intermediate Int-8. This compound was synthesized through general synthesis protocol II from compound 15 and 3-phenylpropyl-1-amine, and was purified by chromatography on silica gel (eluent dichloromethane/ethyl acetate) to afford pure compound Int-8 (87%). $^1$H NMR (400 MHz, CDCl$_3$) δ 7.68 (s, 1H, CH$_{Ar}$), 7.65 (d, J=8.4 Hz, 2H, 2 CH$_{Ar}$), 7.48 (d, J=8.4 Hz, 2H, 2 CH$_{Ar}$), 7.36-7.27 (m, 2H, 2 CH$_{Ar}$), 7.25-7.20 (m, 3H, 3 CH$_{Ar}$), 6.27 (bs, 1H, NH), 5.12-5.00 (m, 1H, CH), 4.75 (s, 2H, CH$_2$), 3.59-3.38 (m, 2H, CH$_2$), 2.78-2.71 (m, 2H, CH$_2$), 2.02-1.92 (m, 2H, CH$_2$), 1.57 (d, J=7.1 Hz, 3H, CH$_3$), 1.53 (s, 9H, 3 CH$_3$); HRMS (ESI) calc. for C$_{28}$H$_{35}$N$_6$O$_3$: [M+H]$^+$ 503.27652, found 503.2767.

Intermediate Int-9. This compound was synthesized through general synthesis protocol X from 4-aminobenzamide and 2,5-diamino-4,6-dichloropyrimidine to afford pure compound Int-9 (97%). $^1$H NMR (400 MHz, d$_6$-DMSO) δ 9.28 (bs, 1H, NH), 7.89 (d, J=8.9 Hz, 2H, 2 CH$_{Ar}$), 7.84 (d, J=8.9 Hz, 2H, 2 CH$_{Ar}$), 7.24 (bs, 1H, NH$_2$), 4.81 (bs, 5H, NH$_2$); HRMS (ESI) calc. for C$_{11}$H$_{12}$ClN$_6$O: [M+H]$^+$ 279.07556, found 279.0755.

Intermediate Int-10. This compound was synthesized through general synthesis protocol XII from compound Int-9 (11%). $^1$H NMR (400 MHz, d$_6$-DMSO) δ 8.62 (s, 1H, CH$_{Ar}$), 8.09 (bs, 1H, NH$_2$), 8.06 (d, J=8.7 Hz, 2H, 2 CH$_{Ar}$), 7.98 (d, J=8.7 Hz, 2H, 2 CH$_{Ar}$), 7.50 (bs, 1H, NH$_2$), 7.10 (s, 2H, NH$_2$); HRMS (ESI) calc. for C$_{12}$H$_{10}$ClN$_6$O: [M+H]$^+$ 289.05991, found 289.0599.

Intermediate Int-11. Compound 106 (1 equivalent) was suspended in NH$_4$OH 30% (20 mL/mmol), heated to 40° C. for 40 min, concentrated and the resulting solid was suspended in boiling methanol (50 mL) then filtrated. This operation was done twice to afford pure compound Int-11 as an orange solid (59%). $^1$H NMR (400 MHz, d$_6$-DMSO) δ 10.89 (bs, 1H, NH), 8.69 (bs, 2H, NH$_2$), 8.08 (s, 1H, CH$_{Ar}$), 7.94 (bs, 1H, NH$_2$), 7.88 (d, J=8.1 Hz, 2H, 2 CH$_{Ar}$), 7.74 (d, J=8.1 Hz, 2H, 2 CH$_{Ar}$), 7.33 (bs, 1H, NH$_2$); HRMS (ESI) calc. for C$_{11}$H$_{11}$N$_6$O$_3$: [M+H]$^+$ 275.08871, found 275.0889.

I.4. Synthesis of Compounds

Compounds 8, 29, 31, 32, II-1 and II-2 were synthesized through specific protocol described hereafter.

Compound 1. This compound was synthesized through general synthesis protocol V from adenine and 1-bromo-3-phenylpropane, and was purified by chromatography on silica gel (elution with dichloromethane/methanol) to afford pure compound 1 (57%). $^1$H NMR (400 MHz, CDCl$_3$) δ 8.39 (bs, 1H, CH$_{Ar}$), 7.76 (bs, 1H, CH$_{Ar}$), 7.36-7.14 (m, 5H, 5 CH$_{Ar}$), 5.63 (bs, 2H, NH$_2$), 4.23 (t, J=7.2 Hz, 2H, CH$_2$), 2.69 (t, J=7.3 Hz, 2H, CH$_2$), 2.28 (m, 2H, CH$_2$); MS (ESI [+]) m/z 254 [M+H]$^+$.

Compound 2. This compound was synthesized through general synthesis protocol III from compound 4, and was purified by chromatography on silica gel (elution with dichloromethane/methanol) to afford pure compound 2 (50%). $^1$H NMR (400 MHz, d$_6$-DMSO) δ 8.25 (s, 1H, CH$_{Ar}$), 7.78 (bs, 2H, NH$_2$), 7.26-7.38 (m, 5H, 5 CH$_{Ar}$), 5.33 (s, 2H, CH$_2$); HRMS (ESI) calc. for C$_{12}$H$_{11}$ClN$_5$: [M+H]$^+$ 260.06975, found 260.0703.

Compound 3. This compound was synthesized through general synthesis protocol III from compound 5, and was purified by chromatography on silica gel (elution with dichloromethane/methanol) to afford pure compound 3 (98%). $^1$H NMR (400 MHz, d$_6$-DMSO) δ 8.04 (s, 1H, CH$_{Ar}$), 7.78 (bs, 1H, NH), 7.35-7.15 (m, 10H, CH$_{Ar}$), 7.06 (bs, 2H, NH$_2$), 5.20 (bs, 2H, CH$_2$), 2.67-2.59 (m, 2H, CH$_2$), 1.90-1.80 (m, 2H, CH$_2$); HRMS (ESI) calc. for C$_{21}$H$_{23}$N$_6$: [M+H]$^+$ 359.19787, found 359.1979.

Compound 4. This compound was synthesized through general synthesis protocol IV from compound 9 benzyle bromide, and was purified by precipitation in methanol to afford pure compound 4 (78%). $^1$H NMR (400 MHz, CDCl$_3$) δ 7.59 (s, 1H, CH$_{Ar}$), 7.28-7.37 (m, 7H, 7 CH$_{Ar}$), 6.88 (d, J=8.7 Hz, 2H, 2 CH$_{Ar}$), 6.22 (bs, 1H, NH), 5.32 (s, 2H, CH$_2$), 4.75 (bs, 2H, CH$_2$), 3.81 (s, 3H, CH$_3$); HRMS (ESI) calc. for C$_{20}$H$_{19}$ClN$_5$O: [M+H]$^+$ 380.12726, found 380.1281.

Compound 5. This compound was synthesized through general synthesis protocol II from compound 4 and 3-phenylpropyl-1-amine, and was purified by precipitation in methanol to afford pure compound 5 (67%). $^1$H NMR (400 MHz, CDCl$_3$) δ 7.38 (s, 1H, CH$_{Ar}$), 7.15-7.35 (m, 12H, 12 CH$_{Ar}$), 6.86 (d, J=8.6 Hz, 2H, 2 CH$_{Ar}$), 5.74 (bs, 1H, NH), 5.20 (s, 2H, CH$_2$), 4.87 (bs, 1H, NH), 4.71 (bs, 2H, CH$_2$), 3.80 (s, 3H, CH$_3$), 3.50 (q, J=7.0 Hz, 2H, CH$_2$), 2.73 (t, J=7.0 Hz, 2H, CH$_2$), 1.96 (quint., J=7.0 Hz, 2H, CH$_2$); HRMS (ESI) calc. for C$_{29}$H$_{31}$N$_6$O: [M+H]$^+$ 479.25539, found 479.2553.

Compound 6. This compound was synthesized through general synthesis protocol VI from compound Int-5 to afford pure compound 6 (99%). $^1$H NMR (400 MHz, CD$_3$OD) δ 7.72 (bs, 1H, CH$_{Ar}$), 7.32-7.10 (m, 10H, 10 CH$_{Ar}$), 5.22 (s, 2H, CH$_2$), 4.71 (bs, 1H, CH), 3.39 (t, J=7.0 Hz, 2H, CH$_2$), 2.70-2.62 (m, 2H, CH$_2$), 1.96-1.84 (m, 2H, CH$_2$), 1.55 (d, J=7.1 Hz, 3H, CH$_3$); HRMS (ESI) calc. for C$_{24}$H$_{27}$N$_6$O$_2$: [M+H]$^+$ 431.21900, found 431.2195.

Compound 7. This compound was synthesized through general synthesis protocol III from compound 10, and was purified by chromatography on silica gel (elution with dichloromethane/methanol) to afford pure compound 7 (79%). $^1$H NMR (400 MHz, d$_6$-DMSO, 60° C.) δ 8.05 (s, 1H, CH$_{Ar}$), 7.94 (bs, 2H, NH$_2$), 7.16-7.30 (m, 5H, 5 CH$_{Ar}$), 3.36 (t, J=7.0 Hz, 2H, CH$_2$), 2.66 (t, J=7.0 Hz, 2H, CH$_2$), 1.89 (quint., J=7.0 Hz, 2H, CH$_2$); HRMS (ESI) calc. for C$_{14}$H$_{17}$N$_6$: [M+H]$^+$ 269.15092, found 269.1507.

Compound 8. To a solution of 2,6-dichloropurine (1 equivalent) in DMF (4 mL/mmol) were added 3-phenylpropylamine (1.2 equivalent) and diisopropylethylamine (2 equivalents). The solution was stirred for 6 h at 80° C., and then evaporated under reduced pressure. The crude product was dissolved in dichloromethane and purified by extraction with water to afford pure compound 8 (37%). $^1$H NMR (400 MHz, d$_6$-DMSO) δ 12.95 (s, 1H, NH), 8.16 (bs, 1H, NH), 8.11 (s, 1H, CH$_{Ar}$), 7.33-7.12 (m, 5H, 5 CH$_{Ar}$), 3.44 (s, 2H, CH$_2$), 2.69-2.61 (m, 2H, CH$_2$), 1.97-1.83 (m, 2H, CH$_2$); HRMS (ESI) calc. for C$_{14}$H$_{15}$ClN$_5$: [M+H]$^+$ 288.10105, found 288.1011.

Compound 9. To a solution of 2,6-dichloropurine in DMF (1.5 mL/mmol) were added 4-methoxybenzylamine (1.1 equivalent) and triethylamine (2 equivalents). The solution was stirred overnight at 80° C. After concentration under reduced pressure, the crude product was purified by precipitation in dichloromethane to afford pure compound 9 (95%). $^1$H NMR (400 MHz, d$_6$-DMSO) δ 13.06 (bs, 1H, NH), 8.62 (bs, 1H, NH), 8.12 (s, 1H, CH$_{Ar}$), 7.28 (d, J=8.3 Hz, 2H, 2 CH$_{Ar}$), 6.88 (d, J=8.3 Hz, 2H, 2 CH$_{Ar}$), 5.08 (bs, 0.4H, CH$_2$); 4.56 (s, 1.6H, CH$_2$), 3.71 (s, 3H, CH$_3$); HRMS (ESI) calc. for C$_{13}$H$_{13}$ClN$_5$O: [M+H]$^+$ 290.08077, found 290.0803.

Compound 10. This compound was synthesized through general synthesis protocol II from compound 9 and 3-phenylpropyl-1-amine, and was purified by chromatography on silica gel (elution with dichloromethane/methanol) to afford pure compound 10 (6%). $^1$H NMR (400 MHz, d$_6$-DMSO) δ

12.12 (bs, 1H, NH), 7.62 (s, 1H, $CH_{Ar}$), 7.59 (bs, 1H, NH), 7.14-7.28 (m, 7H, 7 $CH_{Ar}$), 6.82 (d, J=8.5 Hz, 2H, 2 $CH_{Ar}$), 6.25 (bs, 1H, NH), 4.54 (bs, 2H, $CH_2$), 3.69 (s, 3H, $OCH_3$), 3.23 (q, J=7.0 Hz, 2H, $CH_2$), 2.60 (t, J=7.0 Hz, 2H, $CH_2$), 1.80 (quint., J=7.0 Hz, 2H, $CH_2$); HRMS (ESI) calc. for $C_{22}H_{25}N_6O$: [M+H]+ 389.20844, found 389.2092.

Compound 11. This compound was synthesized through general synthesis protocol XIV from compound 99 (35%). $^1H$ NMR (400 MHz, $d_6$-DMSO) δ 9.15 (bs, 1H, NH), 8.46 (s, 1H, $CH_{Ar}$), 7.16-7.31 (m, 7H, 7 $CH_{Ar}$), 6.88 (d, J=8.7 Hz, 2H, 2 $CH_{Ar}$), 4.63 (s, 2H, $CH_2$), 4.35 (s, 2H, $CH_2$), 3.72 (s, 3H, $CH_3$), 2.71 (m, 2H, $CH_2$), 2.03 (m, 2H, $CH_2$); HRMS (ESI) calc. for $C_{22}H_{24}N_5O_2$: [M+H]+ 390.19245, found 390.1922.

Compound 12. This compound was synthesized through general synthesis protocol XIV from compound 98 (100%). $^1H$ NMR (400 MHz, $d_6$-DMSO) δ 9.36 (bs, 1H, NH), 8.56 (s, 1H, $CH_{Ar}$), 7.21-7.33 (m, 7H, 7 $CH_{Ar}$), 6.89 (d, J=8.7 Hz, 2H, 2 $CH_{Ar}$), 4.67 (bs, 2H, $CH_2$), 4.57 (t, J=6.9 Hz, 2H, $CH_2$), 3.72 (s, 3H, $CH_3$), 3.04 (t, J=6.9 Hz, 2H, $CH_2$); HRMS (ESI) calc. for $C_{21}H_{22}N_5O_2$: [M+H]+ 376.17680, found 376.1769.

Compound 14. This compound was obtained in two steps through general synthesis protocol VII from compound Int-2 and 1-alanine tert-butyl ester (purification by extraction dichloromethane/water) then through general synthesis protocol VI to afford pure compound 14 (64%). $^1H$ NMR (400 MHz, $CD_3OD$) δ 8.39 (s, 1H, $CH_{Ar}$), 7.74 (d, J=8.4 Hz, 2H, 2 $CH_{Ar}$), 7.60 (d, J=8.6 Hz, 2H, 2 $CH_{Ar}$), 4.72 (s, 2H, $CH_2$), 1.61 (t, J=7.0 Hz, 3H, $CH_3$); HRMS (ESI) calc. for $C_{15}H_{15}ClN_5O_3$: [M+H]+ 348.08579, found 348.0856.

Compound 15. This compound was synthesized through general synthesis protocol VII from compound Int-2 and 1-alanine tert-butyl ester, and was purified by extraction to afford pure compound 15 (97%). $^1H$ NMR (400 MHz, $CDCl_3$) δ 8.02 (s, 1H, $CH_{Ar}$), 7.64 (d, J=8.5 Hz, 2H, 2 $CH_{Ar}$), 7.55 (d, J=8.5 Hz, 2H, 2 $CH_{Ar}$), 6.48 (bs, 1H, NH), 4.83 (bs, 1H, CH), 4.78 (s, 2H, $CH_2$), 1.57 (d, J=7.0 Hz, 3H, $CH_3$), 1.50 (s, 9H, 3 $CH_3$); HRMS (ESI) calc. for $C_{19}H_{23}ClN_5O_3$: [M+H]+ 404.14839, found 404.1487.

Compound 16. This compound was synthesized through general synthesis protocol XII from compound 49 (56%). $^1H$ NMR (400 MHz, $d_6$-DMSO) δ 9.20 (s, 1H, $CH_{Ar}$), 8.89 (s, 1H, $CH_{Ar}$), 8.13 (bs, 1H, NH), 8.12 (d, J=8.7 Hz, 2H, 2 $CH_{Ar}$), 8.05 (d, J=8.7 Hz, 2H, 2 $CH_{Ar}$), 7.54 (bs, 1H, NH); HRMS (ESI) calc. for $C_{12}H_9ClN_5O$: [M+H]+ 274.04901, found 274.0487.

Compound 17. This compound was obtained by addition of triethylamine on compound 79 during reaction through general synthesis protocol I. It was purified by extraction dichloromethane/water and then by chromatography on silica gel (elution with dichloromethane/methanol) to afford pure compound 17 (1%). $^1H$ NMR (400 MHz, $d_6$-DMSO) δ 8.63 (s, 1H, $CH_{Ar}$), 8.13-8.05 (m, 3H, 2 $CH_{Ar}$+NH), 7.90 (d, J=8.7 Hz, 2H, 2 $CH_{Ar}$), 7.51 (s, 1H, NH), 4.21 (bs, 2H, $CH_2$), 3.69 (bs, 2H, $CH_2$), 1.24 (bs, 6H, 2 $CH_3$); HRMS (ESI) calc. for $C_{16}H_{18}ClN_6O$: [M+H]+ 345.12251, found 345.1223.

Compound 18. This compound was synthesized through general synthesis protocol III from compound 25, and was purified by precipitation in a mixture dichloromethane and methanol to afford pure compound 18 (87%). $^1H$ NMR (400 MHz, $d_6$-DMSO) δ 8.65 (s, 1H, $CH_{Ar}$), 8.10 (bs, 1H, NH), 8.07 (d, J=8.7 Hz, 2H, 2 $CH_{Ar}$), 7.94 (bs, 2H, $NH_2$), 7.93 (d, J=8.7 Hz, 2H, 2 $CH_{Ar}$), 7.50 (bs, 1H, NH); HRMS (ESI) calc. for $C_{12}H_{10}ClN_6O$: [M+H]+ 289.05991, found 289.0602.

Compound 19. This compound was synthesized through general synthesis protocol VI from compound Int-6 to afford pure compound 19 (99%). $^1H$ NMR (400 MHz, $d_6$-DMSO) δ 8.83 (s, 1H, $CH_{Ar}$), 8.41 (bs, 3H, 2 $CH_{Ar}$+$NH_2$), 8.19-8.06 (m, 3H, $CH_{Ar}$+NH), 8.00 (d, J=8.7 Hz, 2H, 2 $CH_{Ar}$), 7.53 (bs, 1H, NH); HRMS (ESI) calc. for $C_{12}H_{11}N_6O$: [M+H]+ 255.09888, found 255.0985.

Compound 20. This compound was obtained in two steps through general synthesis protocol I and VI from 2,6-bis (diBoc)-diaminopurine, and purified by precipitation in dichloromethane to afford pure compound 20 (4%). $^1H$ NMR (400 MHz, $d_6$-DMSO) δ 8.58 (bs, 2H, $NH_2$), 8.47 (s, 1H, $CH_{Ar}$), 8.10 (bs, 1H, NH), 8.06 (d, J=8.6 Hz, 2H, 2 $CH_{Ar}$), 7.91 (d, J=8.6 Hz, 2H, 2 $CH_{Ar}$), 7.52 (bs, 1H, NH), 7.24 (bs, 2H, $NH_2$); HRMS (ESI) calc. for $C_{12}H_{12}N_7O$: [M+H]+ 270.10978, found 270.1096.

Compound 21. This compound was synthesized through general synthesis protocol VII from compound 79 and 2-aminopropane-1,3-diol to afford pure compound 21 (87%). $^1H$ NMR (400 MHz, $d_6$-DMSO, 60° C.) δ 8.60 (s, 1H, $CH_{Ar}$), 8.12-8.05 (m, 2H, 2 $CH_{Ar}$), 7.99-7.69 (m, 3H, 2 $CH_{Ar}$+NH), 7.51 (d, J=8.6 Hz, 1H, NH), 7.31 (bs, 1H, NH), 4.59 (t, J=5.3 Hz, 2H, 2 OH), 4.31 (bs, 1H, CH), 3.64 (t, J=5.7 Hz, 4H, $CH_2$); HRMS (ESI) calc. for $C_{15}H_{16}ClN_6O_3$: [M+H]+ 363.09669, found 363.0967.

Compound 22. This compound was synthesized through general synthesis protocol VIII from compound 79 and 1-serine to afford pure compound 22 (82%). $^1H$ NMR (400 MHz, $D_2O$) δ 7.86 (s, 1H, $CH_{Ar}$), 7.34 (d, J=8.1 Hz, 2H, 2 $CH_{Ar}$), 7.08 (d, J=8.1 Hz, 2H, 2 $CH_{Ar}$), 4.28 (bs, 1H, CH), 3.90 (bs, 2H, $CH_2$); HRMS (ESI) calc. for $C_{15}H_{14}ClN_6O_4$: [M+H]+ 377.07608, found 377.0759.

Compound 23. This compound was synthesized in two steps through general synthesis protocol VII from compound 79 and glycine tert-butyl ester (purification by extraction dichloromethane/water) and through general synthesis protocol VI to afford pure compound 23 (68%). $^1H$ NMR (400 MHz, $d_6$-DMSO) δ 12.71 (bs, 1H, COOH), 8.70 (s, 1H, $CH_{Ar}$), 8.64 (bs, 0.8H, NH), 8.46 (bs, 0.2H, NH), 8.14-8.04 (m, 3H, 2 $CH_{Ar}$+NH), 7.93 (d, J=8.6 Hz, 2H, 2 $CH_{Ar}$), 7.51 (s, 1H, NH), 4.56 (d, J=6.5 Hz, 0.4H, $CH_2$), 4.11 (d, J=6.1 Hz, 1.6H, $CH_2$); HRMS (ESI) calc. for $C_{14}H_{12}ClN_6O_3$: [M+H]+ 347.06539, found 347.0651.

Compound 24. This compound was synthesized through general synthesis protocol VII from compound 79 and glycine tert-butyl ester, and was purified by chromatography on silica gel (elution with dichloromethane/methanol) to afford pure compound 24 (69%). $^1H$ NMR (400 MHz, $d_6$-DMSO, 60° C.) δ 8.63 (s, 1H, $CH_{Ar}$), 8.45 (bs, 1H, NH), 8.10-8.06 (m, 2H, 2 $CH_{Ar}$), 7.93 (d, J=8.6 Hz, 3H, 2 $CH_{Ar}$+NH), 7.32 (bs, 1H, NH), 4.09 (bs, 2H, $CH_2$), 1.44 (s, 9H, 3 $CH_3$); HRMS (ESI) calc. for $C_{18}H_{20}ClN_6O_3$: [M+H]+ 403.12799, found 403.1279.

Compound 25. This compound was synthesized through general synthesis protocol I from compound 9 and 4-carbamoylphenylboronic acid, and was purified by chromatography on silica gel (elution with dichloromethane/methanol) to afford pure compound 25 (7%). $^1H$ NMR (400 MHz, $d_6$-DMSO) δ 8.96 (t, J=6.0 Hz, 1H, NH), 8.66 (s, 1H, $CH_{Ar}$), 8.09 (s, 1H, NH), 8.08 (d, J=8.7 Hz, 2H, 2 $CH_{Ar}$), 7.92 (d, J=8.5 Hz, 2H, 2 $CH_{Ar}$), 7.50 (s, 1H, NH), 7.30 (d, J=8.5 Hz, 2H, 2 $CH_{Ar}$), 6.89 (d, J=8.7 Hz, 2H, 2 $CH_{Ar}$), 4.60 (d, J=6.0 Hz, 2H, $CH_2$), 3.72 (s, 3H, $CH_3$); HRMS (ESI) calc. for $C_{20}H_{18}ClN_6O_2$: [M+H]+ 409.11743, found 409.1179.

Compound 26. This compound was synthesized through general synthesis protocol VI from compound 27 to afford pure compound 26 (99%). $^1H$ NMR (400 MHz, $CD_3OD$) δ

8.51 (bs, 1H, CH$_{Ar}$), 8.17-8.07 (m, 2H, 2 CH$_{Ar}$), 8.01-7.91 (m, 2H, 2 CH$_{Ar}$), 1.63 (d, J=7.3 Hz, 3H, CH$_3$); HRMS (ESI) calc. for C$_{15}$H$_{14}$ClN$_6$O$_3$: [M+H]$^+$ 361.08104, found 361.0809.

Compound 27. This compound was synthesized through general synthesis protocol VII from compound 79 and 1-alanine tert-butyl ester, and was purified by extraction to afford pure compound 27 (61%). $^1$H NMR (400 MHz, CD$_3$OD) δ 8.51 (bs, 1H, CH$_{Ar}$), 8.51 (d, J=8.6 Hz, 2H, 2 CH$_{Ar}$), 7.97 (d, J=8.6 Hz, 2H, 2 CH$_{Ar}$), 4.73-4.55 (m, 1H, CH), 1.59 (d, J=7.3 Hz, 3H, CH$_3$), 1.52 (s, 9H, 3 CH$_3$); HRMS (ESI) calc. for C$_{19}$H$_{22}$ClN$_6$O$_3$: [M+H]$^+$ 417.14364, found 417.1438.

Compound 28. This compound was synthesized through general synthesis protocol XV from 4-aminobenzamide and N-(2-amino-4,6-dichloropyrimidin-5-yl)formamide to afford pure compound 28 (79%). $^1$H NMR (400 MHz, d$_6$-DMSO) δ 10.29 (bs, 1H, NH), 8.60 (s, 1H, CH$_{Ar}$), 8.21-7.96 (m, 7H, 6 CH$_{Ar}$+NH), 7.95-7.78 (m, 3H, 2 CH$_{Ar}$+NH), 7.51 (bs, 1H, NH), 7.25 (bs, 1H, NH), 4.08 (bs, 2H, NH$_2$); HRMS (ESI) calc. for C$_{19}$H$_{17}$N$_8$O$_2$: [M+H]$^+$ 389.14690, found 389.1469.

Compound 29. The compound 30 was added to a mixture of LiOH (1M) and THF (1/1, v/v, 30 mL/mmol). The resulting solution was stirred for 4 h at 60° C. After evaporation under reduced pressure, the crude residue was dissolved in water and washed by ethyl acetate. Aqueous hydrochloric acid (1M) was added to the aqueous layer until pH 2-3. The resulting precipitate was filtrated and washed with water to afford pure compound 29 (89%). $^1$H NMR (400 MHz, d$_6$-DMSO) δ 13.13 (bs, 1H, COOH), 10.82 (bs, 1H, NH), 8.17 (s, 1H, CH$_{Ar}$), 8.07 (d, J=8.2 Hz, 2H, CH$_{Ar}$), 7.94 (d, J=8.2 Hz, 2H, CH$_{Ar}$), 6.63 (bs, 2H, NH$_2$); HRMS (ESI) calc. for C$_{12}$H$_{10}$N$_5$O$_3$: [M+H]$^+$ 272.07782, found 272.0778.

Compound 30. This compound was synthesized through general synthesis protocol I from 2-N-acetyl-6-O-diphenylcarbamoylguanine and 4-(methoxycarbonyl)-phenylboronic acid, and was purified by chromatography on silica gel (elution with dichloromethane/methanol) to afford pure compound 30 (13%). $^1$H NMR (400 MHz, CDCl$_3$) δ 8.30-8.22 (m, 3H, 3 CH$_{Ar}$), 8.04 (bs, 1H, NH), 7.83 (d, J=8.7 Hz, 2H, 2 CH$_{Ar}$), 7.51-7.27 (m, 11H, 10 CH$_{Ar}$+NH), 3.97 (s, 3H, CH$_3$), 2.53 (s, 3H, CH$_3$).

Compound 31. The compound 30 was added to a solution of NH$_3$ (2M) in methanol. The resulting solution was stirred for 4 h at 70° C. After evaporation under reduced pressure, the crude product was washed with dichloromethane to afford pure compound 31 (89%). $^1$H NMR (400 MHz, d$_6$-DMSO) δ 10.60 (bs, 1H, OH), 8.20 (s, 1H, CH$_{Ar}$), 8.12 (d, J=8.6 Hz, 2H, 2 CH$_{Ar}$), 8.00 (d, J=8.6 Hz, 2H, 2 CH$_{Ar}$), 6.61 (bs, 2H, NH$_2$), 3.91 (s, 3H, CH$_3$); HRMS (ESI) calc. for C$_{13}$H$_{12}$N$_5$O$_3$: [M+H]$^+$ 286.09347, found 286.0934.

Compound 32. To a solution of compound 30 in dichloromethane (20 mL/mmol) was added triethylsilane (5 equivalents). The solution was stirred at 0° C. and TFa (5 mL/mmol) was added during 15 min. The solution was then stirred at room temperature for 4 h. After evaporation under reduced pressure, the crude product was suspended in dichloromethane, filtrated and washed with dichloromethane to afford pure compound 32 (80%). $^1$H NMR (400 MHz, d$_6$-DMSO) δ 12.16 (bs, 1H, OH or NH), 11.69 (bs, 1H, OH or NH), 8.45 (s, 1H, CH$_{Ar}$), 8.14 (d, J=8.7 Hz, 2H, 2 CH$_{Ar}$), 7.96 (d, J=8.7 Hz, 2H, CH$_{Ar}$), 3.90 (s, 3H, CH$_3$), 2.18 (s, 3H, CH$_3$).

Compound 33. This compound was synthesized through general synthesis protocol XI from compound 49 (65%). $^1$H NMR (400 MHz, d$_6$-DMSO) δ 9.22 (s, 1H, CH$_{Ar}$), 8.28 (d, J=8.7 Hz, 2H, 2 CH$_{Ar}$), 8.20 (bs, 1H, NH), 8.19 (d, J=8.7 Hz, 2H, 2 CH$_{Ar}$), 7.60 (bs, 1H, NH); HRMS (ESI) calc. for C$_{11}$H$_8$ClN$_6$O: [M+H]$^+$ 275.04426, found 275.0440.

Compound 34. This compound was synthesized through general synthesis protocol VII from compound 33 and glycine tert-butyl ester to afford pure compound 34 (64%). $^1$H NMR (400 MHz, d$_6$-DMSO) δ 8.68 (t, J=6.0 Hz, 1H, NH), 8.28 (d, J=8.6 Hz, 2H, 2 CH$_{Ar}$), 8.12-8.05 (m, 3H, 2 CH$_{Ar}$+NH), 7.48 (bs, 1H, NH), 6.80 (bs, 2H, NH$_2$), 4.09 (d, J=6.0 Hz, 2H, CH$_2$), 1.43 (s, 9H, 3 CH$_3$); HRMS (ESI) calc. for C$_{17}$H$_{21}$N$_8$O$_3$: [M+H]$^+$ 385.17311, found 385.1730.

Compound 35. This compound was synthesized through general synthesis protocol X from 4-phenylbutylamine and 5-amino-4,6-dichloropyrimidine and was purified by chromatography on silica gel (elution with dichloromethane/methanol) to afford pure compound 35 (78%). $^1$H NMR (400 MHz, d$_6$-DMSO) δ 7.72 (s, 1H, CH$_{Ar}$), 7.31-7.23 (m, 2H, 2 CH$_{Ar}$), 7.22-7.13 (m, 3H, 3 CH$_{Ar}$), 6.77 (t, J=5.2 Hz, 1H, NH), 4.99 (bs, 2H, NH$_2$), 3.43-3.37 (m, 2H, CH$_2$), 2.61 (t, J=7.3 Hz, 2H, CH$_2$), 1.66-1.52 (m, 4H, 2 CH$_2$); HRMS (ESI) calc. for C$_{14}$H$_{18}$ClN$_4$: [M+H]$^+$ 277.12145, found 277.1414.

Compound 36. This compound was synthesized through general synthesis protocol X from 1,3-diaminopropane and 5-amino-4,6-dichloropyrimidine and was purified by chromatography on silica gel (elution with dichloromethane/methanol) to afford pure compound 36 (81%). $^1$H NMR (400 MHz, d$_6$-DMSO) δ 7.72 (s, 1H, CH$_{Ar}$), 7.03 (bs, 1H, NH), 5.08 (bs, 2H, NH$_2$), 3.70 (bs, 3H, NH$_3$), 3.47-3.37 (m, 2H, CH$_2$), 2.72 (t, J=7.1 Hz, 2H, CH$_2$), 1.81-1.67 (m, 2H, CH$_2$); HRMS (ESI) calc. for C$_7$H$_{13}$ClN$_5$: [M+H]$^+$ 202.08540, found 202.0855.

Compound 37. This compound was synthesized through general synthesis protocol X from 3-phenylpropylamine and 5-amino-4,6-dichloropyrimidine to afford pure compound 37 (64%). $^1$H NMR (400 MHz, d$_6$-DMSO) δ 7.72 (s, 1H, CH$_{Ar}$), 7.32-7.25 (m, 2H, 2 CH$_{Ar}$), 7.25-7.14 (m, 3H, 3 CH$_{Ar}$), 6.80 (t, J=5.0 Hz, 1H, NH), 5.02 (bs, 2H, NH$_2$), 3.39 (dd, J=12.4, 7.0 Hz, 2H, CH$_2$), 2.69-2.63 (m, 2H, CH$_2$), 1.92-1.83 (m, 2H, CH$_2$); HRMS (ESI) calc. for C$_{13}$H$_{16}$ClN$_4$: [M+H]$^+$ 263.10580, found 263.1058.

Compound 38. This compound was synthesized through general synthesis protocol X from 1,3-diaminopropane and 5-amino-4,6-dichloropyrimidine and was purified by chromatography on silica gel (elution with dichloromethane/methanol) to afford pure compound 38 (11%). $^1$H NMR (400 MHz, d$_6$-DMSO) δ 7.73 (s, 2H, 2 CH$_{Ar}$), 6.91-6.69 (m, 2H, 2 NH), 5.01 (bs, 4H, 2 NH$_2$), 3.46 (dd, J=12.3, 7.0 Hz, 4H, 2 CH$_2$), 1.88 (p, J=7.0 Hz, 2H, CH$_2$); HRMS (ESI) calc. for C$_{11}$H$_{15}$Cl$_2$N$_8$: [M+H]$^+$ 329.07912, found 329.0790.

Compound 39. This compound was synthesized through general synthesis protocol X from 2-phenylethylamine and 5-amino-4,6-dichloropyrimidine to afford pure compound 39 (76%). $^1$H NMR (400 MHz, d$_6$-DMSO) δ 7.75 (s, 1H, CH$_{Ar}$), 7.34-7.27 (m, 2H, CH$_{Ar}$), 7.27-7.16 (m, 3H, CH$_{Ar}$), 6.92 (t, J=5.2 Hz, 1H, NH), 5.00 (bs, 2H, NH$_2$), 3.66-3.55 (m, 2H, CH$_2$), 2.87 (t, J=7.4 Hz, 2H, CH$_2$); HRMS (ESI) calc. for C$_{12}$H$_{14}$ClN$_4$: [M+H]$^+$ 249.09015, found 249.0901.

Compound 40. This compound was synthesized through general synthesis protocol X from 2-(4-fluorophenyl)-ethylamine and 5-amino-4,6-dichloropyrimidine to afford pure compound 40 (89%). $^1$H NMR (400 MHz, d$_6$-DMSO) δ 7.75 (s, 1H, CH$_{Ar}$), 7.34-7.23 (m, 2H, 2 CH$_{Ar}$), 7.17-7.05 (m, 2H, CH$_{Ar}$), 6.89 (t, J=5.0 Hz, 1H, NH), 4.99 (s, 2H, NH$_2$), 3.65-3.54 (m, 2H, CH$_2$), 2.86 (t, J=7.2 Hz, 2H, CH$_2$); HRMS (ESI) calc. for C$_{12}$H$_{13}$ClFN$_4$: [M+H]$^+$ 267.08073, found 267.0807.

Compound 41. This compound was synthesized through general synthesis protocol X from 4-(aminoethyl)-pyridine and 5-amino-4,6-dichloropyrimidine to afford pure compound 41 (67%). $^1$H NMR (400 MHz, $d_6$-DMSO) δ 8.50-8.41 (m, 2H, 2 $CH_{Ar}$), 7.75 (s, 1H, $CH_{Ar}$), 7.32-7.21 (m, 2H, 2 $CH_{Ar}$), 6.91 (t, J=5.1 Hz, 1H, NH), 4.99 (bs, 2H, $NH_2$), 3.70-3.62 (m, 2H, $CH_2$), 2.90 (t, J=7.1 Hz, 2H, $CH_2$); HRMS (ESI) calc. for $C_{11}H_{13}ClN_5$: [M+H]$^+$ 250.08540, found 250.0855.

Compound 42. This compound was synthesized through general synthesis protocol X from 1,2-diaminoethane (1.5 equivalents) and 5-amino-4,6-dichloropyrimidine to afford pure compound 42 (32%). $^1$H NMR (400 MHz, $d_6$-DMSO) δ 7.75 (s, 2H, 2 $CH_{Ar}$), 7.05 (bs, 2H, 2 NH), 5.00 (bs, 4H, 2 $NH_2$), 3.67-3.50 (m, 4H, 2 $CH_2$).

Compound 43. This compound was synthesized through general synthesis protocol X from benzylamine and 5-amino-4,6-dichloropyrimidine and recrystallised in a mixture water/methanol (13/3, v/v) to afford pure compound 43 (81%). $^1$H NMR (400 MHz, $d_6$-DMSO) δ 7.72 (s, 1H, $CH_{Ar}$), 7.37-7.29 (m, 5H, $CH_{Ar}$), 7.28-7.21 (m, 1H, NH), 5.08 (bs, 2H, $NH_2$), 4.63 (d, J=5.7 Hz, 2H, $CH_2$); HRMS (ESI) calc. for $C_{11}H_{12}ClN_4$: [M+H]$^+$ 235.07450, found 235.0746.

Compound 44. This compound was synthesized through general synthesis protocol X from 4-(aminomethyl)-benzoic acid and 5-amino-4,6-dichloropyrimidine to afford pure compound 44 (89%). $^1$H NMR (400 MHz, $d_6$-DMSO) δ 7.82 (d, J=8.2 Hz, 2H, 2 $CH_{Ar}$), 7.76 (t, J=5.6 Hz, 1H, NH), 7.70 (s, 1H, $CH_{Ar}$), 7.22 (d, J=8.2 Hz, 2H, 2 $CH_{Ar}$), 5.25 (bs, 2H, $NH_2$), 4.61 (d, J=5.6 Hz, 2H, $CH_2$); HRMS (ESI) calc. for $C_{12}H_{12}ClN_4O_2$: [M+H]$^+$ 279.06433, found 279.0644.

Compound 45. This compound was synthesized through general synthesis protocol X from 3-(aminomethyl)-pyridine and 5-amino-4,6-dichloropyrimidine to afford pure compound 45 (68%). $^1$H NMR (400 MHz, $d_6$-DMSO) δ 8.56 (d, J=1.7 Hz, 1H, $CH_{Ar}$), 8.46 (dd, J=4.8, 1.7 Hz, 1H, $CH_{Ar}$), 7.74 (s, 1H, $CH_{Ar}$), 7.71 (dt, J=7.8, 2.0 Hz, 1H, $CH_{Ar}$), 7.41-7.33 (m, 2H, $CH_{Ar}$+NH), 5.08 (bs, 2H, $NH_2$), 4.64 (d, J=5.6 Hz, 2H, $CH_2$); HRMS (ESI) calc. for $C_{10}H_{11}ClN_5$: [M+H]$^+$ 236.06975, found 236.0697.

Compound 46. This compound was synthesized through general synthesis protocol X from 4-(aminomethyl)-pyridine and 5-amino-4,6-dichloropyrimidine to afford pure compound 46 (76%). $^1$H NMR (400 MHz, $d_6$-DMSO) δ 8.48 (d, J=3.6 Hz, 2H, 2 $CH_{Ar}$), 7.70 (s, 1H, $CH_{Ar}$), 7.48 (bs, 1H, NH), 7.28 (d, J=3.6 Hz, 2H, 2 $CH_{Ar}$), 5.12 (s, 2H, $NH_2$), 4.65 (d, J=4.8 Hz, 2H, $CH_2$); HRMS (ESI) calc. for $C_{10}H_{11}ClN_5$: [M+H]$^+$ 236.06975, found 236.0697.

Compound 47 was purchased from Tokyo Chemical Industry Co., Ltd.

Compound 48 was purchased from Tokyo Chemical Industry Co., Ltd.

Compound 49. This compound was synthesized through general synthesis protocol X from 4-aminobenzamide and 5-amino-4,6-dichloropyrimidine to afford pure compound 49 (27%). $^1$H NMR (400 MHz, $d_6$-DMSO) δ 8.79 (s, 1H, NH), 7.93 (s, 1H, $CH_{Ar}$), 7.85 (d, J=8.7 Hz, 2H, 2 $CH_{Ar}$), 7.84 (bs, 1H, NH), 7.78 (d, J=8.7 Hz, 2H, 2 $CH_{Ar}$), 7.21 (bs, 1H, NH), 5.52 (bs, 2H, $NH_2$); HRMS (ESI) calc. for $C_{11}H_{11}ClN_5O$: [M+H]$^+$ 264.06466, found 264.0644.

Compound 50. This compound was synthesized through general synthesis protocol XV from 4-aminobenzamide and 5-amino-4,6-dichloro-2-methylpyrimidine to afford pure compound 50 (71%). $^1$H NMR (400 MHz, $d_6$-DMSO) δ 9.44 (bs, 2H, 2 NH), 7.92-7.83 (m, 8H, 8 $CH_{Ar}$), 7.59 (bs, 4H, 4 NH), 7.24 (bs, 2H, 2 NH), 2.43 (s, 3H, $CH_3$); HRMS (ESI) calc. for $C_{19}H_{20}N_7O_2$: [M+H]$^+$ 378.16730, found 378.1672.

Compound 51. This compound was synthesized through general synthesis protocol X from 3-aminobenzamide and 5-amino-4,6-dichloropyrimidine, was purified by chromatography on silica gel (elution with dichloromethane/methanol) and then recrystallised from isopropanol to afford pure compound 51 (51%). $^1$H NMR (400 MHz, $d_6$-DMSO) δ 8.76 (bs, 1H, NH), 8.10 (s, 1H, $CH_{Ar}$), 8.03-7.84 (m, 3H, 2 $CH_{Ar}$+NH), 7.53 (d, J=7.7 Hz, 1H, $CH_{Ar}$), 7.45-7.27 (m, 2H, $CH_{Ar}$+NH), 5.46 (bs, 2H, $NH_2$); HRMS (ESI) calc. for $C_{11}H_{11}ClN_5O$: [M+H]$^+$ 264.06466, found 264.0648.

Compound 52. This compound was synthesized through general synthesis protocol X from 4-aminosulfanilic acid and 5-amino-4,6-dichloropyrimidine to afford pure compound 52 (45%). $^1$H NMR (400 MHz, $d_6$-DMSO) δ 8.77 (bs, 1H, NH), 7.91 (s, 1H, $CH_{Ar}$), 7.67-7.63 (m, 2H, $CH_{Ar}$), 7.60-7.53 (m, 2H, $CH_{Ar}$), 5.10 (bs, 2H, $NH_2$); HRMS (ESI) calc. for $C_{10}H_8ClN_4O_3S$: [M−H]$^-$ 299.00111, found 299.0011.

Compound 53. This compound was synthesized through general synthesis protocol III from 99, and was purified by chromatography on silica gel (eluent dichloromethane/methanol) to afford pure compound 53 (94%). $^1$H NMR (400 MHz, $d_6$-DMSO) δ 8.16 (s, 1H, $CH_{Ar}$), 7.74 (bs, 2H, $NH_2$), 7.33-7.11 (m, 5H, 5 $CH_{Ar}$), 4.25 (t, J=6.5 Hz, 2H, $CH_2$), 2.78-2.69 (m, 2H, $CH_2$), 2.07-1.94 (m, 2H, $CH_2$); HRMS (ESI) calc. for $C_{14}H_{16}N_5O$: [M+H]$^+$ 270.13494, found 270.1349.

Compound 54. Compound Int-2 was dissolved in a saturated solution of $NH_3$ in ethanol. The resulting solution was stirred in a sealed tube at 60° C. for 24 h. After evaporation under reduced pressure, the crude residue was washed several times with water to afford pure compound 54 (70%). $^1$H NMR (400 MHz, $d_6$-DMSO) δ 8.54 (s, 1H, $CH_{Ar}$), 7.90 (bs, 2H, $NH_2$), 7.73 (d, J=8.4 Hz, 2H, 2 $CH_{Ar}$), 7.52 (d, J=8.4 Hz, 2H, 2 $CH_{Ar}$), 5.33 (bs, 1H, OH), 4.58 (bs, 2H, $CH_2$); HRMS (ESI) calc. for $C_{12}H_{11}ClN_5O$: [M+H]$^+$ 276.06466, found 276.0645.

Compound 55. To a solution of 5-amino-4,6-dichloropyrimidine (1 equivalent) in DMF (3 mL/mmol), 4-hydroxybenzamide (1.2 equivalents) and $K_2CO_3$ (3 equivalents) were added. The resulting solution was stirred overnight under argon at 60° C. After evaporation under reduced pressure, the crude residue was purified by extraction with ethyl acetate/water and then with ethyl acetate/brine to afford pure compound 55 (59%). $^1$H NMR (400 MHz, $d_6$-DMSO) δ 7.99 (bs, 1H, $NH_2$), 7.97-7.90 (m, 2H, 2 $CH_{Ar}$), 7.82 (s, 1H, $CH_{Ar}$), 7.37 (bs, 1H, $NH_2$), 7.34-7.27 (m, 2H, 2 $CH_{Ar}$), 5.83 (bs, 2H, $NH_2$); HRMS (ESI) calc. for $C_{11}H_{10}ClN_4O_2$: [M+H]$^+$ 265.04868, found 265.0485.

Compound 56. This compound was synthesized through general synthesis protocol XVII from 5-amino-4,6-dichloropyrimidine and 4-aminobenzenesulfonamide to afford pure compound 56 (99%). $^1$H NMR (400 MHz, $d_6$-DMSO) δ 8.90 (bs, 1H, NH), 7.94 (s, 1H, $CH_{Ar}$), 7.92-7.85 (m, 2H, 2 $CH_{Ar}$), 7.80-7.74 (m, 2H, 2 $CH_{Ar}$), 7.23 (bs, 2H, $NH_2$), 5.55 (bs, 2H, $NH_2$); HRMS (ESI) calc. for $C_{10}H_{11}ClN_5O_2S$: [M+H]$^+$ 300.03165, found 300.0315.

Compound 57. This compound was synthesized through general synthesis protocol VI from compound Int-8 and was purified by chromatography on silica gel (eluent dichloromethane/methanol) to afford pure compound 57 (45%). $^1$H NMR (400 MHz, $d_6$-DMSO) δ 8.00 (s, 1H, $CH_{Ar}$), 7.73 (d, J=8.2 Hz, 2H, 2 $CH_{Ar}$), 7.52 (d, J=8.2 Hz, 2H, 2 $CH_{Ar}$), 7.27-7.10 (m, 5H, 5 $CH_{Ar}$), 4.71-4.59 (m, 3H, $CH_2$+CH), 3.38 (dd, J=14.6, 7.4 Hz, 2H, $CH_2$), 2.68 (t, J=7.6 Hz, 2H, CH$_2$), 1.95-1.86 (m, 2H, CH$_2$), 1.53 (d, J=7.0 Hz, 3H, CH$_3$); HRMS (ESI) calc. for C$_{24}$H$_{27}$N$_6$O$_3$: [M+H]$^+$ 447.21392, found 447.2136.

Compound 58. This compound was synthesized through general synthesis protocol II from compound 9 and 4-phenylbutylamine (10 equivalents), and was purified by chromatography on silica gel (eluent dichloromethane/methanol) to afford pure compound 58 (61%). $^1$H NMR (400 MHz, d$_6$-DMSO) δ 12.11 (bs, 1H, NH), 7.68-7.45 (m, 2H, NH+CH$_{Ar}$), 7.35-7.21 (m, 4H, 4 CH$_{Ar}$), 7.21-7.07 (m, 3H, 3 CH$_{Ar}$), 6.83 (d, J=8.7 Hz, 2H, 2 CH$_{Ar}$), 6.19 (bs, 1H, NH), 4.55 (bs, 2H, CH$_2$), 3.69 (s, 3H, CH$_3$), 3.23 (dd, J=12.7, 6.5 Hz, 2H, CH$_2$), 2.56 (t, J=7.3 Hz, 2H, CH$_2$), 1.65-1.45 (m, 4H, 2 CH$_2$); HRMS (ESI) calc. for C$_{23}$H$_{27}$N$_6$O: [M+H]$^+$ 403.22409, found 403.2242.

Compound 59. To a suspension of Int-11 (1 equivalent) in a mixture of water/THF (2/3 v/v, 7 mL/mmol) were added palladium acetate (0.1 equivalent) and potassium fluoride (40% on alumina, 2 equivalents). The reaction mixture was kept at room temperature for 40 min, concentrated and purified by reverse phase chromatography (eluent water/methanol) to afford pure compound 59 (76%). $^1$H NMR (400 MHz, d$_6$-DMSO) δ 8.10 (s, 1H, NH), 7.79-7.69 (m, 4H, 3 CH$_{Ar}$+NH$_2$), 7.64 (d, J=8.8 Hz, 2H, 2 CH$_{Ar}$), 7.08 (bs, 1H, NH$_2$), 6.01 (bs, 2H, NH$_2$), 4.29 (bs, 2H, NH$_2$); HRMS (ESI) calc. for C$_{11}$H$_{12}$N$_5$O: [M+H]$^+$ 230.10363, found 230.1034.

Compound 60. To a solution of compound 10 (1 equivalent) in DMF (1 mL/mmol), CuI (1.1 equivalents), trans-1,2-diaminocyclohexane (2.2 equivalents), K$_3$PO$_4$ (4 equivalents) and 4-iodobenzamide (1.3 equivalents) were added. The solution was stirred overnight at 90° C. under argon. After concentration under reduced pressure, the reaction mixture was diluted with dichloromethane and extracted with a saturated aqueous solution of ethylenediaminetetraacetic acid (EDTA). The organic layer was washed with water and brine, then dried over magnesium sulfate. After filtration and concentration under reduced pressure the crude product was purified by chromatography on silica gel (eluent dichloromethane/methanol) then by crystallization from ethanol to afford pure compound 60 (11%). $^1$H NMR (400 MHz, d$_6$-DMSO) δ 10.50 (bs, 1H, NH), 8.33 (bs, 1H, NH), 8.21-8.08 (m, 3H, 3 CH$_{Ar}$), 7.94-7.83 (m, 3H, NH$_2$+2 CH$_{Ar}$), 7.35-7.12 (m, 7H, 7 CH$_{Ar}$), 6.84 (d, J=8.4 Hz, 2H, 2 CH$_{Ar}$), 6.66 (bs, 1H, NH$_2$), 4.58 (bs, 2H, CH$_2$), 3.70 (s, 3H, CH$_3$), 3.30-3.26 (m, 2H, CH$_2$), 2.66-2.59 (m, 2H, CH$_2$), 1.92-1.78 (m, 2H, CH$_2$); HRMS (ESI) calc. for C$_{29}$H$_{30}$N$_7$O$_2$: [M+H]$^+$ 508.2456, found 508.2486.

Compound 61. To a solution of 2,6-diaminopurine (1 equivalent) in DMF (1 mL/mmol), CuI (1.1 equivalents), N,N'-dimethylethylenediamine (2.2 equivalents), K$_3$PO$_4$ (4 equivalents) and 4-iodobenzylalcool (1.3 equivalents) were added. The solution was stirred overnight at 90° C. under argon. After concentration under reduced pressure, the reactionnal mixture was diluted with dichloromethane and extracted with a saturated aqueous solution of ethylenediaminetetraacetic acid (EDTA). The organic layer was washed with water and brine, then dried over magnesium sulfate. After filtration and concentration under reduced pressure the crude product was purified by chromatography on silica gel (eluent dichloromethane/methanol) to afford pure compound 61 (5%). $^1$H NMR (400 MHz, d$_6$-DMSO) δ 8.11 (s, 1H, CH$_{Ar}$), 7.78 (d, J=8.5 Hz, 2H, 2 CH$_{Ar}$), 7.45 (d, J=8.5 Hz, 2H, 2 CH$_{Ar}$), 6.78 (bs, 2H, NH$_2$), 5.87 (bs, 2H, NH$_2$), 5.26 (t, J=5.7 Hz, 1H, OH), 4.55 (d, J=5.7 Hz, 2H, CH$_2$); HRMS (ESI) calc. for C$_{12}$H$_{13}$ClN$_6$O: [M+H]$^+$ 257.11454, found 257.1144.

Compound 62. To a suspension of Int-10 (1 equivalent) in methanol (3 mL/mmol), was added sodium methoxide (10 equivalents). The suspension was stirred under reflux for 10 h, under argon. After concentration under reduced pressure, the crude product was purified by chromatography on silica gel (eluent dichloromethane/methanol) to afford pure compound 62 (59%). $^1$H NMR (400 MHz, d$_6$-DMSO) δ 8.39 (s, 1H, CH$_{Ar}$), 8.08 (bs, 1H, NH$_2$), 8.07-7.96 (m, 4H, 4 CH$_{Ar}$), 7.48 (bs, 1H, NH$_2$), 6.63 (bs, 2H, NH$_2$), 4.00 (s, 3H, CH$_3$); HRMS (ESI) calc. for C$_{13}$H$_{13}$N$_6$O: [M+H]$^+$ 285.10945, found 285.1099.

Compound 63. To a suspension of Int-10 (1 equivalent) in methanol (4 ml/mmol) were added Pd/C 10% (0.2 equivalent) and ammonium formate (11 equivalents). The reaction mixture was bubbled with argon and then refluxed for 17 h. After concentration under reduced pressure, the crude product was purified by chromatography on silica gel (eluent dichloromethane/methanol) to afford pure compound 63 (77%). $^1$H NMR (400 MHz, d$_6$-DMSO) δ 8.71 (s, 1H, CH$_{Ar}$), 8.59 (s, 1H, CH$_{Ar}$), 8.09 (bs, 1H, NH$_2$), 8.07-7.96 (m, 4H, 4 CH$_{Ar}$), 7.49 (bs, 1H, NH$_2$), 6.72 (bs, 2H, NH$_2$); HRMS (ESI) calc. for C$_{12}$H$_{11}$N$_6$O: [M+H]$^+$ 255.09889, found 255.0989.

Compound 64. This compound was synthesized through general synthesis protocol XI from compound 56. After precipitation, it was further purified by chromatography on silica gel (eluent dichloromethane/methanol) to afford pure compound 64 (58%). $^1$H NMR (400 MHz, d$_6$-DMSO) δ 9.24 (s, 1H, CH$_{Ar}$), 8.41 (d, J=8.8 Hz, 2H, 2 CH$_{Ar}$), 8.16 (d, J=8.8 Hz, 2H, 2 CH$_{Ar}$), 7.60 (bs, 2H, NH$_2$); HRMS (ESI) calc. for C$_{10}$H$_8$ClN$_6$O$_2$S: [M+H]$^+$ 311.01125, found 311.0112.

Compound 65. To a solution of 5-amino-4,6-dichloro-2-methylpyrimidine (1 equivalent) in a mixture water/dioxane (1/1 v/v, 4 mL/mmol) was added 4-aminobenzamide (1 equivalent). The solution was refluxed overnight. After cooling down to room temperature, the suspension was filtered and the precipitate was washed with 1,4-dioxane. The crude product was then triturated in an aqueous solution of NaHCO$_3$ 5% and filtered to afford pure compound 65 (44%). $^1$H NMR (400 MHz, d$_6$-DMSO) δ 8.72 (bs, 1H, NH), 7.90-7.76 (m, 5H, 4 CH$_{Ar}$+NH$_2$), 7.21 (bs, 1H, NH$_2$), 5.27 (bs, 2H, NH$_2$), 2.34 (s, 3H, CH$_3$); HRMS (ESI) calc. for C$_{12}$H$_{13}$ClN$_5$O: [M+H]$^+$ 278.08031, found 278.0808.

Compound 66. To a solution of 3-phenylpropanol (1 equivalent) in THF (5 mL/mmol), NaH (1.5 equivalent) was added. The resulting solution was stirred under argon for 40 min at room temperature. After cooling to 0° C., 5-amino-4,6-dichloropyrimidine was added and the solution was stirred under argon for 1 h 30 at 0° C. and then at room temperature overnight. After evaporation under reduced pressure, the crude residue was purified by extraction dichloromethane/water and then by chromatography on silica gel (eluent dichloromethane/methanol) to afford pure compound 66 (95%). $^1$H NMR (400 MHz, d$_6$-DMSO) δ 7.87 (s, 1H, CH$_{Ar}$), 7.32-7.21 (m, 4H, 4 CH$_{Ar}$), 7.18 (ddd, J=6.2, 3.4, 1.6 Hz, 1H, CH$_{Ar}$), 5.38 (bs, 2H, NH$_2$), 4.33 (t, J=6.4 Hz, 2H, CH$_2$), 2.82-2.71 (m, 2H, CH$_2$), 2.05 (dq, J=9.1, 6.4 Hz, 2H, CH$_2$); HRMS (ESI) calc. for C$_{13}$H$_{15}$ClN$_3$O: [M+H]$^+$ 264.08982, found 264.0901.

Compound 67 was purchased from Tokyo Chemical Industry Co., Ltd.

Compound 68 was purchased from Sigma-Aldrich Co., Ltd.

Compound 69. 2,5-diamino-4,6-dichloropyrimidine (1 equivalent) was suspended in NH$_4$OH (18 mL/mmol), heated in a sealed tube to 135° C. for 24 h, concentrated in vacuo then purified by chromatography on silica gel (eluent dichloromethane/methanol/NH$_4$OH) to afford pure compound 69 (93%). $^{13}$C NMR (101 MHz, d$_6$-DMSO) δ 156.0, 155.5, 113.3, 39.5; HRMS (ESI) calc. for C$_4$H$_7$ClN$_5$: [M+H]$^+$ 160.03845, found 160.0385.

Compound 70. To a solution of freshly prepared 3-phenylpropanic anhydride (1 equivalent) in pyridine (4.5 mL/mmol) was added 2-amino-6-chloropurine (1 equivalent). The resulting solution was stirred at room temperature for 5 h, concentrated in vacuo then purified by chromatography on silica gel (eluent dichloromethane/methanol). Fractions containing the final product were collected and concentrated in vacuo. The residual solid was dissolved in dichloromethane (1 ml) and precipitated with cyclohexane (6 mL). The precipitate was filtrated, washed with cyclohexane and dried in vacuo to afford pure compound 70 (13%). $^1$H NMR (400 MHz, d$_6$-DMSO) δ 8.57 (s, 1H, NH), 7.34-7.15 (m, 7H, 6 CH$_{Ar}$+NH), 3.63 (t, J=7.6 Hz, 2H, CH$_2$), 3.02 (t, J=7.6 Hz, 2H, CH$_2$); HRMS (ESI) calc. for C$_{14}$H$_{13}$ClN$_5$O: [M+H]$^+$ 302.08031, found 302.0804.

Compound 71. To a suspension of 157 (1 equivalent) in methanol (10 ml/mmol) was added Pd/C 10% (0.1 equivalent). The reaction mixture was bubbled with argon and then with dihydrogen. The suspension was kept overnight under dihydrogen (1 atm), and was purified by chromatography on silica gel (eluent dichloromethane/methanol) to afford pure compound 71 (45%). $^1$H NMR (400 MHz, d$_6$-DMSO) δ 12.12 (bs, 1H, OH), 8.07 (bs, 1H, NH), 7.84-7.67 (m, 3H, 2 CH$_{Ar}$+NH$_2$), 7.61 (s, 1H, CH$_{Ar}$), 7.42 (d, J=8.8 Hz, 2H, 2 CH$_{Ar}$), 7.09 (bs, 1H, NH$_2$), 4.43 (bs, 2H, NH$_2$). HRMS (ESI) calc. for C$_{11}$H$_{12}$N$_5$O$_2$: [M+H]$^+$ 246.09855, found 246.0985.

Compound 72. This compound was synthesized through general synthesis protocol III from compound 58 and was purified by washing with water to afford pure compound 72 (97%). $^1$H NMR (400 MHz, d$_6$-DMSO) δ 12.11 (bs, 1H, NH), 7.63 (bs, 1H, CH$_{Ar}$), 7.26 (t, J=7.3 Hz, 2H, 2 CH$_{Ar}$), 7.23-7.10 (m, 3H, 3 CH$_{Ar}$), 6.51 (bs, 2H, NH$_2$), 6.14-6.05 (m, 1H, NH), 3.23 (dd, J=12.8, 6.5 Hz, 2H, CH$_2$), 2.59 (t, J=7.4 Hz, 2H, CH$_2$), 1.64-1.47 (m, 4H, 2 CH$_2$); HRMS (ESI) calc. for C$_{15}$H$_{19}$N$_6$: [M+H]$^+$ 283.16657, found 283.1666.

Compound 74 was purchased from Tokyo Chemical Industry Co., Ltd.

Compound 75. To a suspension of 155 (1 equivalent) in methanol (8 ml/mmol) was added Pd/C 10% (0.04 equivalent). The reaction mixture was bubbled with argon and then with dihydrogen. The suspension was kept overnight under dihydrogen (1 atm), and concentrated under reduced pressure. The crude product was purified by chromatography on silica gel (eluent dichloromethane/methanol) to afford pure compound 75 (74%). $^1$H NMR (400 MHz, d$_6$-DMSO) δ 8.38 (bs, 1H, NH), 7.91 (s, 1H, CH$_{Ar}$), 7.83-7.74 (m, 3H, 2 CH$_{Ar}$+NH$_2$), 7.71 (d, J=8.8 Hz, 2H, CH$_{Ar}$), 7.13 (bs, 1H, NH$_2$), 4.71 (bs, 2H, NH$_2$), 3.92 (s, 3H, CH$_3$); HRMS (ESI) calc. for C$_{12}$H$_{14}$N$_5$O$_2$: [M+H]$^+$ 260.11420, found 260.1140.

Compound 76. To a suspension of 56 in trimethyl orthoformate (3 mL/mmol) was added ethanesulfonic acid (25 μL/mmol). The suspension was heated under microwave irradiation at 120° C. for 1 h. After cooling down to room temperature, it was diluted with methanol and filtered. The precipitate was then triturated in water (6 mL/mmol) for 24 h and filtered to afford pure compound 76 (48%). $^1$H NMR (400 MHz, d$_6$-DMSO) δ 9.21 (s, 1H, CH$_{Ar}$), 8.90 (s, 1H, CH$_{Ar}$), 8.16 (d, J=8.7 Hz, 2H, 2 CH$_{Ar}$), 8.07 (d, J=8.7 Hz, 2H, 2 CH$_{Ar}$), 7.55 (bs, 2H, NH$_2$); HRMS (ESI) calc. for C$_{11}$H$_9$ClN$_5$O$_2$S: [M+H]$^+$ 310.01600, found 310.0161.

Compound 77. To a suspension of 49 in triethyl orthoacetate (3 mL/mmol) was added ethanesulfonic acid (25 μL/mmol). The suspension was heated at 130° C. for 48 h. After cooling down to room temperature, the suspension was filtered. The precipitate was purified by chromatography on silica gel (eluent dichloromethane/methanol) to afford pure compound 77 (36%). $^1$H NMR (400 MHz, d$_6$-DMSO) δ 8.68 (s, 1H, CH$_{Ar}$), 8.17 (bs, 1H, NH$_2$), 8.10 (d, J=8.6 Hz, 2H, 2 CH$_{Ar}$), 7.71 (d, J=8.6 Hz, 2H, 2 CH$_{Ar}$), 7.59 (bs, 1H, NH$_2$), 2.55 (s, 3H, CH$_3$); HRMS (ESI) calc. for C$_{13}$H$_{11}$ClN$_5$O: [M+H]$^+$ 288.06466, found 288.0650.

Compound 78. To a solution of 158 (1 equivalent) in methanol (7 ml/mmol) was added Pd/C 10% (0.04 equivalent). The reaction mixture was bubbled with argon and then with dihydrogen. The suspension was kept overnight under dihydrogen (1 atm), and concentrated under reduced pressure. The crude product was purified by chromatography on silica gel (eluent dichloromethane/methanol) to afford pure compound 78 (61%). $^1$H NMR (400 MHz, d$_6$-DMSO) δ 9.32 (bs, 1H, NH), 8.03 (s, 1H, CH$_{Ar}$), 7.52 (s, 1H, CH$_{Ar}$), 7.42 (bs, 1H, OH), 7.14 (d, J=8.5 Hz, 2H, 2 CH$_{Ar}$), 6.71 (d, J=8.5 Hz, 2H, 2 CH$_{Ar}$), 5.13 (bs, 2H, NH$_2$), 4.52 (d, J=5.5 Hz, 2H, CH$_2$); HRMS (ESI) calc. for C$_{11}$H$_{13}$N$_4$O: [M+H]$^+$ 217.10839, found 217.1085.

Compound 79. This compound was synthesized through general synthesis protocol I from 2,6-dichloropurine and 4-carbamoylphenylboronic acid, and was purified by chromatography on silica gel (eluent dichloromethane/methanol) to afford pure compound 79 (16%). $^1$H NMR (400 MHz, d$_6$-DMSO) δ 9.19 (s, 1H, CH$_{Ar}$), 8.18-8.09 (m, 3H, 2 CH$_{Ar}$+NH), 7.97-7.93 (m, 2H, 2 CH$_{Ar}$), 7.55 (bs, 1H, NH); HRMS (ESI) calc. for C$_{12}$H$_8$Cl$_2$N$_5$O: [M+H]$^+$ 308.01001, found 308.0100.

Compound 80. This compound was synthesized through general synthesis protocol I from 2,6-dichloropurine and phenylboronic acid, and was purified by chromatography on silica gel (eluent dichloromethane/methanol) to afford pure compound 80 (14%). $^1$H NMR (400 MHz, CDCl$_3$) δ 8.38 (s, 1H, CH$_{Ar}$), 7.70-7.65 (m, 2H, 2 CH$_{Ar}$), 7.65-7.59 (m, 2H, 2 CH$_{Ar}$), 7.56-7.51 (m, 1H, CH$_{Ar}$); HRMS (ESI) calc. for C$_{11}$H$_7$Cl$_2$N$_4$: [M+H]$^+$ 265.00454, found 265.0042.

Compound 81. This compound was synthesized through general synthesis protocol VII from compound 80 and 1-alanine tert-butyl ester, and was precipitated in diethyl ether, filtrated and washed to afford pure compound 81 (97%). $^1$H NMR (400 MHz, CDCl$_3$) δ 8.00 (s, 1H, CH$_{Ar}$), 7.67-7.63 (m, 2H, 2 CH$_{Ar}$), 7.57-7.52 (m, 2H, 2 CH$_{Ar}$), 7.47-7.40 (m, 1H, CH$_{Ar}$), 6.45 (bs, 1H, NH), 4.84 (bs, 1H, CH), 1.57 (d, J=7.1 Hz, 3H, CH$_3$), 1.50 (s, 9H, 3 CH$_3$); HRMS (ESI) calc. for C$_{18}$H$_{21}$N$_5$O$_2$: [M+H]$^+$ 374.138090, found 374.1378.

Compound 82. This compound was synthesized through general synthesis protocol II from compound 81 and 3-phenylpropyl-1-amine, and was purified by chromatography on silica gel (eluent dichloromethane/ethyl acetate) to afford pure compound 82 (22%). $^1$H NMR (400 MHz, CDCl$_3$) δ 7.81 (s, 1H, CH$_{Ar}$), 7.79-7.71 (m, 2H, 2 CH$_{Ar}$), 7.55 (t, J=7.9 Hz, 2H, 2 CH$_{Ar}$), 7.42 (t, J=7.4 Hz, 1H, CH$_{Ar}$), 7.38-7.19 (m, 5H, 5 CH$_{Ar}$), 6.10 (bs, 1H, NH), 4.95 (bs, 1H, CH), 4.82 (bs, 1H, NH), 3.65-3.40 (m, 2H, CH$_2$), 2.87-2.65 (m, 2H, CH$_2$), 2.04-1.89 (m, 2H, CH$_2$), 1.58 (d, J=7.1 Hz, 3H, CH$_3$), 1.53 (s, 9H, 3 CH$_3$); HRMS (ESI) calc. for C$_{27}$H$_{33}$N$_6$O$_2$: [M+H]$^+$ 473.26597, found 473.2660.

Compound 83. This compound was synthesized through general synthesis protocol VI from compound 92, was purified by extraction dichloromethane/water and then was purified by chromatography on silica gel (eluent dichloromethane/methanol) to afford pure compound 83 (93%). $^1$H NMR (400 MHz, CD$_3$OD) δ 8.00 (s, 1H, CH$_{Ar}$), 7.79-7.71 (m, 2H, 2 CH$_{Ar}$), 7.57-7.50 (m, 2H, 2 CH$_{Ar}$), 7.47-7.39 (m, 1H, CH$_{Ar}$), 7.27-7.11 (m, 5H, 5 CH$_{Ar}$), 4.72 (bs, 1H, CH), 3.45-3.35 (m, 2H, CH$_2$), 2.74-2.62 (m, 2H, CH$_2$), 1.96-1.84 (m, 2H, CH$_2$), 1.58 (d, J=7.2 Hz, 3H, CH$_3$); HRMS (ESI) calc. for C$_{23}$H$_{25}$N$_6$O$_2$: [M+H]$^+$ 417.20347, found 417.2034.

Compound 85. This compound was synthesized through general synthesis protocol II from compound Int-1 and 2-(4-methoxyphenyl)ethyl-1-amine, and was purified by chromatography on silica gel (eluent dichloromethane/methanol) to afford pure compound 85 (31%). $^1$H NMR (400 MHz, CDCl$_3$) δ 7.75 (m, 3H, 3 CH$_{Ar}$), 7.53 (m, 2H, 2 CH$_{Ar}$), 7.41 (tt, J=7.4 Hz, J=1.1 Hz, 1H, CH$_{Ar}$), 7.33 (d, J=8.7 Hz, 2H, 2 CH$_{Ar}$), 7.15 (d, J=8.6 Hz, 2H, 2 CH$_{Ar}$), 6.88 (d, J=8.7 Hz, 2H, 2 CH$_{Ar}$), 6.85 (d, J=8.6 Hz, 2H, 2 CH$_{Ar}$), 5.86 (bs, 1H, NH), 4.97 (bs, 1H, NH), 4.77 (bs, 2H, CH$_2$), 3.81 (s, 3H, CH$_3$), 3.80 (s, 3H, CH$_3$), 3.64 (q, J=7.0 Hz, 2H, CH$_2$), 2.87 (t, J=7.0 Hz, 2H, CH$_2$); HRMS (ESI) calc. for C$_{28}$H$_{29}$N$_6$O$_2$: [M+H]$^+$ 481.23465, found 481.2348.

Compound 86. This compound was synthesized through general synthesis protocol I from 2,6-dichloropurine and 4-acetylphenylboronic acid, and was purified by chromatography on silica gel (eluent dichloromethane/methanol) to afford pure compound 86 (16%). $^1$H NMR (400 MHz, CD$_3$OD) δ 9.00 (s, 1H, CH$_{Ar}$), 8.32-8.25 (m, 2H, 2 CH$_{Ar}$), 8.09-8.04 (m, 2H, 2 CH$_{Ar}$), 2.70 (s, 3H, CH$_3$); HRMS (ESI) calc. for C$_{13}$H$_9$Cl$_2$N$_4$O: [M+H]$^+$ 307.01479, found 307.0149.

Compound 88. This compound was synthesized through general synthesis protocol II from 2,6-dichloropurine and 4-methoxybenzylamine, and was purified by chromatography on silica gel (eluent dichloromethane/methanol) to afford pure compound 88 (66%). $^1$H NMR (400 MHz, d$_6$-DMSO) δ 12.99 (bs, 1H, NH), 8.11 (bs, 1H, CH$_{Ar}$), 7.92 (bs, 2H, 2 NH); 7.23 (d, J=8.5 Hz, 4H, 4 CH$_{Ar}$), 6.85 (d, J=8.5 Hz, 2H, 2 CH$_{Ar}$), 6.84 (d, J=8.5 Hz, 2H, 2 CH$_{Ar}$), 4.64 (bs, 2H, CH$_2$), 4.50 (d, J=5.5 Hz, 2H, CH$_2$), 3.72 (s, 3H, OCH$_3$), 3.71 (s, 3H, CH$_3$); HRMS (ESI) calc. for C$_{21}$H$_{23}$N$_6$O$_2$: [M+H]$^+$ 391.18770, found 391.1877.

Compound 89. This compound was synthesized through general synthesis protocol V from compound 9 and 4-(bromomethyl)benzamide, and was purified by precipitation in methanol to afford pure compound 89 (50%). $^1$H NMR (400 MHz, d$_6$-DMSO) δ 8.81 (t, J=5.4 Hz, 1H, NH), 8.29 (s, 1H, CH$_{Ar}$), 7.93 (bs, 1H, NH$_2$), 7.83 (d, J=8.1 Hz, 2H, 2 CH$_{Ar}$), 7.35 (bs, 1H, NH$_2$), 7.32 (d, J=8.1 Hz, 2H, 2 CH$_{Ar}$), 7.28 (d, J=8.6 Hz, 2H, 2 CH$_{Ar}$), 6.87 (d, J=8.6 Hz, 2H, 2 CH$_{Ar}$), 5.40 (s, 2H, CH$_2$), 4.56 (d, J=5.4 Hz, 2H, CH$_2$), 3.71 (s, 3H, CH$_3$); HRMS (ESI) calc. for C$_{21}$H$_{20}$ClN$_6$O$_2$: [M+H]$^+$ 423.13308, found 423.1334.

Compound 90. This compound was synthesized through general synthesis protocol I from 2,6-dichloropurine and 4-(methoxycarbonyl)phenylboronic acid, and was purified by chromatography on silica gel (eluent dichloromethane/methanol) to afford pure compound 90 (7%). $^1$H NMR (400 MHz, CDCl$_3$) δ 8.44 (s, 1H, CH$_{Ar}$), 8.29 (d, J=8.9 Hz, 2H, 2 CH$_{Ar}$), 7.84 (d, J=8.9 Hz, 2H, 2 CH$_{Ar}$), 3.99 (s, 3H, CH$_3$); HRMS (ESI) calc. for C$_{13}$H$_9$Cl$_2$N$_4$O$_2$: [M+H]$^+$ 323.00971, found 323.0998.

Compound 91. This compound was obtained in two steps through general synthesis protocol I from 2-N-acetyl-6-O-diphenylcarbamoylguanine and 3,4-dimethoxyphenylboronic acid and was purified by chromatography on silica gel (eluent dichloromethane/methanol). The intermediate compound was added to a solution of NH$_3$ (2M) in methanol. The resulting solution was stirred for 4 h at 70° C. After evaporation under reduced pressure, the crude product was washed with dichloromethane to afford pure compound 91 (72%). $^1$H NMR (400 MHz, d$_6$-DMSO) δ 10.69 (bs, 1H, OH), 8.00 (s, 1H, CH$_{Ar}$), 7.38 (s, 1H, CH$_{Ar}$), 7.23 (m, 1H, CH$_{Ar}$), 7.08 (m, 1H, CH$_{Ar}$), 6.51 (bs, 2H, NH$_2$), 3.83 (s, 6H, 2 CH$_3$).

Compound 92. This compound was obtained in two steps through general synthesis protocol I from 2-N-acetyl-6-O-diphenylcarbamoylguanine and phenylboronic acid and was purified by chromatography on silica gel (eluent dichloromethane/methanol). The intermediate compound was added to a solution of NH$_3$ (2M) in methanol. The resulting solution was stirred for 4 h at 70° C. After evaporation under reduced pressure, the crude product was washed with dichloromethane to afford pure compound 92 (86%). $^1$H NMR (400 MHz, d$_6$-DMSO) δ 10.56 (bs, 1H, OH), 8.08 (s, 1H, CH$_{Ar}$), 7.77 (m, 2H, 2 CH$_{Ar}$), 7.58 (m, 2H, 2 CH$_{Ar}$), 7.46 (m, 1H, CH$_{Ar}$), 6.53 (bs, 2H, NH$_2$).

Compound 93. This compound was synthesized through general synthesis protocol V from 2,6-dichloropurine and 4-(bromomethyl)benzamide, and was purified by chromatography on silica gel (eluent dichloromethane/methanol) to afford pure compound 93 (64%). $^1$H NMR (400 MHz, d$_6$-DMSO) δ 8.85 (s, 1H, CH$_{Ar}$), 7.95 (bs, 1H, NH$_2$), 7.84 (d, J=8.4 Hz, 2H, 2 CH$_{Ar}$), 7.39 (d, J=8.4 Hz, 2H, 2 CH$_{Ar}$), 7.38 (bs, 1H, NH$_2$), 5.55 (s, 2H, CH$_2$); HRMS (ESI) calc. for C$_{13}$H$_{10}$Cl$_2$N$_5$O: [M+H]$^+$ 322.02569, found 322.0259.

Compound 94. This compound was synthesized through general synthesis protocol I from 2,6-dichloropurine and (pyridin-3-yl)boronic acid, and was purified by chromatography on silica gel (eluent dichloromethane/ethyl acetate) to afford pure compound 94 (2%). $^1$H NMR (400 MHz, CDCl$_3$) δ 8.95 (bs, 1H, CH$_{Ar}$), 8.76 (bs, 1H, CH$_{Ar}$), 8.43 (s, 1H, CH$_{Ar}$), 8.15-8.08 (m, 1H, CH$_{Ar}$), 7.58 (dd, J=8.2, 4.8 Hz, 1H, CH$_{Ar}$); HRMS (ESI) calc. for C$_{10}$H$_6$Cl$_2$N$_5$: [M+H]$^+$ 265.99948, found 265.9994.

Compound 95. This compound was synthesized through general synthesis protocol I from 2,6-dichloropurine and 3-carbamoylphenylboronic acid, and was purified by chromatography on silica gel (eluent dichloromethane/methanol/ethyl acetate) to afford pure compound 95 (3%). $^1$H NMR (400 MHz, CD$_3$OD) δ 8.94 (s, 1H, CH$_{Ar}$), 8.31 (t, J=1.9 Hz, 1H, CH$_{Ar}$), 8.10-8.03 (m, 2H, 2 CH$_{Ar}$), 7.77 (t, J=7.9 Hz, 1H, CH$_{Ar}$); HRMS (ESI) calc. for C$_{12}$H$_8$Cl$_2$N$_5$O: [M+H]$^+$ 308.01004, found 308.0099.

Compound 96. This compound was synthesized through general synthesis protocol XV from 4-aminobenzamide and 6-chlorouracil to afford pure compound 96 (64%). $^1$H NMR (400 MHz, d$_6$-DMSO) δ 10.58 (s, 1H, NH), 10.30 (s, 1H, NH), 8.58 (s, 1H, CH$_{Ar}$), 7.92 (bs, 1H, NH$_2$), 7.88-7.84 (m, 2H, 2 CH$_{Ar}$), 7.30 (bs, 1H, NH$_2$), 7.25-7.19 (m, 2H, 2 CH$_{Ar}$), 4.88 (s, 1H, NH); HRMS (ESI) calc. for C$_{11}$H$_{11}$N$_4$O$_3$: [M+H]$^+$ 247.08257, found 247.0822.

Compound 97. To a suspension of compound Int-7 in isopropanol (5 mL/mmol) were added 4-methoxybenzylamine (1.1 equivalent) and DIPEA (2.4 equivalents). The suspension was stirred at 60° C. for 30 min. After cooling to room temperature, the resulting precipitate was filtrated and washed with isopropanol to afford pure compound 97 (75%). $^1$H NMR (400 MHz, CDCl$_3$) δ 7.90 (s, 1H, CH$_{Ar}$), 7.30 (d, J=8.7 Hz, 2H, 2 CH$_{Ar}$), 6.88 (d, J=8.7 Hz, 2H, 2 CH$_{Ar}$), 6.17 (bs, 1H, NH), 5.70 (dd, J=10.7 Hz, J=2.2 Hz, 1H, CH), 4.74 (bs, 2H, CH$_2$), 4.15 (m, 1H, CH), 3.78 (m, 1H, CH), 1.63-2.12 (m, 6H, 2 CH+2 CH$_2$); HRMS (ESI) calc. for C$_{18}$H$_{21}$ClN$_5$O$_2$: [M+H]$^+$ 374.13783, found 374.1378.

Compound 98. This compound was synthesized through general synthesis protocol XIII from compound 97 and 2-phenylethanol, and was purified by chromatography on silica gel (elution with dichloromethane/ethyl acetate) to afford pure compound 98 (99%). $^1$H NMR (400 MHz, CDCl$_3$) δ 7.80 (s, 1H, CH$_{Ar}$), 7.24-7.32 (m, 7H, 7 CH$_{Ar}$), 6.86 (d, J=8.6 Hz, 2H, 2 CH$_{Ar}$), 6.01 (bs, 1H, NH), 5.64 (dd, J=10.5 Hz, J=2.1 Hz, 1H, CH), 4.75 (bs, 2H, CH$_2$), 4.56 (t, J=7.8 Hz, 2H, CH$_2$), 4.14 (m, 1H, CH), 3.80 (s, 3H, CH$_3$), 3.75 (m, 1H, CH), 3.16 (t, J=7.8 Hz, 2H, CH$_2$), 1.62-2.09 (m, 6H, 2 CH+2 CH$_2$); HRMS (ESI) calc. for C$_{26}$H$_{30}$N$_5$O$_3$: [M+H]$^+$ 460.23432, found 460.2342.

Compound 99. This compound was synthesized through general synthesis protocol XIII from compound 97 and 3-phenylpropanol, and was purified by chromatography on silica gel (elution with dichloromethane/methanol) to afford pure compound 99 (20%). $^1$H NMR (400 MHz, CDCl$_3$) δ 7.70 (s, 1H, CH$_{Ar}$), 7.16-7.29 (m, 7H, 7 CH$_{Ar}$), 6.83 (d, J=8.7 Hz, 2H, 2 CH$_{Ar}$), 6.45 (bs, 1H, NH), 5.63 (dd, J=10.5 Hz, J=2.3 Hz, 1H, CH), 4.71 (bs, 2H, CH$_2$), 4.39 (t, J=6.5 Hz, 2H, CH$_2$), 4.12 (m, 1H, CH), 3.78 (s, 3H, CH$_3$), 3.73 (m, 1H, CH), 2.81 (t, J=6.5 Hz, 2H, CH$_2$), 2.13 (m, 2H, CH$_2$), 1.59-2.09 (m, 6H, 2 CH+2 CH$_2$).

Compound 100. This compound was synthesized through general synthesis protocol X from 4-aminobenzamide and 2-amino-4,6-dichloropyrimidine and was purified by chromatography on silica gel (eluent dichloromethane/methanol) to afford pure compound 100 (17%). $^1$H NMR (400 MHz, d$_6$-DMSO) δ 9.55 (bs, 1H, NH), 7.87-7.74 (m, 5H, 4 CH$_{Ar}$+NH$_2$), 7.18 (bs, 1H, NH$_2$), 6.82 (bs, 2H, NH$_2$), 6.06 (s, 1H, CH$_{Ar}$); HRMS (ESI) calc. for C$_{11}$H$_{11}$ClN$_5$O: [M+H]$^+$ 264.06466, found 264.0647.

Compound 101 was purchased from Tokyo Chemical Industry Co., Ltd.

Compound 102 was purchased from Sigma-Aldrich Co., Ltd.

Compound 103 was purchased from ABCR GmbH & Co. KG.

Compound 104. This compound was synthesized through general synthesis protocol III from 131, and was purified by chromatography on silica gel (eluent dichloromethane/methanol) to afford pure compound 104 (99%). $^1$H NMR (400 MHz, d$_6$-DMSO) δ 12.94 (bs, 1H, NH), 8.37 (bs, 2H, NH$_2$), 8.15 (s, 1H, CH$_{Ar}$), 7.61 (bs, 1H, NH), 7.40-7.23 (m, 2H, 2 CH$_{Ar}$), 7.12 (t, J=8.9 Hz, 2H, 2 CH$_{Ar}$), 3.57-3.51 (m, 2H, CH$_2$), 2.86 (t, J=7.2 Hz, 2H, CH$_2$); HRMS (ESI) calc. for C$_{13}$H$_{14}$FN$_6$: [M+H]$^+$ 273.12585, found 273.1257.

Compound 105. To a solution of 4-aminobenzamide (1 equivalent) in DMF (1 ml/mmol) was added 4-chloro-3-nitropyridine (1 equivalent). The solution was stirred at 50° C. under argon for 2 h. After cooling, water was added and the resulting precipitate was filtrated, washed with water, toluene and dried in vacuo to afford pure compound 105 (86%). $^1$H NMR (400 MHz, d$_6$-DMSO) δ 9.88 (bs, 1H, NH), 9.10 (s, 1H, CH$_{Ar}$), 8.26 (d, J=6.1 Hz, 1H, CH$_{Ar}$), 7.99 (bs, 1H, NH$_2$), 7.96 (d, J=8.4 Hz, 2H, 2 CH$_{Ar}$), 7.41 (d, J=8.4 Hz, 2H, 2 CH$_{Ar}$), 7.37 (bs, 1H, NH$_2$), 7.02 (d, J=6.1 Hz, 1H, CH$_{Ar}$); HRMS (ESI) calc. for C$_{12}$H$_{11}$N$_4$O$_3$: [M+H]$^+$ 259.08256, found 259.0824.

Compound 106. This compound was synthesized through general synthesis protocol XVI from 4,6-dichloro-5-nitropyrimidine and 4-aminobenzamide to afford pure compound 106 as yellow solid (89%). $^1$H NMR (400 MHz, d$_6$-DMSO) δ 10.21 (bs, 1H, NH), 8.58 (s, 1H, CH$_{Ar}$), 7.93 (bs, 1H, NH$_2$), 7.88 (d, J=8.7 Hz, 2H, 2 CH$_{Ar}$), 7.62 (d, J=8.7 Hz, 2H, 2 CH$_{Ar}$), 7.33 (bs, 1H, NH$_2$); HRMS (ESI) calc. for C$_{11}$H$_9$ClN$_5$O$_3$: [M+H]$^+$ 294.03884, found 294.0387.

Compound 107. To a suspension of 49 (1 equivalent) in methanol (5 ml/mmol) and diethyl ether (5 ml/mmol) was added Pd/C (0.05 equivalent). The reaction mixture was bubbled with argon and then with dihydrogen. The suspension was kept overnight under dihydrogen (1 atm), concentrated in vacuo and then purified by chromatography on silica gel (eluent dichloromethane/methanol/NH$_4$OH) to afford pure compound 107 (78%). $^1$H NMR (400 MHz, d$_6$-DMSO) δ 8.72 (bs, 1H, NH), 8.09 (s, 1H, CH$_{Ar}$), 7.90-7.77 (m, 6H, 5 CH$_{Ar}$+NH$_2$), 7.16 (bs, 1H, NH$_2$), 5.37 (bs, 2H, NH$_2$); HRMS (ESI) calc. for C$_{11}$H$_{12}$N$_5$O: [M+H]$^+$ 230.10363, found 230.1036.

Compound 108. To a solution of 4-mercaptobenzamide (1 equivalent) in ethanol (2 mL/mmol) were added 5-amino-4,6-dichloropyrimidine (1 equivalent) and potassium carbonate (1.2 equivalents). The suspension was refluxed for 4 h, concentrated and purified by chromatography on silica gel (eluent dichloromethane/methanol) to afford pure compound 108 (6%). $^1$H NMR (400 MHz, d$_6$-DMSO) δ 8.06 (bs, 1H, NH$_2$), 8.01 (s, 1H, CH$_{Ar}$), 7.90 (d, J=8.4 Hz, 2H, CH$_{Ar}$), 7.58 (d, J=8.4 Hz, 2H, 2 CH$_{Ar}$), 7.46 (bs, 1H, NH$_2$), 5.84 (bs, 2H, NH$_2$); HRMS (ESI) calc. for C11H$_{10}$ClN$_4$OS: [M+H]$^+$ 281.02584, found 281.0257.

Compound 109. This compound was synthesized through general synthesis protocol XVII from 5-amino-4,6-dichloropyrimidine and 4-methylaniline (1 equivalent) and was purified by precipitation in water to afford pure compound 109 (86%). $^1$H NMR (400 MHz, d$_6$-DMSO) δ 8.72 (bs, 1H, NH), 7.84 (s, 1H, CH$_{Ar}$), 7.58 (d, J=8.3 Hz, 2H, 2 CH$_{Ar}$), 7.14 (d, J=8.3 Hz, 2H, 2 CH$_{Ar}$), 5.86 (bs, 2H, NH$_2$), 2.27 (s, 3H, CH$_3$); HRMS (ESI) calc. for C$_{11}$H$_{12}$ClN$_4$: [M+H]$^+$ 235.07450, found 235.0745.

Compound 110. This compound was synthesized through general synthesis protocol XVII from 5-amino-4,6-dichloropyrimidine and 4-fluoroaniline (1 equivalent) and was purified by precipitation to afford pure compound 110 (74%). $^1$H NMR (400 MHz, d$_6$-DMSO) δ 8.71 (bs, 1H, NH), 7.85 (s, 1H, CH$_{Ar}$), 7.73-7.66 (m, 2H, 2 CH$_{Ar}$), 7.22-7.12 (m, 2H, 2 CH$_{Ar}$), 4.17 (bs, 2H, NH$_2$); HRMS (ESI) calc. for C$_{10}$H$_9$ClFN$_4$: [M+H]$^+$ 239.04943, found 239.0493.

Compound 111 was purchased from Sigma-Aldrich Co., Ltd.

Compound 112. Argon was bubbled through a suspension of 6-chloro-7-deazapurine (1 equivalent), potassium carbonate (1.5 equivalents), trans-1,2-diaminocyclohexane (1.1 equivalents) and 4-iodobenzamide (1 equivalent) in 1,4-dioxane (6.5 mL/mmol). After 10 min, copper iodide (1 equivalent) was added and the mixture was flushed again with argon. The grey suspension was refluxed for 14 h under argon. After cooling, the suspension was diluted with ethyl acetate and washed with a saturated aqueous solution of EDTA. The aqueous layer was extracted with ethyl acetate (four times). The combined organic layer was washed with brine, dried over MgSO$_4$, filtrated and concentrated. The residue was purified by chromatography on silica gel (eluent cyclohexane/ethyl acetate) to afford pure compound 112 (22%). $^1$H NMR (400 MHz, d$_6$-DMSO) δ 8.75 (s, 1H, CH$_{Ar}$), 8.25 (d, J=3.8 Hz, 1H, CH$_{Ar}$), 8.13-8.05 (m, 3H, 2 CH$_{Ar}$, NH$_2$), 8.00 (d, J=8.8 Hz, 2H, 2 CH$_{Ar}$), 7.49 (bs, 1H, NH$_2$), 6.95 (d, J=3.8 Hz, 1H, CH$_{Ar}$); HRMS (ESI) calc. for C$_{13}$H$_{10}$ClN$_4$O: [M+H]$^+$ 273.05376, found 273.0537.

Compound 113. To a solution of 2-amino-6-chloropurine (0.8 equivalent) in a mixture of acetonitrile and water (1/3 v/v, 4 mL/mmol), palladium(II) diacetate (0.04 equivalent), triphenylphosphine-3,3',3"-trisulfonic acid trisodium salt (0.2 equivalent), Cs$_2$CO$_3$ (2.4 equivalents) and 4-carbamoylphenylboronic acid (1 equivalent) were added. The solution was stirred for 5 min under microwave irradiation at 150° C. After cooling to 4° C., the reaction mixture was filtrated and the crude solid was purified by chromatography on silica gel (eluent dichloromethane/methanol) to afford pure compound 113 (23%). $^1$H NMR (400 MHz, d$_6$-DMSO)

δ 12.70 (bs, 1H, NH), 8.79 (d, J=8.5 Hz, 2H, 2 CH$_{Ar}$), 8.14 (s, 1H, CH$_{Ar}$), 8.07 (bs, 1H, NH$_2$), 8.02 (d, J=8.5 Hz, 2H, 2 CH$_{Ar}$), 7.45 (bs, 1H, NH$_2$), 6.43 (bs, 2H, NH$_2$); HRMS (ESI) calc. for C$_{12}$H$_{11}$N$_6$O: [M+H]$^+$ 255.09889, found 255.0988.

Compound 114. To a suspension of 3-fluoro-4-nitropyridine-N-oxide (1 equivalent) in absolute ethanol (1 mL/mmol) was added 4-aminobenzamide (3 equivalents). The suspension was refluxed for 8 h under argon. After cooling, methanol was added (15 mL/mmol) and the suspension was stirred for 1 h then filtrated. The precipitate was suspended in methanol (15 mL/mmol). The suspension was stirred for 1 h, filtrated, and the precipitate was washed with methanol to afford pure compound 114 (96%). $^1$H NMR (400 MHz, d$_6$-DMSO) δ 9.59 (bs, 1H, NH), 8.12 (d, J=7.3 Hz, 1H, CH$_{Ar}$), 7.97 (bs, 1H, NH$_2$), 7.95-7.89 (m, 3H, 3 CH$_{Ar}$), 7.71 (dd, J=7.3, 1.9 Hz, 1H, CH$_{Ar}$), 7.45 (d, J=8.6 Hz, 2H, CH$_{Ar}$), 7.36 (bs, 1H, NH$_2$); HRMS (ESI) calc. for C$_{12}$H$_{11}$N$_4$O$_4$: [M+H]$^+$ 275.07803, found 275.0775.

Compound 115. To a suspension of 148 (1 equivalent) in methanol (10 ml/mmol) was added Pd/C 10% (0.05 equivalent). The reaction mixture was bubbled with argon and then with dihydrogen. The suspension was kept overnight under dihydrogen (1 atm) and was purified by chromatography on silica gel (eluent dichloromethane/methanol). The pure fractions were then evaporated and the residual oil was precipitated with HCl in diethyl ether 1 M which after filtration afforded pure compound 115 (62%). $^1$H NMR (400 MHz, d$_6$-DMSO) δ 10.14 (bs, 1H, NH), 7.98 (bs, 1H, NH$_2$), 7.94 (d, J=8.7 Hz, 2H, 2 CH$_{Ar}$), 7.46-7.38 (m, 3H, 3 CH$_{Ar}$), 7.38-7.29 (m, 2H, 1 CH$_{Ar}$+NH$_2$), 7.02 (dd, J=7.9, 5.9 Hz, 1H, CH$_{Ar}$); HRMS (ESI) calc. for C$_{12}$H$_{13}$N$_4$O: [M+H]$^+$ 229.10838, found 229.1083.

Compound 116. To a suspension of 16 (1 equivalent) in methanol (10 mL/mmol) was added Pd/C 10% (0.05 equivalent). The reaction mixture was bubbled with argon and then with dihydrogen. The suspension was kept under dihydrogen (1 atm) at 50° C. for four days. It was purified by chromatography on silica gel (eluent dichloromethane/methanol) to afford pure compound 116 (6 mg, 6%). $^1$H NMR (400 MHz, d$_6$-DMSO) δ 9.31 (s, 1H, CH$_{Ar}$), 9.14 (s, 1H, CH$_{Ar}$), 9.05 (s, 1H, CH$_{Ar}$), 8.16-8.06 (m, 5H, 4 CH$_{Ar}$+NH$_2$), 7.53 (s, 1H, NH$_2$); HRMS (ESI) calc. for C$_{12}$H$_{10}$N$_5$O: [M+H]$^+$ 240.08853, found 240.0884.

Compound 117. To a solution of 2-6-diaminopurine (1 equivalent) in DMF (1 mL/mmol), CuI (1.1 equivalents), N,N'-dimethylethylenediamine (2.2 equivalents), K$_3$PO$_4$ (4 equivalents) and 4-iodobenzyl alcohol (1.3 equivalents) were added. The solution was stirred overnight at 90° C. under argon. After concentration under reduced pressure, the reaction mixture was diluted with dichloromethane and extracted with a saturated aqueous solution of ethylenediaminetetraacetic acid (EDTA). The organic layer was washed with water and brine, then dried over magnesium sulfate. After filtration and concentration under reduced pressure the crude product was purified by chromatography on silica gel (eluent dichloromethane/methanol) to afford pure compound 117 (7%). $^1$H NMR (400 MHz, d$_6$-DMSO) δ 9.40 (bs, 1H, NH), 8.25 (s, 1H, CH$_{Ar}$), 7.98-7.94 (m, 2H, 2 CH$_{Ar}$), 7.84-7.78 (m, 2H, 2 CH$_{Ar}$), 7.48 (d, J=8.6 Hz, 2H, 2 CH$_{Ar}$), 7.23 (d, J=8.6 Hz, 2H, 2 CH$_{Ar}$), 6.22 (bs, 2H, NH$_2$), 5.29 (t, J=5.8 Hz, 1H, OH), 5.05 (t, J=5.7 Hz, 1H, OH), 4.57 (d, J=5.8 Hz, 2H, CH$_2$), 4.45 (d, J=5.7 Hz, 2H, CH$_2$); HRMS (ESI) calc. for C$_{19}$H$_{19}$N$_6$O$_2$: [M+H]$^+$ 363.15640, found 363.1564.

Compound 118. This compound was synthesized through general synthesis protocol VI from compound 81 and was purified by chromatography on silica gel (eluent dichloromethane/methanol) to afford pure compound 118 (47%). $^1$H NMR (400 MHz, d$_6$-DMSO) δ 8.58 (bs, 1H, CH$_{Ar}$), 7.91 (bs, 1H, NH), 7.79 (d, J=7.8 Hz, 2H, 2 CH$_{Ar}$), 7.65-7.57 (m, 2H, 2 CH$_{Ar}$), 7.48 (t, J=7.4 Hz, 1H, CH$_{Ar}$), 4.26 (bs, 1H, CH), 1.42 (d, J=7.0 Hz, 3H, CH$_3$); HRMS (ESI) calc. for C$_{14}$H$_{13}$ClN$_5$O$_2$: [M+H]$^+$ 318.07523, found 318.0753.

Compound 119. This compound was synthesized through general synthesis protocol VIII from 93 and 1-serine to afford pure compound 119 (91%). $^1$H NMR (400 MHz, d$_6$-DMSO) δ 8.27 (s, 1H, CH$_{Ar}$), 7.94 (bs, 1H, NH$_2$), 7.82 (d, J=8.4 Hz, 2H, 2 CH$_{Ar}$), 7.40 (d, J=5.1 Hz, 1H, NH), 7.34 (bs, 1H, NH$_2$), 7.29 (d, J=8.3 Hz, 2H, 2 CH$_{Ar}$), 5.85 (bs, 1H, OH), 5.40 (s, 2H, CH$_2$), 3.93-3.79 (m, 2H, CH$_2$), 3.44-3.37 (m, 1H, CH); HRMS (ESI) calc. for C$_{16}$H$_{16}$ClN$_6$O$_4$: [M+H]$^+$ 391.09161, found 391.0922.

Compound 120. This compound was synthesized through general synthesis protocol XVI from 4,6-dichloro-5-nitropyrimidine (1 equivalent) and 4-aminoacetanilide (1 equivalent). It was stirred at room temperature under argon for 7 h. The suspension was then filtered and the precipitate was washed with ethyl acetate. The filtrate was concentrated until precipitation. The precipitate was filtrated to afford pure compound 120 (25%). $^1$H NMR (400 MHz, d$_6$-DMSO) δ 10.02 (bs, 1H, NH), 9.99 (bs, 1H, NH), 8.47 (s, 1H, CH$_{Ar}$), 7.57 (d, J=8.9 Hz, 2H, 2 CH$_{Ar}$), 7.39 (d, J=8.9 Hz, 2H, 2 CH$_{Ar}$), 2.04 (s, 3H, CH$_3$); HRMS (ESI) calc. for C$_{12}$H$_{11}$ClN$_5$O$_3$: [M+H]$^+$ 308.05449, found 308.0543.

Compound 121. This compound was synthesized through general synthesis protocol VII from compound 93 and 1-alanine tert-butyl ester. After concentration, the crude product was purified by chromatography on silica gel (eluent dichloromethane/methanol) to afford pure compound 121 (79%). $^1$H NMR (400 MHz, d$_6$-DMSO, 60° C.) δ 8.25 (s, 1H, NH), 8.20 (bs, 1H, CH$_{Ar}$), 7.83 (d, J=8.3 Hz, 2H, 2 CH$_{Ar}$), 7.33 (d, J=8.3 Hz, 2H, 2 CH$_{Ar}$), 5.41 (s, 2H CH$_2$), 4.53 (bs, 1H, CH), 1.46 (d, J=7.3 Hz, 3H, CH$_3$), 1.43-1.35 (m, 9H, 3 CH$_3$); HRMS (ESI) calc. for C$_{20}$H$_{24}$ClN$_6$O$_3$: [M+H]$^+$ 431.15929, found 431.1600.

Compound 122. A mixture of 49 (1 equivalent) and urea (43 equivalents) was heated to 160° C. Once the temperature reached the melting point of urea, ethanesulfonic acid (25 μL/mmol) was added. The resulting solution was stirred at 160° C. for 15 h. After cooling down to room temperature, it was diluted with water (13 mL/mmol), filtered, washed with water and dried under reduced pressure. The crude product was purified by chromatography on silica gel (eluent dichloromethane/methanol). The purest fractions were combined and purified by reverse phase chromatography (eluent water/methanol) to afford pure compound 122 (13%). $^1$H NMR (400 MHz, d$_6$-DMSO) δ 12.40 (bs, 1H, NH), 8.46 (s, 1H, CH$_{Ar}$), 8.08 (bs, 1H, NH$_2$), 8.03 (d, J=8.6 Hz, 2H, 2 CH$_{Ar}$), 7.74 (d, J=8.6 Hz, 2H, 2 CH$_{Ar}$), 7.49 (bs, 1H, NH$_2$); HRMS (ESI) calc. for C$_{12}$H$_9$ClN$_5$O$_2$: [M+H]$^+$ 290.04393, found 290.0441.

Compound 123. This compound was synthesized through general synthesis protocol XVI from 4,6-dichloro-5-nitropyrimidine (1 equivalent) and 4-methylaminobenzoic acid (1.05 equivalent) to afford pure compound 123 (68%). $^1$H NMR (400 MHz, d$_6$-DMSO) δ 13.16 (bs, 1H, COOH), 8.74 (s, 1H, CH$_{Ar}$), 7.91 (d, J=8.7 Hz, 2H, 2 CH$_{Ar}$), 7.48 (d, J=8.7 Hz, 2H, 2 CH$_{Ar}$), 3.57 (s, 3H, CH$_3$); HRMS (ESI) calc. for C$_{12}$H$_{10}$ClN$_4$O$_4$: [M+H]$^+$ 309.03851, found 309.0385.

Compound 124. To a suspension of 106 (1 equivalent) in ethanol (5 ml/mmol) was added sodium thiomethoxide (2 equivalents). The suspension was stirred for 1 h at room temperature and then diethyl ether (45 mL/mmol) was added. After filtration the solid was purified by chromatography on silica gel (eluent dichloromethane/methanol) to afford pure compound 124 (78%). $^1$H NMR (400 MHz, d$_6$-DMSO) δ 10.61 (bs, 1H, NH), 8.56 (s, 1H, CH$_{Ar}$), 7.97 (bs, 1H, NH$_2$), 7.90 (d, J=8.7 Hz, 2H, 2 CH$_{Ar}$), 7.69 (d, J=8.7 Hz, 2H, 2 CH$_{Ar}$), 7.36 (bs, 1H, NH$_2$), 2.51 (s, 3H, CH$_3$); HRMS (ESI) calc. for C$_{12}$H$_{12}$N$_5$O$_3$S: [M+H]$^+$ 306.06554, found 306.0654.

Compound 125. To a solution of 123 (1 equivalent) in anhydrous dichloromethane (8 mL/mmol) was added thionyl chloride (8 equivalents). The solution was stirred for 2 h at room temperature and then evaporated. The residual solid was suspended in anhydrous dichloromethane (5 mL/mmol) and NH$_3$ in 1,4-dioxane (0.5 mol/L, 5 equivalents) was added. After 2 h, water was added and the reactionnal mixture separated. The aqueous layer was extracted with dichloromethane. The organic layer was washed with brine and was dried over MgSO$_4$. After evaporation under reduced pressure the crude product was purified by chromatography on silica gel (eluent dichloromethane/methanol) to afford pure compound 125 (83%). $^1$H NMR (400 MHz, d$_6$-DMSO) δ 8.72 (s, 1H, CH$_{Ar}$), 8.05 (bs, 1H, NH$_2$), 7.87 (d, J=8.7 Hz, 2H, 2 CH$_{Ar}$), 7.47 (bs, 1H, NH$_2$), 7.44 (d, J=8.6 Hz, 2H, 2 CH$_{Ar}$), 3.55 (s, 3H, CH$_3$); HRMS (ESI) calc. for C$_{12}$H$_{11}$ClN$_5$O$_3$: [M+H]$^+$ 308.05449, found 308.0545.

Compound 126. To a suspension of 125 (1 equivalent) in a mixture of ethyl acetate (4 mL/mmol) and ethanol (4 mL/mmol) was added tin chloride dihydrate (4 equivalents). After 7 h under reflux, the suspension was concentrated to dryness and the crude product was purified by chromatography on silica gel (eluent dichloromethane/methanol) to afford pure compound 126 (54%). $^1$H NMR (400 MHz, d$_6$-DMSO) δ 8.14 (s, 1H, CH$_{Ar}$), 7.83 (bs, 1H, NH$_2$), 7.80 (d, J=8.9 Hz, 2H, 2 CH$_{Ar}$), 7.18 (bs, 1H, NH$_2$), 6.86 (d, J=8.8 Hz, 2H, 2 CH$_{Ar}$), 5.05 (bs, 2H, NH$_2$), 3.34 (s, 3H, CH$_3$); HRMS (ESI) calc. for C$_{12}$H$_{13}$ClN$_5$O: [M+H]$^+$ 278.08031, found 278.0802.

Compound 127. This compound was synthesized through general synthesis protocol II from 9 and [3-(3-fluorophenyl)propyl]amine (10 equivalents) to afford pure compound 127 (41%). $^1$H NMR (400 MHz, d$_6$-DMSO) δ 12.13 (bs, 1H, NH), 7.62 (bs, 2H, CH$_{Ar}$+NH), 7.34-7.23 (m, 3H, 3 CH$_{Ar}$), 7.08-7.01 (m, 2H, 2 CH$_{Ar}$), 7.01-6.93 (m, 1H, CH$_{Ar}$), 6.82 (d, J=8.6 Hz, 2H, CH$_{Ar}$), 6.28 (bs, 1H, NH), 4.54 (bs, 2H, CH$_2$), 3.69 (s, 3H, CH$_3$), 3.27-3.17 (m, 2H, CH$_2$), 2.62 (t, J=6.5 Hz, 2H, CH$_2$), 1.84-1.75 (m, 2H, CH$_2$); HRMS (ESI) calc. for C$_{22}$H$_{24}$FN$_6$O: [M+H]$^+$ 407.19901, found 407.1995.

Compound 128. This compound was synthesized through general synthesis protocol III from compound 127, and was purified by chromatography on silica gel (eluent dichloromethane/methanol) to afford pure compound 128 (17%). $^1$H NMR (400 MHz, CD$_3$OD) δ 7.76 (s, 1H, CH$_{Ar}$), 7.26 (td, J=8.2, 6.1 Hz, 1H, CH$_{Ar}$), 7.03 (d, J=7.8 Hz, 1H, CH$_{Ar}$), 6.98-6.92 (m, 1H, CH$_{Ar}$), 6.88 (td, J=8.2, 1.9 Hz, 1H, CH$_{Ar}$), 3.37 (t, J=7.0 Hz, 2H, CH$_2$), 2.75-2.65 (m, 2H, CH$_2$), 1.96-1.84 (m, 2H, CH$_2$); HRMS (ESI) calc. for C$_{14}$H$_{16}$FN$_6$: [M+H]$^+$ 287.14150, found 287.1416.

Compound 129. To a suspension of 124 (1 equivalent) in methanol (10 ml/mmol) was added Pd/C 10% (0.1 equivalent). The reaction mixture was bubbled with argon and then with dihydrogen. The suspension was kept overnight under dihydrogen (1 atm), and was purified by chromatography on silica gel (eluent dichloromethane/methanol) to afford pure compound 129 (16%). $^1$H NMR (400 MHz, CD$_3$OD) δ 8.11 (s, 1H, CH$_{Ar}$), 7.85 (d, J=8.9 Hz, 2H, 2 CH$_{Ar}$), 7.75 (d, J=8.9 Hz, 2H, 2 CH$_{Ar}$), 2.59 (s, 3H, CH$_3$). HRMS (ESI) calc. for C$_{12}$H$_{14}$N$_5$OS: [M+H]$^+$ 276.09135, found 276.0913.

Compound 130. To a solution of 6-amino-2-chloropurine (0.8 equivalent) in a mixture of acetonitrile and water (1/3 v/v, 4 mL/mmol), palladium(II) diacetate (0.04 equivalent), triphenylphosphine-3,3',3"-trisulfonic acid trisodium salt (0.2 equivalent), Cs$_2$CO$_3$ (2.4 equivalents) and 4-carbamoylphenylboronic acid (1 equivalent) were added. The solution was stirred for 10 min under microwave irradiation at 150° C. After cooling to 4° C., the reaction mixture was filtrated and the crude solid was purified by chromatography on silica gel (eluent dichloromethane/methanol) and crystallized from ethanol to afford compound 130 (3%). $^1$H NMR (400 MHz, d$_6$-DMSO) δ 12.93 (s, 1H, NH), 8.38 (d, J=8.5 Hz, 2H, 2 CH$_{Ar}$), 8.12 (bs, 1H, NH$_2$), 8.02 (bs, 1H, NH$_2$), 7.95 (d, J=8.6 Hz, 2H, 2 CH$_{Ar}$), 7.23 (bs, 2H, NH$_2$); HRMS (ESI) calc. for C$_{12}$H$_{11}$N$_6$O: [M+H]$^+$ 255.09889, found 255.0988.

Compound 131. This compound was synthesized through general synthesis protocol II from compound 9 and 4-fluorophenylethylamine (10 equivalents) to afford pure compound 131 (74%). $^1$H NMR (400 MHz, d$_6$-DMSO) δ 12.13 (bs, 1H, NH), 7.64 (bs, 2H, NH+CH$_{Ar}$), 7.27 (d, J=8.6 Hz, 2H, 2 CH$_{Ar}$), 7.20 (bs, 2H, 2 CH$_{Ar}$), 7.08 (t, J=8.9 Hz, 2H, 2 CH$_{Ar}$), 6.83 (d, J=8.6 Hz, 2H, 2 CH$_{Ar}$), 6.26 (bs, 1H, NH), 4.56 (bs, 2H, CH$_2$), 3.50-3.38 (m, 2H, CH$_2$), 2.79 (t, J=7.3 Hz, 2H, CH$_2$); HRMS (ESI) calc. for C$_{12}$H$_{22}$FN$_6$O: [M+H]$^+$ 393.18336, found 393.1831.

Compound 132 was purchased from Fisher Scientific SAS.

Compound 133 was purchased from Tokyo Chemical Industry Co., Ltd.

Compound 134 was purchased from Sigma-Aldrich Co., Ltd.

Compound 135 was purchased from Sigma-Aldrich Co., Ltd.

Compound 136 was purchased from Fluorochem, Ltd.

Compound 137 was purchased from Sigma-Aldrich Co., Ltd.

Compound 138 was purchased from Tokyo Chemical Industry Co., Ltd.

Compound 139 was purchased from Tokyo Chemical Industry Co., Ltd.

Compound 140. This compound was synthesized through general synthesis protocol XV from 4-amino-2,6-dichloropyrimidine and 4-aminobenzamide (1.1 equivalents) to afford pure compound 140 (39%). $^1$H NMR (400 MHz, d$_6$-DMSO) δ 10.56 (s, 1H, NH), 10.21 (s, 1H, NH), 8.13-7.73 (m, 8H, 2 NH$_2$+4 CH$_{Ar}$), 7.66 (d, J=8.5 Hz, 2H, 2 CH$_{Ar}$), 7.55 (d, J=8.2 Hz, 2H, 2 CH$_{Ar}$), 7.30 (m, 2H, 2 NH$_2$), 5.64 (s, 1H, CH$_{Ar}$); HRMS (ESI) calc. for C$_{18}$H$_{18}$N$_7$O$_2$: [M+H]$^+$ 364.15195, found 364.1518.

Compound 141. To a suspension of 105 (1 equivalent) in a mixture of methanol (4 ml/mmol) and diethyl ether (4 ml/mmol) was added Pd/C 10% (0.04 equivalent). The reaction mixture was bubbled with argon and then with dihydrogen. The suspension was kept overnight under dihydrogen (1 atm), and was purified by chromatography on silica gel (eluent dichloromethane/methanol) to afford pure compound 141 (62%). $^1$H NMR (400 MHz, d$_6$-DMSO) δ 7.97 (s, 1H, CH$_{Ar}$), 7.88 (bs, 1H, NH), 7.81 (d, J=8.6 Hz, 2H, 2 CH$_{Ar}$), 7.77 (bs, 1H, NH$_2$), 7.71 (d, J=5.3 Hz, 1H, CH$_{Ar}$), 7.12 (bs, 1H, NH$_2$), 7.06 (d, J=8.8 Hz, 2H, 2 CH$_{Ar}$), 7.04 (d, J=5.6 Hz, 1H, CH$_{Ar}$), 4.99 (bs, 2H, NH$_2$). HRMS (ESI) calc. for C$_{12}$H$_{13}$N$_4$O: [M+H]$^+$ 229.10838, found 229.1084.

Compound 142. This compound was synthesized through general synthesis protocol XV from 5-amino-4,6-dichloropyrimidine and 4-(aminomethyl)benzamide to afford pure compound 142 (51%). $^1$H NMR (400 MHz, d$_6$-DMSO) δ

7.91 (bs, 1H, NH$_2$), 7.82 (d, J=8.3 Hz, 2H, 2 CH$_{Ar}$), 7.72 (s, 1H, CH$_{Ar}$), 7.48-7.40 (m, 1H, NH), 7.37 (d, J=8.3 Hz, 2H, 2 CH$_{Ar}$), 7.30 (bs, 1H, NH$_2$), 5.11 (bs, 2H, NH$_2$), 4.67 (d, J=5.7 Hz, 2H, CH$_2$); HRMS (ESI) calc. for C$_{12}$H$_{13}$ClN$_5$O: [M+H]$^+$ 278.08031, found 278.0802.

Compound 143. To a solution of 4-aminobenzamide (1 equivalent) in anhydrous DMF (1 ml/mmol) were successively added 2,4-dichloro-3-nitropyridine (1 equivalent) and potassium carbonate (1.2 equivalents). The resulting suspension was stirred for 8 h at 100° C. under argon, concentrated in vacuo and then purified by chromatography on silica gel (eluent dichloromethane/methanol) to afford pure compound 143 (42%). $^1$H NMR (400 MHz, d$_6$-DMSO) δ 9.43 (s, 1H, NH), 8.12 (d, J=6.0 Hz, 1H, CH$_{Ar}$), 7.97 (bs, 1H, NH$_2$), 7.93 (d, J=8.6 Hz, 2H, 2 CH$_{Ar}$), 7.47-7.27 (m, 3H, NH$_2$+2 CH$_{Ar}$), 7.16 (d, J=6.0 Hz, 1H, CH$_A$). HRMS (ESI) calc. for C$_{12}$H$_{10}$ClN$_4$O$_3$: [M+H]$^+$ 293.04359, found 293.0433.

Compound 144. This compound was synthesized through general synthesis protocol XVII from 5-amino-4,6-dichloropyrimidine and 4-chlorobenzamide (1 equivalent) and was purified by crystallization from methanol to afford pure compound 144 (73%). $^1$H NMR (400 MHz, d$_6$-DMSO) δ 8.92 (bs, 1H, NH), 7.88 (s, 1H, CH$_{Ar}$), 7.82-7.75 (m, 2H, 2 CH$_{Ar}$), 7.41-7.33 (m, 2H, 2 CH$_{Ar}$), 6.67 (bs, 2H, NH$_2$); HRMS (ESI) calc. for C$_{10}$H$_9$Cl$_2$N$_4$: [M+H]$^+$ 255.01988, found 255.0199.

Compound 145. To a solution of compound 106 (1 equivalent) in methanol (10 mL/mmol) were added glycine (1 equivalent) and diisopropylethylamine (2 equivalents). The solution was refluxed for 1 h, concentrated under reduced pressure then suspended in water. The suspension was filtered and the solid was washed several times with water to afford pure compound 145 (99%). $^1$H NMR (400 MHz, d$_6$-DMSO) δ 12.85 (bs, 1H, COOH), 10.96 (bs, 1H, NH), 9.58 (t, J=5.6 Hz, 1H, NH), 8.18 (s, 1H, CH$_{Ar}$), 7.94 (bs, 1H, NH$_2$), 7.88 (d, J=8.7 Hz, 2H, 2 CH$_{Ar}$), 7.72 (d, J=8.7 Hz, 2H, 2 CH$_{Ar}$), 7.33 (bs, 1H, NH$_2$), 4.23 (d, J=5.6 Hz, 2H, CH$_2$); HRMS (ESI) calc. for C$_{13}$H$_{13}$N$_6$O$_5$: [M+H]$^+$ 333.09416, found 333.0941.

Compound 146. This compound was synthesized through general synthesis protocol III from compound Int-1 and was purified by precipitation in water to afford pure compound 146 (63%). $^1$H NMR (400 MHz, d$_6$-DMSO) δ 8.56 (s, 1H, CH$_{Ar}$), 7.91 (bs, 2H, NH$_2$), 7.85-7.77 (m, 2H, 2 CH$_{Ar}$), 7.65-7.57 (m, 2H, 2 CH$_{Ar}$), 7.52-7.45 (m, 1H, CH$_{Ar}$); HRMS (ESI) calc. for C$_{11}$H$_9$ClN$_5$: [M+H]$^+$ 246.05410, found 246.0540.

Compound 147. To a refluxed suspension of 143 (1 equivalent) in ethyl acetate (5 ml/mmol) was added portionwise tin chloride dihydrate (5.7 equivalents) over 2 h 30.

After cooling, the reaction was quenched by the addition of a saturated aqueous solution of NaHCO$_3$. The aqueous layer was extracted four times with ethyl acetate. The combined organic layers were washed with brine, dried over MgSO$_4$, filtrated, concentrated in vacuo, and purified by chromatography on silica gel (eluent dichloromethane/methanol) to afford pure compound 147 (51%). $^1$H NMR (400 MHz, d$_6$-DMSO) δ 8.05 (bs, 1H, NH), 7.82 (d, J=8.7 Hz, 2H, 2 CH$_{Ar}$), 7.79 (s, 1H, NH$_2$), 7.52 (d, J=5.2 Hz, 1H, CH$_{Ar}$), 7.15 (bs, 1H, NH$_2$), 7.10 (d, J=8.7 Hz, 2H, 2 CH$_{Ar}$), 7.06 (d, J=5.3 Hz, 1H, CH$_{Ar}$), 5.14 (bs, 2H, NH$_2$); HRMS (ESI) calc. for C$_{12}$H$_{12}$ClN$_4$O: [M+H]$^+$ 263.06942, found 263.0692.

Compound 148. To a solution of 4-aminobenzamide (1 equivalent) in absolute ethanol (0.6 ml/mmol) were added 2-chloro-3-nitropyridine (1 equivalent) and potassium carbonate (1.2 equivalents). The suspension was heated under microwave irradiation at 170° C. for 1 h 30, then purified by chromatography on silica gel (eluent dichloromethane/methanol) to afford pure compound 148 (19%). $^1$H NMR (400 MHz, d$_6$-DMSO) δ 10.06 (s, 1H, NH), 8.59-8.53 (m, 2H, 2 CH$_{Ar}$), 7.89 (bs, 1H, NH$_2$), 7.88 (d, J=8.8 Hz, 2H, CH$_{Ar}$), 7.78 (d, J=8.8 Hz, 2H, 2 CH$_{Ar}$), 7.27 (m, 1H, NH$_2$), 7.09-7.03 (m, 1H, CH$_{Ar}$); HRMS (ESI) calc. for C$_{12}$H$_{11}$N$_4$O$_3$: [M+H]$^+$ 259.08257, found 259.0823.

Compound 149. To a solution of 4-aminobenzamide (1 equivalent) in ethanol (2 mmol/mL) was added 4,6-dichloropyrimidine (1 equivalent) and the solution was refluxed for 7 h. After cooling, the precipitate was filtrated and recrystallized from methanol (60 mL) to afford pure compound 149 (37%). $^1$H NMR (400 MHz, d$_6$-DMSO) δ 10.09 (bs, 1H, NH), 8.55 (s, 1H, CH$_{Ar}$), 7.91-7.81 (m, 3H, 2 CH$_{Ar}$+NH$_2$), 7.72 (d, J=8.7 Hz, 2H, 2 CH$_{Ar}$), 7.24 (bs, 1H, NH$_2$), 6.88 (s, 1H, CH$_{Ar}$); HRMS (ESI) calc. for C$_{11}$H$_{10}$ClN$_4$O: [M+H]$^+$ 249.05376, found 249.0536.

Compound 150. This compound was synthesized through general synthesis protocol XVII from 5-amino-4,6-dichloropyrimidine and aniline (1 equivalent), and was filtrated from the reaction mixture to afford pure compound 150 (50%). $^1$H NMR (400 MHz, d$_6$-DMSO) δ 8.58 (bs, 1H, NH), 7.86 (s, 1H, CH$_{Ar}$), 7.73-7.65 (m, 2H, 2 CH$_{Ar}$), 7.37-7.29 (m, 2H, 2 CH$_{Ar}$), 7.08-7.01 (m, 1H, CH$_{Ar}$), 5.44 (bs, 2H, NH$_2$); HRMS (ESI) calc. for C$_{10}$H$_{10}$ClN$_4$: [M+H]$^+$ 221.05885, found 221.0589.

Compound 151. To a solution of 4,6-dichloro-5-nitropyrimidine (1 equivalent) in THF (2.5 mL/mmol), NaHCO$_3$ (1.5 equivalents) and 4-aminoacetanilide (1 equivalent) were added and stirred at room temperature under argon for 7 h. The suspension was filtered and the precipitate washed with ethyl acetate. The precipitate was then triturated in warm methanol and filtered to afford pure compound 151 (18%). $^1$H NMR (400 MHz, d$_6$-DMSO) δ 10.87 (bs, 2H, NH), 9.99 (bs, 2H, NH), 8.10 (s, 1H, CH$_{Ar}$), 7.59 (d, J=8.8 Hz, 4H, 2 CH$_{Ar}$), 7.51 (d, J=8.8 Hz, 4H, 2 CH$_{Ar}$), 2.05 (s, 6H, 2 CH$_3$); HRMS (ESI) calc. for C$_{20}$H$_{20}$N$_7$O$_4$: [M+H]$^+$ 422.15713, found 422.1570.

Compound 152. To a suspension of 147 in trimethyl orthoformate (5 mL/mmol) was added ethanesulfonic acid (25 μL/mmol). The mixture was stirred for 24 h under reflux. The crude mixture was concentrated under reduced pressure, to afford pure compound 152 (82%). $^1$H NMR (400 MHz, d$_6$-DMSO) δ 8.90 (s, 1H, CH$_{Ar}$), 8.26 (d, J=5.6 Hz, 1H, CH$_{Ar}$), 8.17 (bs, 1H, NH$_2$), 8.14 (d, J=8.6 Hz, 2H, 2 CH$_{Ar}$), 7.83 (d, J=8.6 Hz, 2H, 2 CH$_{Ar}$), 7.76 (d, J=5.6 Hz, 1H, CH$_{Ar}$), 7.56 (bs, 1H, NH$_2$); HRMS (ESI) calc. for C$_{13}$H$_{10}$ClN$_4$O: [M+H]$^+$ 273.05377, found 273.0535.

Compound 153. This compound was synthesized through general synthesis protocol VI from compound 121, was purified by extraction dichloromethane/water to afford pure compound 153 (95%). $^1$H NMR (400 MHz, d$_6$-DMSO) δ 12.63 (bs, 1H, COOH), 8.51 (d, J=7.3 Hz, 1H, NH), 8.33 (s, 1H, CH$_{Ar}$), 7.93 (bs, 1H, NH$_2$), 7.83 (d, J=8.3 Hz, 2H, 2 CH$_{Ar}$), 7.36 (bs, 1H, NH$_2$), 7.31 (d, J=8.3 Hz, 2H, 2 CH$_{Ar}$), 5.42 (s, 2H, CH$_2$), 4.68-4.52 (m, 1H, CH), 1.46 (d, J=7.3 Hz, 3H, CH$_3$); HRMS (ESI) calc. for C$_{16}$H$_{16}$ClN$_6$O$_3$: [M+H]$^+$ 375.09669, found 375.0965.

Compound 154. A suspension of 112 in NH$_4$OH 30% (22 mL/mmol), was heated to 100° C. for 1 h 30 under microwave irradiation. After concentration under reduced pressure, the reaction mixture was purified by chromatography on silica gel (eluent dichloromethane/methanol), to afford pure compound 154 (67%). $^1$H NMR (400 MHz, d$_6$-DMSO) δ 8.16 (s, 1H, CH$_{Ar}$), 8.04 (bs, 1H, NH$_2$), 8.03-7.97 (m, 4H, 4 CH$_{Ar}$), 7.67 (d, J=3.7 Hz, 1H, CH$_{Ar}$), 7.41 (bs, 1H, NH$_2$), 7.20 (bs, 2H, NH$_2$), 6.81 (d, J=3.7 Hz, 1H, CH$_{Ar}$); HRMS (ESI) calc. for C$_{13}$H$_{12}$N$_5$O: [M+H]$^+$ 254.10364, found 254.1033.

Compound 155. To a suspension of 106 (1 equivalent) in methanol (8 mL/mmol), sodium methoxide (4 equivalents) was added. The suspension was stirred at 50° C. for 40 min under argon. After concentration under reduced pressure, the crude product was purified by chromatography on silica gel (eluent dichloromethane/methanol) to afford pure compound 155 (99%). $^1$H NMR (400 MHz, d$_6$-DMSO) δ 9.96 (bs, 1H, NH), 8.45 (s, 1H, CH$_{Ar}$), 7.92 (bs, 1H, NH$_2$), 7.86 (d, J=8.7 Hz, 2H, 2 CH$_{Ar}$), 7.63 (d, J=8.7 Hz, 2H, 2 CH$_{Ar}$), 7.31 (bs, 1H, NH$_2$), 4.02 (s, 3H, CH$_3$); HRMS (ESI) calc. for C$_{12}$H$_{12}$N$_5$O$_4$: [M+H]$^+$ 290.08838, found 290.0886.

Compound 156. To a suspension of 120 (1 equivalent) in a mixture of ethyl acetate (2 mL/mmol) and ethanol (2 mL/mmol) was added tin chloride dihydrate (5 equivalents). After 24 h under reflux, the suspension was concentrated to dryness and the crude product was purified by chromatography on silica gel (eluent dichloromethane/methanol) to afford pure compound 156 (29%). $^1$H NMR (400 MHz, d$_6$-DMSO) δ 9.87 (bs, 1H, NH), 8.53 (bs, 1H, NH), 7.82 (s, 1H, CH$_{Ar}$), 7.58 (d, J=9.1 Hz, 2H, 2 CH$_{Ar}$), 7.52 (d, J=9.1 Hz, 2H, 2 CH$_{Ar}$), 5.38 (bs, 2H, NH$_2$), 2.02 (s, 3H, CH$_3$); HRMS (ESI) calc. for C$_{12}$H$_{13}$ClN$_5$O: [M+H]$^+$ 278.08031, found 278.0808.

Compound 157. To a suspension of sodium hydride (3 equivalents) in benzyl alcohol (5.5 mL/mmol) was added 106 (1 equivalent). The suspension was stirred for 2 h at room temperature and then diethyl ether (27 mL/mmol) was added. The suspension was filtered and the solid was purified by chromatography on silica gel (eluent dichloromethane/methanol) to afford pure compound 157 (81%). $^1$H NMR (400 MHz, d$_6$-DMSO) δ 9.98 (bs, 1H, NH), 8.46 (s, 1H, CH$_{Ar}$), 7.92 (bs, 1H, NH$_2$), 7.86 (d, J=8.7 Hz, 2H, 2 CH$_{Ar}$), 7.63 (d, J=8.7 Hz, 2H, 2 CH$_{Ar}$), 7.49-7.33 (m, 5H, 5 CH$_{Ar}$), 7.32 (bs, 1H, NH$_2$), 5.55 (s, 2H, CH$_2$); HRMS (ESI) calc. for C$_{18}$H$_{16}$N$_5$O$_4$: [M+H]$^+$ 366.11968, found 366.1197.

Compound 158. To a solution of 5-amino-4,6-dichloropyrimidine (1 equivalent) in a mixture of 1,4-dioxane (3.3 mL/mmol) and water (0.33 mL/mmol) were added 4-benzyloxybenzylamine (1.3 equivalent) and NaHCO$_3$ (2 equivalents). The solution was refluxed for 24 h. After concentration under reduced pressure, the crude product was triturated in water and filtered. The resulting precipitate was then triturated in methanol and filtered to afford pure compound 158 (88%). $^1$H NMR (400 MHz, d$_6$-DMSO) δ 7.74 (s, 1H, CH$_{Ar}$), 7.47-7.36 (m, 4H, 4 CH$_{Ar}$), 7.36-7.30 (m, 1H, CH$_{Ar}$), 7.29-7.21 (m, 3H, 2 CH$_{Ar}$+NH), 6.98 (d, J=8.7 Hz, 2H, 2 CH$_{Ar}$), 5.10 (s, 2H, CH$_2$), 5.08 (bs, 2H, NH$_2$), 4.55 (d, J=5.5 Hz, 2H, CH$_2$); HRMS (ESI) calc. for C$_{18}$H$_{18}$ClN$_4$O: [M+H]$^+$ 341.11637, found 341.1167.

Compound II-1. To a solution of 4-chloroquinoline (1 equivalent) in DMF (7 mL/mmol), palladium(0) tetrakis (triphenylphosphine) (0.1 equivalent) was added. To a solution of potassium carbonate (2.1 equivalents) in DMF (2 mL/mmol), 4-carbamoylphenylboronic acid (1.05 equivalent) was added. After 10 min of stirring the two solutions were combined and refluxed overnight. After filtration on celite, and evaporation under reduced pressure, the crude product was purified by chromatography on silica gel (elution with dichloromethane/methanol) to afford pure compound II-1 (52%). $^1$H NMR (400 MHz, CDCl$_3$) δ 8.98 (d, J=4.4 Hz, 1H, CH$_{Ar}$), 8.25-8.18 (m, 1H, CH$_{Ar}$), 8.02-7.96 (m, 2H, 2 CH$_{Ar}$), 7.88-7.82 (m, 1H, CH$_{Ar}$), 7.76 (ddd, J=8.3, 6.9, 1.3 Hz, 1H, CH$_{Ar}$), 7.64-7.59 (m, 2H, 2 CH$_{Ar}$), 7.53 (ddd, J=8.3 Hz, J=6.9 Hz, J=1.3 Hz, 1H, CH$_{Ar}$), 7.35 (d, J=4.4 Hz, 1H, CH$_{Ar}$), 6.16 (bs, 1H, NH), 5.71 (bs, 1H, NH); HRMS (ESI) calc. for C$_{16}$H$_{13}$N$_2$O: [M+H]$^+$ 249.10224, found 249.1022.

Compound II-2. To a solution of 5-chloroquinoline (1 equivalent) in DMF (7 mL/mmol), palladium(0) tetrakis (triphenylphosphine) (0.1 equivalent) was added. To a solution of potassium carbonate (2.1 equivalents) in DMF (2 mL/mmol), 4-carbamoylphenylboronic acid (1.05 equivalent) was added. After 10 min of stirring the two solutions were combined and refluxed overnight. After filtration on celite, and evaporation under reduced pressure, the crude product was purified by chromatography on silica gel (elution with dichloromethane/methanol) to afford pure compound II-2 (28%). $^1$H NMR (400 MHz, d$_6$-DMSO) δ 8.95 (dd, J=4.1, 1.6 Hz, 1H, CH$_{Ar}$), 8.22-8.16 (m, 1H, CH$_{Ar}$), 8.14-8.07 (m, 2H, 2 CH$_{Ar}$), 8.07-8.02 (m, 2H, 2 CH$_{Ar}$), 7.85 (dd, J=8.5, 7.1 Hz, 1H, CH$_{Ar}$), 7.63-7.56 (m, 3H, 2 CH$_{Ar}$+NH), 7.54 (dd, J=8.6, 4.1 Hz, 1H, CH$_{Ar}$), 7.46 (bs, 1H, NH).

II. Biology

Materials and Methods

Material

Pharmacology, chemicals and reagents. The CFTR activator forskolin and potentiator genistein (Illek et al., 1995) were purchased from LC Laboratories (PKC Pharmaceuticals, Woburn, Mass.). We purchased DIDS (5-Isothiocyanato-2-[2-(4-isothiocyanato-2-sulfophenyl)ethenyl]benzene-1-sulfonic acid) and VX809 (3-(6-(1-(2,2-difluorobenzo[d][1,3]dioxol-5-yl)cyclopropanecarboxamido)-3-methylpyridin-2-yl)benzoic acid) from Selleckchem (Houston, USA). Stock solutions of F (10 mM), G (30 mM), CFTRinh-172 (10 mM), VX809 (10 mM), were prepared in DMSO. We prepared stock solution of iminosugars, miglustat and Iso-LAB ([1,4-dideoxy-2-hydroxymethyl-1,4-imino-L-threitol]) dissolved in water (100 mM) before further dilution.

Methods

Cell culture. HeLa cells expressing wild-type CFTR (spTCF-wt) or F508del-CFTR (spTCF-ΔF) were cultured in Dulbecco's modified Eagle's medium+GlutaMAX™-I (Invitrogen) supplemented with 8% (v/v) fetal bovine serum (FBS), 1% (v/v) penicillin/streptomycin and were selected using Zeocin (50 μg/mL). Both cell lines were grown in standard culture conditions (37° C., 5% C02). Cells were plated in 35 mm plastic dishes for whole-cell patch-clamp recordings and western blot analysis and in 96-well plates for cytotoxicity assay. For all cell culture, culture media were renewed every 2 days.

Western Blot analysis. Cell lysates (10 mM Tris, 1% Nonidet P-40, 0.5% sodium deoxycholate, pH 7.5) were separated 72 h after seeding for HeLa cells by 5% SDS-PAGE (50 μg of protein/well). After saturation, nitrocellulose membrane was incubated overnight at 4° C. in phosphate-buffered saline, 0.1% Tween 20 with 1 μg/ml mouse anti-CFTR monoclonal antibody (clone MAB3480; Chemicon International, Millipore Bioscience Research Reagents, Temecula, Calif.). After washing, goat peroxidase-conjugated anti-mouse IgG (1:10 000; Sigma-Aldrich) was used as secondary antibody. CFTR was visualized by chemiluminescence with ECL Western blotting detection reagent (GE Healthcare, Buckinghamshire, UK).

Iodide efflux. CFTR chloride channel activity was assayed by measuring the rate of iodide ($^{125}$I) efflux from living cells. All experiments were performed with a Multi-PROBE® IIex robotic liquid handling system (Perkin Elmer Life Sciences, Courtaboeuf, France). At the beginning of each experiment, cells were washed twice with efflux buffer containing (in mM) 136.9 NaCl, 5.4 KCl, 0.3 KH$_2$PO$_4$, 0.3

NaH$_2$PO$_4$, 1.3 CaCl$_2$, 0.5 MgCl$_2$, 0.4 MgSO$_4$, 5.6 glucose and 10 HEPES, pH 7.4. Cells were incubated in efflux buffer containing Na$^{125}$I (1 µCi Na$^{125}$I/ml, NEN, Boston, Mass.) during 1 h at 37° C., then washed with efflux medium to remove extracellular $^{125}$I. The loss of intracellular $^{125}$I was determined by removing the medium with efflux buffer every 1 min for up to 10 min. The first three aliquots were used to establish a stable baseline in efflux buffer alone. A medium containing the activators of CFTR (Fsk 10 µM+Gst 30 µM) and the appropriate drug was used for the remaining aliquots. Residual radioactivity was extracted with 0.1 N NaOH/0.1% SDS, and determined using a Packard Cobra™ II gamma counter (Perkin Elmer life Sciences, Courtaboeuf, France). The fraction of initial intracellular $^{125}$I lost during each time point was collected and time-dependent rates of $^{125}$I efflux calculated from: ln ($^{125}$It$_1$/$^{125}$It$_2$)/(t$_1$-t$_2$) where $^{125}$It is the intracellular $^{125}$I at time t, and t$_1$ and t$_2$ successive time points. Curves were constructed by plotting rate of $_{125}$I versus time. All comparisons were based on maximal values for the time-dependent rates (k=peak rates, min−1) excluding the points used to establish the baseline (k$_{peak}$-k$_{basal}$, min$^{-1}$), and histograms were presented as percentage of activation.

Time dependence. Time dependence of the compounds was assayed by measuring the time necessary for an optimal correction of the protein F508del-CFTR. HeLa cells expressing F508del-CFTR were incubated with the compound in acute treatment or during 4, 8, 12, 24 or 48 hours and the iodide efflux was measured as described previously. In some experiments, the incubation with the compound and the measure of iodide efflux are separated by a rinse and a waiting period of 4, 6, 8, 12 or 24 hours before activation with the medium containing the activators of CFTR (Fsk 10 µM+Gst 30 µM).

Statistical analysis. Results are expressed as means±SE of n observations. Statistical analysis was carried out using GraphPad (Prism, La Jolla, Calif.) version 5.0 for Windows (GraphPad Software). To compare sets of data, we used one-way Anova followed by Dunnett multiple-comparison test or Student's t test. Differences were considered statistically significant when P<0.05.

Results

Maturation Profile

In order to evaluate the effect of the compounds on the correction of the mutant protein, we assessed the maturation F508del-CFTR maturation profile. WT core-glycosylated immature CFTR (referred here as B-band CTFR) reaches the plasma membrane after a modification process that allows the protein to become mature and fully glycosylated (referred here as C-band CFTR). On the contrary, F508del-CFTR remains trapped in the endoplasmic reticulum (ER) as B-band CFTR.

We thus performed a series of western blot experiments mimicking all the experimental conditions to monitor the C-band appearance.

Immunoblots are presented in FIG. 1. As shown in FIG. 1, we observed mature, fully glycosylated C-band F508del-CFTR in the presence of the compounds 1, 7, 10, 14, 20 and 49, compared with untreated cells. Therefore, the compounds of the invention correct the trafficking of F508del-CFTR to the plasma membrane, where the protein can play its role of chloride channel.

Iodide Transport

Next we investigated the effect of the compounds on the activity of F508del-CFTR by performing iodide efflux experiments. Iodide efflux of cells treated with the compounds was measured and compared with iodide efflux obtained with incubation with VX809, a known corrector of CFTR, normalized at 100%. Results were classified in 3 groups: +++≥60%; 35%≤++<60% and 10%≤+<35%.

The results are shown in Table 3. Iodide efflux of untreated cells expressing F508del-CFTR is below 10% (3.6%).

TABLE 3

Iodide efflux of cells expressing F508del and incubated with different compounds of the invention

| Compound number | Iodide efflux |
| --- | --- |
| II-1 | +++ |
| 1 | ++ |
| 2 | + |
| 4 | +++ |
| 5 | ++ |
| 6 | + |
| 7 | +++ |
| 9 | + |
| 10 | ++ |
| 11 | +++ |
| 12 | + |
| 14 | +++ |
| 15 | + |
| 16 | + |
| 17 | + |
| 18 | ++ |
| 20 | ++ |
| 21 | +++ |
| 22 | ++ |
| 23 | +++ |
| 25 | + |
| 26 | + |
| 27 | +++ |
| 28 | ++ |
| 29 | +++ |
| 30 | ++ |
| 31 | + |
| 33 | +++ |
| 47 | +++ |
| 48 | +++ |
| 49 | +++ |
| 53 | + |
| 54 | +++ |
| 55 | +++ |
| 56 | +++ |
| 57 | +++ |
| 58 | ++ |
| 59 | ++ |
| 60 | ++ |
| 61 | ++ |
| 62 | + |
| 63 | + |
| 64 | + |
| 65 | ++ |
| 79 | + |
| 80 | + |
| 81 | + |
| 82 | + |
| 83 | + |
| 85 | + |
| 86 | + |
| 88 | + |
| 89 | + |
| 90 | + |
| 91 | + |
| 92 | + |
| 93 | + |
| 94 | + |
| 95 | + |
| 96 | + |
| 97 | + |
| 98 | + |
| 101 | ++ |
| 102 | +++ |
| 103 | + |

TABLE 3-continued

Iodide efflux of cells expressing F508del and incubated with different compounds of the invention

| Compound number | Iodide efflux |
|---|---|
| 104 | ++ |
| 105 | +++ |
| 106 | + |
| 107 | +++ |
| 108 | + |
| 109 | ++ |
| 110 | + |
| 111 | ++ |
| 112 | + |
| 113 | +++ |
| 114 | +++ |
| 115 | +++ |
| 116 | ++ |
| 117 | ++ |
| 118 | +++ |
| 119 | ++ |
| 120 | ++ |
| 121 | + |
| 122 | + |
| 123 | + |
| 124 | + |
| 125 | +++ |
| 126 | +++ |
| 127 | ++ |
| 128 | ++ |
| 129 | +++ |
| 130 | +++ |

The results show that the tested compounds restore the activation of a chloride conductance dependent of AMPc on cells expressing F508del-CFTR, compared with untreated cells. Thus these compounds have a corrector activity on F508del-CFTR.

Taken together, these results demonstrate that the compounds of the invention are good candidates for the treatment of cystic fibrosis.

Combination of Compounds

Figure 2:
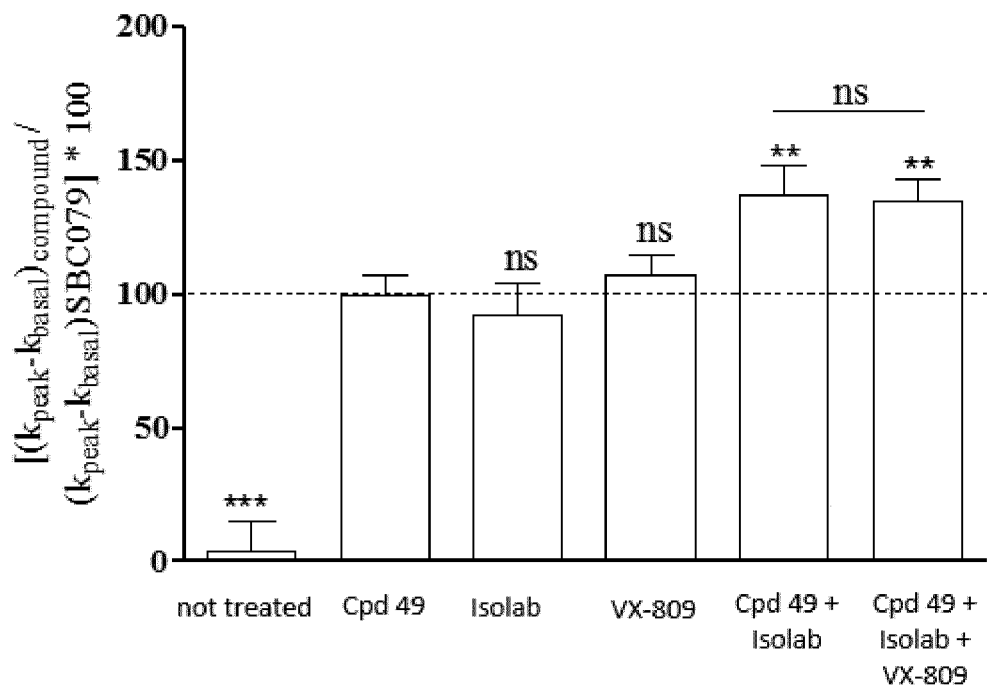
FIG. 2 is a histogram showing the iodide efflux of HeLa cells expressing F508del-CFTR incubated with the compound 49 of the invention, Isolab, VX-809, or combinations thereof.

Then we tested combinations of compounds of the invention with other correctors of F508del-CFTR, especially with Isolab and VX-809, by performing the same iodide efflux experiments. The results, presented in FIG. 2, show that the combination of the tested compounds enhances the conductance of F508del-CFTR more than the compounds alone.

These results demonstrate the interest to use a combination of compounds to treat cystic fibrosis.

Time Dependence

Figure 3:
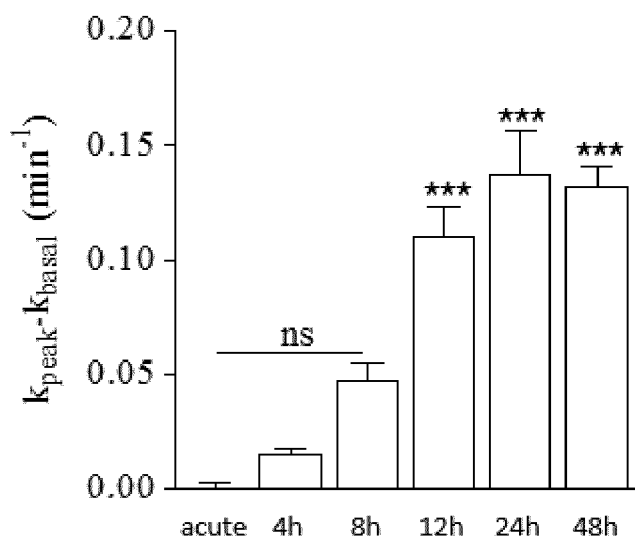
FIG. 3 is a histogram showing the iodide efflux of HeLa cells expressing F508del-CFTR incubated with the compound 49 during 4, 8, 12, 24 or 48 hours.

To evaluate the relevancy of the correction of F508del-CFTR by the compound of the invention, we then tested its "time dependence" by studying the period of incubation necessary for an optimal correction. The results presented in FIG. 3 show that the optimal correction is reached after a treatment of 12 hours and is conserved after a treatment of 24 or 48 hours.

Figure 4:
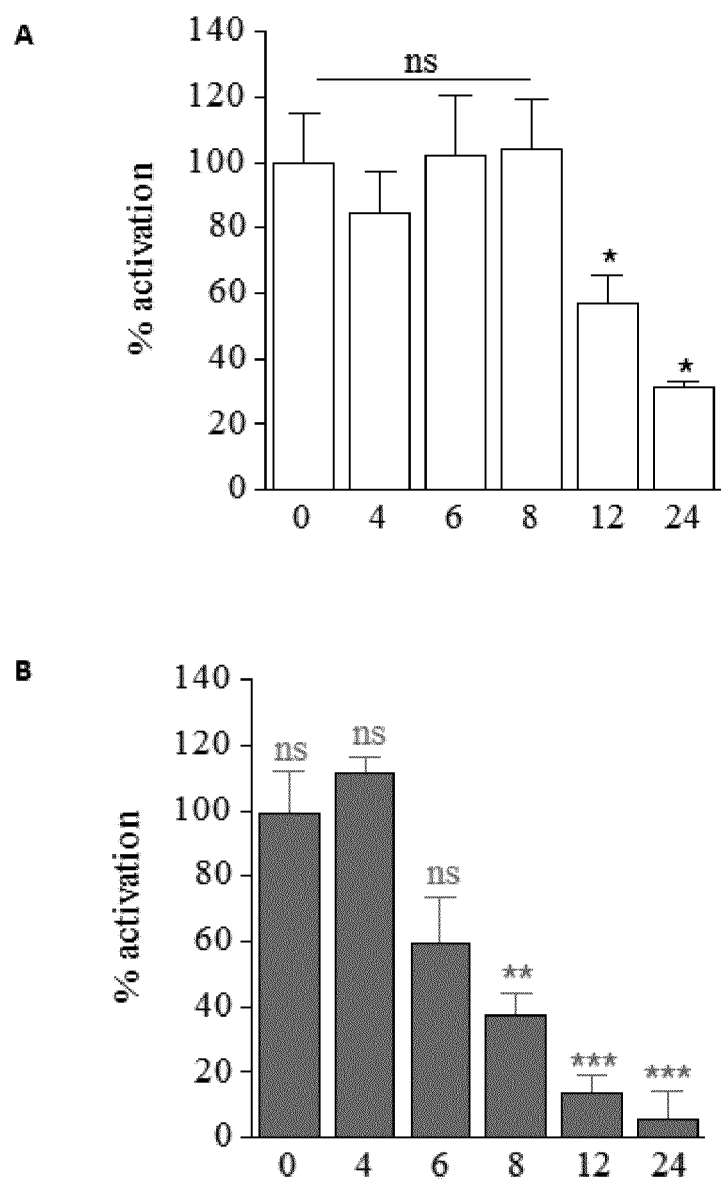
FIG. 4A is a histogram showing the activation of F508del-CFTR of cells incubated with the compound 49 of the invention during the time necessary for an optimal correction and then rinsed. The iodide efflux was measured after the time indicated on the x-axis.
FIG. 4B is a histogram showing the activation of F508del-CFTR of cells incubated with the compound VX-508 during the time necessary for an optimal correction and then rinsed. The iodide efflux was measured after the time indicated on the x-axis.

We then wondered if the compound could modify the stability of the protein. After the incubation with the compound during the necessary time for an optimal correction, the cells were rinsed. After 4, 6, 8, 12 or 24 hours the activation of CFTR was realized and the activity of F508del-CFTR measured. As shown in FIG. 4A, the corrector activity of the compound 49 remains after 8 hours and reaches 50% of its maximum after 12 hours. Besides, the same experiments performed with the corrector VX-809 presented in FIG. 4B show less than 50% of activity after 8 hours.

The invention claimed is:

1. A compound, selected from the group consisting of
(S)-2-((2-chloro-9-(4-(hydroxymethyl)phenyl)-9H-purin-6-yl)amino)propanoic acid;
(S)-tert-butyl 2-((2-chloro-9-(4-(hydroxymethyl)phenyl)-9H-purin-6-yl)amino)propanoate;
4-(2-chloro-6-(diethylamino)-9H-purin-9-yl)benzamide;
4-(6-amino-2-chloro-9H-purin-9-yl)benzamide;
4-(2-chloro-6-((1,3-dihydroxypropan-2-yl)amino)-9H-purin-9-yl)benzamide;
(S)-2-((9-(4-carbamoylphenyl)-2-chloro-9H-purin-6-yl)amino)-3-hydroxypropanoic acid;
2-((9-(4-carbamoylphenyl)-2-chloro-9H-purin-6-yl)amino)acetic acid;
tert-butyl 2-((9-(4-carbamoylphenyl)-2-chloro-9H-purin-6-yl)amino)acetate;
4-(2-chloro-6-((4-methoxybenzyl)amino)-9H-purin-9-yl)benzamide;
(S)-2-((9-(4-carbamoylphenyl)-2-chloro-9H-purin-6-yl)amino)propanoic acid;
(S)-tert-butyl 2-((9-(4-carbamoylphenyl)-2-chloro-9H-purin-6-yl)amino)propanoate;
(4-(6-amino-2-chloro-9H-purin-9-yl)phenyl)methanol;
(S)-2-((9-(4-(hydroxymethyl)phenyl)-2-((3-phenylpropyl)amino)-9H-purin-6-yl)amino)propanoic acid; and
4-(6-((4-methoxybenzyl)amino)-2-((3-phenylpropyl)amino)-9H-purin-9-yl)benzamide.

2. A pharmaceutical composition comprising a compound selected from the group consisting of
(S)-2-((2-chloro-9-(4-(hydroxymethyl)phenyl)-9H-purin-6-yl)amino)propanoic acid;
(S)-tert-butyl 2-((2-chloro-9-(4-(hydroxymethyl)phenyl)-9H-purin-6-yl)amino)propanoate;
4-(2-chloro-6-(diethylamino)-9H-purin-9-yl)benzamide;
4-(6-amino-2-chloro-9H-purin-9-yl)benzamide;
4-(2-chloro-6-((1,3-dihydroxypropan-2-yl)amino)-9H-purin-9-yl)benzamide;
(S)-2-((9-(4-carbamoylphenyl)-2-chloro-9H-purin-6-yl)amino)-3-hydroxypropanoic acid;
2-((9-(4-carbamoylphenyl)-2-chloro-9H-purin-6-yl)amino)acetic acid;
tert-butyl 2-((9-(4-carbamoylphenyl)-2-chloro-9H-purin-6-yl)amino)acetate;
4-(2-chloro-6-((4-methoxybenzyl)amino)-9H-purin-9-yl)benzamide;
(S)-2-((9-(4-carbamoylphenyl)-2-chloro-9H-purin-6-yl)amino)propanoic acid;
(S)-tert-butyl 2-((9-(4-carbamoylphenyl)-2-chloro-9H-purin-6-yl)amino)propanoate;
(4-(6-amino-2-chloro-9H-purin-9-yl)phenyl)methanol;
(S)-2-((9-(4-(hydroxymethyl)phenyl)-2-((3-phenylpropyl)amino)-9H-purin-6-yl)amino)propanoic acid; and
4-(6-((4-methoxybenzyl)amino)-2-((3-phenylpropyl)amino)-9H-purin 9 yl)
and at least one pharmaceutically acceptable carrier.

3. A medicament comprising a compound selected from the group consisting of
(S)-2-((2-chloro-9-(4-(hydroxymethyl)phenyl)-9H-purin-6-yl)amino)propanoic acid;
(S)-tert-butyl 2-((2-chloro-9-(4-(hydroxymethyl)phenyl)-9H-purin-6-yl)amino)propanoate;
4-(2-chloro-6-(diethylamino)-9H-purin-9-yl)benzamide;
4-(6-amino-2-chloro-9H-purin-9-yl)benzamide;
4-(2-chloro-6-((1,3-dihydroxypropan-2-yl)amino)-9H-purin-9-yl)benzamide;
(S)-2-((9-(4-carbamoylphenyl)-2-chloro-9H-purin-6-yl)amino)-3-hydroxypropanoic acid;
2-((9-(4-carbamoylphenyl)-2-chloro-9H-purin-6-yl)amino)acetic acid;

tert-butyl 2-((9-(4-carbamoylphenyl)-2-chloro-9H-purin-6-yl)amino)acetate;

4-(2-chloro-6((4-methoxybenzyl)amino)-9H-purin-9-yl)benzamide;

(S)-2-((9-(4-carbamoylphenyl)-2-chloro-9H-purin-6-yl)amino)propanoic acid;

(S)-tert-butyl 2-((9-(4-carbamoylphenyl)-2-chloro-9H-purin-6-yl)amino)propanoate;

(4-(6-amino-2-chloro-9H-purin-9-yl)phenyl)methanol;

(S)-2-((9-(4-(hydroxymethyl)phenyl)-2-((3-phenylpropyl)amino)-9H-purin-6-yl)amino)propanoic acid; and 4-(6-((4-methoxybenzyl)amino)-2-((3-phenylpropyl)amino)-9H-purin-9-yl)benzamide.

4. A method of treatment of cystic fibrosis associated with chloride channels comprising the administration to a patient in need thereof of a compound selected from the group consisting of (S)-2-((2-chloro-9-(4-(hydroxymethyl)phenyl)-9H-purin-6-yl)amino)propanoic acid;

(S)-tert-butyl 2-((2-chloro-9-(4-(hydroxymethyl)phenyl)-9H-purin-6-yl)amino)propanoate;

4-(2-chloro-6-(diethylamino)-9H-purin-9-yl)benzamide;

4-(6-amino-2-chloro-9H-purin-9-yl)benzamide;

4-(2-chloro-6-((1,3-dihydroxypropan-2-yl)amino)-9H-purin-9-yl)benzamide;

(S)-2-((9-(4-carbamoylphenyl)-2-chloro-9H-purin-6-yl)amino)-3-hydroxypropanoic acid;

2-((9-(4-carbamoylphenyl)-2-chloro-9H-purin-6-yl)amino)acetic acid;

tert-butyl 2-((9-(4-carbamoylphenyl)-2-chloro-9H-purin-6-yl)amino)acetate;

4-(2-chloro-6-((4-methoxybenzyl)amino)-9H-purin-9-yl)benzamide;

(S)-2-((9-(4-carbamoylphenyl)-2-chloro-9H-purin-6-yl)amino)propanoic acid;

(S)-tert-butyl 2-((9-(4-carbamoylphenyl)-2-chloro-9H-purin-6-yl)amino)propanoate;

(4-(6-amino-2-chloro-9H-purin-9-yl)phenyl)methanol;

(S)-2-((9-(4-(hydroxymethyl)phenyl)-2-((3-phenylpropyl)amino)-9H-purin-6-yl)amino)propanoic acid; and 4-(6-((4-methoxybenzyl)amino)-2-((3-phenylpropyl)amino)-9H-purin-9-yl)benzamide.

5. The method according to claim 4, wherein the cystic fibrosis is due to a mutation of the gene encoding the CFTR protein.

6. The method according to claim 5, wherein the cystic fibrosis is due to a deletion of the phenylalanine residue at position 508.

\* \* \* \* \*